United States Patent
Spiegelman et al.

(10) Patent No.: US 10,429,384 B2
(45) Date of Patent: Oct. 1, 2019

(54) COMPOSITIONS, KITS, AND METHODS FOR IDENTIFICATION, ASSESSMENT, PREVENTION, AND THERAPY OF METABOLIC DISORDERS

(75) Inventors: Bruce M. Spiegelman, Waban, MA (US); Jang Hyun Choi, Brookline, MA (US); Shingo Kajimura, Boston, MA (US); Alexander Banks, Cambridge, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 150 days.

(21) Appl. No.: 13/522,736

(22) PCT Filed: Jan. 20, 2011

(86) PCT No.: PCT/US2011/021855
§ 371 (c)(1),
(2), (4) Date: Sep. 7, 2012

(87) PCT Pub. No.: WO2011/091134
PCT Pub. Date: Jul. 28, 2011

(65) Prior Publication Data
US 2013/0019326 A1 Jan. 17, 2013

Related U.S. Application Data

(60) Provisional application No. 61/336,483, filed on Jan. 22, 2010, provisional application No. 61/341,455, filed on Mar. 31, 2010, provisional application No. 61/399,975, filed on Jul. 21, 2010.

(51) Int. Cl.
*G01N 33/53* (2006.01)
*G01N 33/566* (2006.01)
*C07K 14/705* (2006.01)
*C12Q 1/6883* (2018.01)

(52) U.S. Cl.
CPC ..... *G01N 33/566* (2013.01); *C07K 14/70567* (2013.01); *C12Q 1/6883* (2013.01); *C12Q 2600/106* (2013.01); *G01N 2333/70567* (2013.01); *G01N 2440/14* (2013.01); *G01N 2500/04* (2013.01); *G01N 2800/04* (2013.01); *G01N 2800/52* (2013.01)

(58) Field of Classification Search
None
See application file for complete search history.

(56) References Cited

FOREIGN PATENT DOCUMENTS

KR   2009 0100567   9/2009

OTHER PUBLICATIONS

Sato et al., 2003, Geneseq Accession No. ABR57063, computer printout pp. 4-6.*
Albrektsen et al. (2002) Diabetes 51: 1042-1051.*
Anghel et al., "Fat poetry: a kingdom for PPARγ," Cell Research, 17:486-511 (2007).
Bruning et al., "Partial Agonists Activate PPARγ Using a Helix 12 Independent Mechanism," Structure, 15(10):1258-1271 (2007).
Camp et al., "Regulation of Peroxisome Proliferator-activated Receptor γ Activity by Mitogen-activated Protein Kinase," Juornal of Biological Chemistry, 272(16):10811-10816 (1997).
Chen et al., "Phosphorylation of PPARγ via Active ERK1/2 Leads to its Physical Association With p65 and Inhibition of NF-κβ," Journal of Cellular Biochemistry, 90:732-744 (2003).
Forman et al., "15-Deoxy-$\Delta^{12,\,14}$-Prosaglandin $J_2$ Is a Ligand for the Adipocyte Determination Factor PPARγ," Cell, 83(5):803-812 (1995).
Hasegawa et al., "The PPARgamma-selective ligand BRL-49653 differentially regulates the fate choices of rat calvaria versus rat bone marrow stromal cell populations," BMC Deveopmental Biology, Biomed Central Ltd., 8(1):71 (2008).
Hu et al., "Inhibition of Adipogenesis Through MAP Kinase-Mediated Phosphorylation of PPARγ," Science, 274:2100-2103 (1996).
Joosen et al., "The PPARγ ligand rosiglitazone influences triacylglycerol metabolism in non-obese males, without increasing the transcriptional activity of PPARγ in the subcutaneous adipose tissue," British Journal of Nutrition, 99(3):487-493 (2008).
Kim et al., "CDK5 is a novel regulatory protein in PPARγ ligand-induced antiproliferation," International Journal of Oncology, 28(1):191-194 (2006).
Lehrke et al., "The Many Faces of PPARγ," Cell, 123:993-999 (2005).
Okazaki et al., "Thiazolidinediones Inhibit Osteoclast-Like Cell Formation and Bone Resorption in Vitro," Endocrinology, 140(11):5060-5065 (1999).
Rangwala et al., "Genetic Modulation of PPARγ Phosphorylation Regulates Insulin Sensitivity," Developmental Cell, 5(4):657-663 (2003).
Reginato et al., "A Potent Antidiabetic Thiazolidinedione with Unique Peroxisome Proliferator-activated Receptor γ-activating Properties," The Journal of Biological Chemistry, 273(49):32679-32684 (1998).
Seale et al., "Transcriptional control of brown adipocyte development and physiological function—of mice and men," Genes & Development, 23:788-797 (2009).

(Continued)

*Primary Examiner* — Michael D Pak
(74) *Attorney, Agent, or Firm* — Foley Hoag LLP

(57) ABSTRACT

The invention provides methods and compositions for selectively promoting anti-metabolic disorder activity over classical PPAR gamma activation through modulation of PPAR gamma phosphorylation (e.g., Ser-273 phosphorylation of murine peroxisome proliferator activated receptor gamma (PPAR gamma) 2 or a corresponding serine residue in a murine PPAR gamma 2 homolog, including a human). Also provided are methods for preventing, treating, or predictiving responsiveness of therapies for metabolic disorders in a subject through selective inhibition of such PPAR gamma phosphorylation. Further provided are methods for identifying compounds that are capable of modulating such PPAR gamma phosphorylation.

18 Claims, 15 Drawing Sheets

Specification includes a Sequence Listing.

(56) References Cited

OTHER PUBLICATIONS

Seber et al., "The effect of dual PPAR α/γ stimulation with combination of rosiglitazone with fenofibrate on metabolic parameters in type 2 diabetic patients," Diabetes Research and Clinical Practice, 71(1):52-58 (2006).
Tontonoz et al., "Fat and Beyond: The Diverse Biology of PPARγ," Annu. Rev. Biochem., 77:289-312 (2008).
Tontonoz et al., "Regulation of adipocyte gene expression and differentiation by peroxisome proliferator activated receptor γ," Current Opinion in Genetics & Development, 5:571-576 (1995).
Watkins et al., "Lipid metabolome-wide effects of the PPARγ agonist rosiglitazone," The Journal of Lipid Research, 43(11):1809-1817 (2002).
Xin et al., "Peroxisome Proliferator-activated Receptor γ Ligands Are Potent Inhibitors of Angiogenesis in Vitro and in Vivo," The Journal of Biological Chemistry, 274(13):9116-9121 (1999).
International Search Report dated Sep. 14, 2011 from PCT/US2011/021855.

\* cited by examiner

A

B

|  | 7 weeks Chow | 7 weeks HFD | 13 weeks Chow | 13 weeks HFD |
|---|---|---|---|---|
| Weight (grams) | 26.2 ± 0.3 | 33.8 ± 1*** | 29.4 ± 0.6 | 44.5 ± 1.1*** |
| Glucose (mg/dl) | 58.2 ± 6.4 | 92.6 ± 5.4 | 115.4 ± 8.9 | 124.4 ± 6.5 |
| Insulin (ng/ml) | 0.1 ± 0.03 | 0.18 ± 0.06 | 0.24 ± 0.03 | 1.07 ± 0.13** |

| | | Delta phosphoPPARg | Delta GIR | Delta TG | Delta Weight | Delta VO2max | Delta FPG | Delta OGGT | Delta FPI |
|---|---|---|---|---|---|---|---|---|---|
| Delta phosphoPPARg | Pearson Correlation | 1 | -,812 | -,656 | ,238 | -,638 | ,729 | -,063 | ,804 |
| | Sig. (2-tailed) | | ,008 | ,055 | ,537 | ,065 | ,026 | ,871 | ,009 |
| | N | 9 | 9 | 9 | 9 | 9 | 9 | 9 | 9 |
| Delta GIR | Pearson Correlation | -,812 | 1 | ,437 | ,196 | ,666 | -,840 | -,366 | -,788 |
| | Sig. (2-tailed) | ,008 | | ,240 | ,613 | ,050 | ,005 | ,333 | ,012 |
| | N | 9 | 9 | 9 | 9 | 9 | 9 | 9 | 9 |
| Delta TG | Pearson Correlation | -,656 | ,437 | 1 | -,284 | ,194 | -,294 | ,284 | -,664 |
| | Sig. (2-tailed) | ,055 | ,240 | | ,459 | ,617 | ,442 | ,459 | ,051 |
| | N | 9 | 9 | 9 | 9 | 9 | 9 | 9 | 9 |
| Delta Weight | Pearson Correlation | ,238 | ,196 | -,284 | 1 | -,282 | -,032 | -,365 | ,346 |
| | Sig. (2-tailed) | ,537 | ,613 | ,459 | | ,462 | ,934 | ,335 | ,362 |
| | N | 9 | 9 | 9 | 9 | 9 | 9 | 9 | 9 |
| Delta VO2max | Pearson Correlation | -,638 | ,666 | ,194 | -,282 | 1 | -,528 | -,102 | -,601 |
| | Sig. (2-tailed) | ,065 | ,050 | ,617 | ,462 | | ,144 | ,794 | ,087 |
| | N | 9 | 9 | 9 | 9 | 9 | 9 | 9 | 9 |
| Delta FPG | Pearson Correlation | ,729 | -,840 | -,294 | -,032 | -,528 | 1 | ,298 | ,762 |
| | Sig. (2-tailed) | ,026 | ,005 | ,442 | ,934 | ,144 | | ,436 | ,017 |
| | N | 9 | 9 | 9 | 9 | 9 | 9 | 9 | 9 |
| Delta OGGT | Pearson Correlation | -,063 | -,366 | ,284 | -,365 | -,102 | ,298 | 1 | ,130 |
| | Sig. (2-tailed) | ,871 | ,333 | ,459 | ,335 | ,794 | ,436 | | ,738 |
| | N | 9 | 9 | 9 | 9 | 9 | 9 | 9 | 9 |
| Delta FPI | Pearson Correlation | ,804 | -,788 | -,664 | ,346 | -,601 | ,762 | ,130 | 1 |
| | Sig. (2-tailed) | ,009 | ,012 | ,051 | ,362 | ,087 | ,017 | ,738 | |
| | N | 9 | 9 | 9 | 9 | 9 | 9 | 9 | 9 |

…

COMPOSITIONS, KITS, AND METHODS FOR IDENTIFICATION, ASSESSMENT, PREVENTION, AND THERAPY OF METABOLIC DISORDERS

CROSS-REFERENCE TO RELATED APPLICATIONS

This application is the U.S. National Stage Application of International Application No. PCT/US2011/021855, filed on Jan. 20, 2011, which claims the benefit of priority to U.S. Provisional Application No. 61/336,483, filed on Jan. 22, 2010, U.S. Provisional Application No. 61/341,455, filed on Mar. 31, 2010, and U.S. Provisional Application No. 61/399,975, filed on Jul. 21, 2010; the entire contents of each of which application are expressly incorporated herein by reference.

GOVERNMENT SUPPORT

This invention was made with government support under grant number DK031405 awarded by The National Institutes of Health. The government has certain rights in the invention.

BACKGROUND OF THE INVENTION

Metabolic disorders comprise a collection of health disorders or risks that increase the risk of morbidity and loss of qualify of life. For example, diabetes, obesity, including central obesity (disproportionate fat tissue in and around the abdomen), atherogenic dyslipidemia (these include a family of blood fat disorders, e.g., high triglycerides, low HDL cholesterol, and high LDL cholesterol that can foster plaque buildups in the vascular system, including artery walls), high blood pressure (130/85 mmHg or higher), insulin resistance or glucose intolerance (the inability to properly use insulin or blood sugar), a chronic prothrombotic state (e.g., characterized by high fibrinogen or plasminogen activator inhibitor-1 levels in the blood), and a chronic proinflammatory state (e.g., characterized by higher than normal levels of high-sensitivity C-reactive protein in the blood), are all metabolic disorders collectively afflicting greater than 50 million people in the United States. In addition, the number of people afflicted with metabolic disorders correlates with increase in age, affecting more than 40 percent of people in their 60s and 70s.

Although treatments for such metabolic disorders do exist, they generally suffer from severe side effects. For example, agonists of the peroxisome proliferator-activated receptor gamma (PPAR gamma) nuclear receptor transcription factor, such as rosiglitazone and pioglitazone, have received regulatory approval for the treatment of type 2 diabetes in the United States and Europe. However, side effects or conditions that can be provoked or aggravated by such thiazolidinedione and non-thiazolidinedione PPAR gamma agonists, including weight gain, fluid retention, peripheral edema, and pulmonary edema, limit the clinical utility and safety of such compounds. Thus, while there are several strategies for treating metabolic disorders, such as obesity predisposition, insulin resistance, high blood pressure, dyslipidemia, etc., the molecular basis for controlling such disorders without provoking or aggravating side effects is unclear, making diagnosis or prognosis of these metabolic disorders problematic and the design of therapeutic agents to treat them quite difficult. Accordingly, there is a great need in the art to identify molecular regulators of metabolic disorders, including the generation of diagnostic, prognostic, and therapeutic agents, such as orally active small molecules, that in turn regulate such molecular regulators so as to effectively control metabolic disorders in subjects.

SUMMARY OF THE INVENTION

The present invention, at least in part, is based on the discovery that peroxisome proliferator activated receptor gamma (PPAR gamma), the master regulator of lipid metabolism in adipose tissue, is directly phosphorylated by cyclin dependent kinase 5 (cdk5) (e.g., Ser-273 phosphorylation of PPAR gamma 2 or a corresponding serine residue in a murine PPAR gamma 2 homolog), and that this covalent modification causes a pathological pattern of gene expression associated with increased body weight, obesity, insulin resistance, and other metabolic disorders, as described herein. In addition, as described herein, PPAR gamma ligands that directly inhibit Ser-273 phosphorylation of PPAR gamma can reverse such metabolic disorders independently of classical PPAR gamma agonist activation. Accordingly, specific inhibition of phospho-Ser-273 on PPAR gamma can eliminate undesirable side effects observed with classical PPAR gamma agonists in the context of diagnosing, prognosing, and treating metabolic disorders, including diabetes and obesity. Other features and advantages of the invention will be apparent from the following detailed description and claims.

Accordingly, the present invention provides methods for identifying a compound which inhibits Ser-273 phosphorylation of murine PPAR gamma 2 or a corresponding serine residue in a murine PPAR gamma 2 homolog comprising contacting a sample comprising said murine PPAR gamma 2 or a corresponding serine residue in a murine PPAR gamma 2 homolog with a test compound and determining the ability of the test compound to inhibit said Ser-273 phosphorylation of murine PPAR gamma 2 or a corresponding serine residue in a murine PPAR gamma 2 homolog thereby identifying a compound which selectively inhibits said Ser-273 phosphorylation of murine PPAR gamma 2 or a corresponding serine residue in a murine PPAR gamma 2 homolog. In one embodiment, the sample is selected from the group consisting of in vitro, ex vivo, and in vivo samples. In another embodiment, inhibition of Ser-273 phosphorylation of murine PPAR gamma 2 or a corresponding serine residue in a murine PPAR gamma 2 homolog is determined by analyzing the amount of Ser-273 phosphorylated PPAR gamma relative to total PPAR gamma and comparing the ratio to a control (e.g., such as the ratio from treatment with rosiglitazone under standard conditions). In still another embodiment, the method further comprises a step of determining whether the test compound directly binds said murine PPAR gamma 2 or a corresponding serine residue in a murine PPAR gamma 2 homolog.

In another aspect, methods are provided for identifying a compound that binds PPAR gamma and which selectively promotes anti-metabolic disorder activity over classical PPAR gamma activation in a cell type, the method comprising, determining whether the compound binds PPAR gamma and comparing the amount and/or activity of a marker in a first sample of the cell type maintained in the presence of the test compound, wherein the marker is selected from the group of markers listed in Table 1 or 2, to the amount and/or activity of the marker in a second sample which is a control, wherein a significantly higher amount and/or activity of a marker listed in Table 1 in the first sample relative to the second sample indicates that the test compound selectively promotes anti-metabolic disorder activity over classical PPAR gamma activation in the cell type and/or wherein a significantly lower amount and/or activity of a marker listed in Table 2 in the first sample relative to the second sample, indicates that the test compound selectively promotes anti-metabolic disorder activity over classical PPAR gamma activation in the cell type. In one embodiment, the cell type is selected from the group consisting of: preadipocytes, mature white adipocytes, brown adipocytes, monocytes, and macrophages. In another embodiment, the first and/or second sample is selected from the group consisting of in vitro, ex vivo, and in vivo samples. In still another embodiment, the first and/or second sample is obtained from an animal model of a metabolic disorder. In yet another embodiment, the first and/or second sample is selected from the group consisting of tissue, whole blood, serum, plasma, buccal scrape, saliva, cerebrospinal fluid, urine, stool, and bone marrow. In another embodiment, the first and second samples are portions of a single sample obtained from a subject. In still another embodiment, the second sample comprises cells of the same cell type as the first sample maintained in the absence of the test compound. In yet another embodiment, the second sample comprises cells of the same cell type as the first sample treated with rosiglitazone. In another embodiment, a significantly higher amount and/or activity comprises upregulating the amount and/or activity of the marker listed in Table 1 at least 25% relative to the second sample. In yet another embodiment, a significantly lower amount and/or activity comprises downregulating the amount and/or activity of the marker listed in Table 2 at least 25% relative to the second sample. In still another embodiment, the amount of the marker is compared, for example, wherein the amount of the marker is determined by determining the level of protein expression of the marker (e.g., using a reagent which specifically binds with the protein such as an antibody, an antibody derivative, and an antibody fragment, such as an antibody that binds to PPAR-gamma and an antibody that binds to a peptide comprising a consensus cdk5 phosphorylated site). In yet another embodiment, the level of expression of the marker in the sample is assessed by detecting the presence in the sample of a transcribed polynucleotide or portion thereof (e.g., mRNA or a cDNA and/or further comprising amplifying the transcribed polynucleotide) or is assessed by detecting the presence in the sample of a transcribed polynucleotide which anneals with the marker or anneals with a portion of a polynucleotide under stringent hybridization conditions. In another embodiment, the marker is phosphorylated Ser-273 on murine PPAR gamma 2 or a corresponding serine residue in a murine PPAR gamma 2 homolog. In still another embodiment, the metabolic disorder is selected from the group consisting of: glucose intolerance, insulin resistance, hypertension, dyslipidemia, obesity, type II diabetes, hyperglycemia, hyperinsulinemia, elevated systolic and diastolic blood pressure, hypertrigliceridemia, hypercholesterolemia, and body mass index greater than 30. In yet another embodiment, PPAR gamma comprises the amino acid sequence set forth in SEQ ID NO:1-7.

In still another aspect, methods are provided for assessing the efficacy of a compound that binds PPAR gamma for selectively promoting anti-metabolic disorder activity over classical PPAR gamma activation in a subject, the method comprising (a) detecting in a subject sample at a first point in time, the amount and/or activity of a marker, wherein the marker is a marker listed in Table 1 or 2, repeating step (a) the step during at least one subsequent point in time after administration of the compound; and comparing the amount and/or activity detected in steps a) and b), wherein a significantly higher amount and/or activity of a marker listed in Table 1 in the first subject sample relative to at least one subsequent subject sample, indicates that the test compound selectively promotes anti-metabolic disorder activity over classical PPAR gamma activation in the subject and/or wherein a significantly lower amount and/or activity of a marker listed in Table 2 in the first subject sample relative to at least one subsequent subject sample, indicates that the test compound selectively promotes anti-metabolic disorder activity over classical PPAR gamma activation in the subject. In one embodiment, the subject has undergone treatment for a metabolic disorder, has completed treatment for a metabolic disorder, and/or is in remission from a metabolic disorder in between the first point in time and the subsequent point in time. In another embodiment, the cell type is selected from the group consisting of: preadipocytes, mature white adipocytes, brown adipocytes, monocytes, and macrophages. In still another embodiment, the first and/or at least one subsequent sample is selected from the group consisting of ex vivo and in vivo samples. In yet another embodiment, the first and/or at least one subsequent sample is obtained from an animal model of a metabolic disorder. In another embodiment, the first and/or at least one subsequent sample is selected from the group consisting of tissue, whole blood, serum, plasma, buccal scrape, saliva, cerebrospinal fluid, urine, stool, and bone marrow. In still another embodiment, the first and/or at least one subsequent sample is a portion of a single sample obtained from the subject. In yet another embodiment, the first and/or at least one subsequent sample is a portion of pooled samples obtained from the subject. In another embodiment, the method further comprises performing steps a) and b) with rosiglitazone, for example, to use the treatment with rosiglitazone to compare with the results from the test compound. In still another embodiment, a significantly higher amount and/or activity comprises upregulating the amount and/or activity of the marker listed in Table 1 at least 25% relative to the second sample. In yet another embodiment, a significantly lower amount and/or activity comprises downregulating the amount and/or activity of the marker listed in Table 2 at least 25% relative to the second sample. In still another embodiment, the amount of the marker is compared, for example, wherein the amount of the marker is determined by determining the level of protein expression of the marker (e.g., using a reagent which specifically binds with the protein such as an antibody, an antibody derivative, and an antibody fragment, such as an antibody that binds to PPAR-gamma and an antibody that binds to a peptide comprising a consensus cdk5 phosphorylated site). In yet another embodiment, the level of expression of the marker in the sample is assessed by detecting the presence in the sample of a transcribed polynucleotide or portion thereof (e.g., mRNA or a cDNA and/or further comprising amplifying the transcribed polynucleotide.) or is assessed by detecting the presence in the sample of a transcribed polynucleotide which anneals with the marker or anneals with a portion of a polynucleotide under stringent hybridization conditions. In another embodiment, the marker is phosphorylated Ser-273 on murine PPAR gamma 2 or a corresponding serine residue in a murine PPAR gamma 2 homolog. In still another embodiment, the metabolic disorder is selected from the group consisting of: glucose intolerance, insulin resistance, hypertension, dyslipidemia, obesity, type II diabetes, hyperglycemia, hyperinsulinemia, elevated systolic and diastolic blood pressure, hypertrigliceridemia, hypercholesterolemia, and body mass index greater than 30. In yet another embodiment, PPAR gamma comprises the amino acid sequence set forth in SEQ ID NO:1-7. In some embodiments, the methods for assessing the efficacy of a compound that binds PPAR gamma for selectively promoting anti-metabolic disorder activity over classical PPAR gamma activation in a subject can also be used to assess the efficacy of a compound that binds PPAR gamma for promoting anti-metabolic disorder over a control. Accordingly, such controls can include, for example, samples not exposed to the control and/or exposed to the compound at different doses, time intervals, and similar variables. Such methods enable clinicians to better stratify a given subject for monitoring and/or therapeutic intervention, either with drug therapy or with other modalities.

In yet another aspect, methods are provided for treating a subject afflicted with a metabolic disease comprising administering to the subject a compound that binds PPAR gamma and which selectively promotes anti-diabetic activity, thereby treating the subject afflicted with the metabolic disease. In one embodiment, the compound inhibits Ser-273 phosphorylation of murine PPAR gamma 2 or a corresponding serine residue in a murine PPAR gamma 2 homolog. In another embodiment, the compound is administered in a pharmaceutically acceptable formulation. In still another embodiment, the pharmaceutically acceptable formulation is an oral formulation. In yet another embodiment, the compound is a small molecule.

In another aspect, compounds are provided for treating a metabolic disorder (e.g., diabetes and/or obesity) selectively promoting anti-metabolic disorder activity in a cell type, wherein the compound inhibits phosphorylation of Ser-273 on PPAR gamma. In one embodiment, the compound has less than 30% of the PPAR gamma agonist function of rosiglitazone. In another embodiment, the compound has an EC50 binding affinity for PPAR gamma less than 1-200 nM. In still another embodiment, the compound upregulates expression of a marker listed in Table 1 at least 30% relative to rosiglitazone under identical conditions and/or downregulates expression of a marker listed in Table 2 at least 30% relative to rosiglitazone under identical conditions. In yet another embodiment, the metabolic disorder is selected from the group consisting of: glucose intolerance, insulin resistance, hypertension, dyslipidemia, obesity, type II diabetes, hyperglycemia, hyperinsulinemia, elevated systolic and diastolic blood pressure, hypertrigliceridemia, hypercholesterolemia, and body mass index greater than 30.

In still another aspect, isolated nucleic acid molecules are provided encoding a murine peroxisome proliferator activated receptor gamma 2 polypeptide having a non-phosphorylatable amino acid at position Ser-273 or a homolog thereof having a non-phosphorylatable amino acid at the corresponding serine residue position in the murine PPAR gamma 2 polypeptide, or a complement thereof. In one embodiment, the isolated isolated nucleic acid molecules encode a polypeptide having the amino acid sequence set forth in SEQ ID NO:2 or 3, and further encoding a non-phosphorylatable amino acid at position Ser-273, or a complement thereof. In another embodiment, the isolated nucleic acid molecules further encode a heterologous polypeptide.

In yet another aspect, vectors (e.g., expression vectors) are provided comprising the nucleic acid molecules of the invention and host cells are also provided comprising the vectors of the invention.

In another aspect, methods are provided for producing a protein comprising culturing host cell of the invention in a suitable medium until the protein is produced. In one embodiment, the produced proteins are further isolated from the medium or the host cell.

In still another aspect, isolated proteins are provided comprising a murine peroxisome proliferator activated receptor gamma 2 polypeptide having a non-phosphorylatable amino acid at position Ser-273 or a homolog thereof having a non-phosphorylatable amino acid at the corresponding serine residue position in the murine PPAR gamma 2 polypeptide. In one embodiment, the isolated protein comprises a polypeptide having the amino acid sequence set forth in SEQ ID NO:2 or 3, and further encoding a non-phosphorylatable amino acid at position Ser-273. In another embodiment, the isolated protein is operatively linked to a heterologous polypeptide.

In yet another aspect, methods are provided for making an isolated hybridoma which produces an antibody that specifically binds to murine PPAR gamma 2 phosphorylated at Ser-273 or a corresponding serine residue in a murine PPAR gamma 2 homolog or a fragment thereof, the method comprising immunizing a mammal using a composition comprising said murine PPAR gamma 2 phosphorylated at Ser-273 or a corresponding serine residue in a murine PPAR gamma 2 homolog or a fragment thereof, isolating splenocytes from the immunized mammal, fusing the isolated splenocytes with an immortalized cell line to form hybridomas, and screening individual hybridomas for production of an antibody which specifically binds with said polypeptide thereof to isolate the hybridoma.

In another aspect, antibodies produced by a hybridoma of the invention are provided.

In still another aspect, isolated antibodies or antigen binding portions thereof are provided that specifically bind to a polypeptide comprising the amino acid sequence of a murine PPAR gamma 2 phosphorylated at Ser-273 or a corresponding serine residue in a murine PPAR gamma 2 homolog or a fragment thereof. In one embodiment, the antibody or antigen binding portion thereof specifically binds the epitope having the amino acid sequence, KTTDK (pS)PFVIYDC (SEQ ID NO: 14). In another embodiment, the antibody or antigen binding portion thereof is a monoclonal, polyclonal, chimeric, or a humanized, antibody. In still another embodiment, the antibody or antigen binding portion thereof is detectably labeled. In yet another embodiment, the antibody or antigen binding portion thereof comprises an effector domain, an Fc domain, is a single-chain antibody, or is a Fab fragment.

In yet another aspect, kits are provided for assessing the ability of a compound to inhibit phosphorylation of PPAR gamma comprising one or more reagents for specifically detecting murine PPAR gamma 2 phosphorylated at Ser-273 or a corresponding serine residue in a murine PPAR gamma 2 homolog.

In another aspect, non-human animal models are provided comprising a mutated PPAR gamma 2 gene encoding a protein incapable of being phosphorylated at serine 273 or a corresponding serine residue in a murine PPAR gamma 2 homolog. In one embodiment, the mutation comprises a mutation of said serine to a non-phosphorylatable amino acid, such as alanine. In another embodiment, the non-human animal model is heterozygous or homozygous for the mutated PPAR gamma 2 gene encoding a protein incapable of being phosphorylated at serine 273 or a corresponding serine residue in a murine PPAR gamma 2 homolog. In another embodiment, the non-human animal model is a knock-in or a transgenic animal. In still another embodiment, the non-human animal model is a rodent and/or a mouse.

In still another aspect, methods are provided for identifying genes regulated in a subject, comprising expressing a mutated PPAR gamma gene encoding a protein incapable of being phosphorylated on Serine 273 or a corresponding serine residue in a murine PPAR gamma 2 homolog, determining the level of expression and/or activity of one or more candidate target genes of said mutated PPAR gamma gene, and identifying genes which exhibit significantly altered expression and/or activity relative to a control.

In yet another aspect, methods are provided for classifying a sample according to a predicted treatment outcome comprising comparing the level of expression of a marker or a plurality of markers in a biological sample and the level of expression of the marker or plurality of markers in a control sample, wherein the marker or plurality of markers are selected from the group consisting of the markers listed in Tables 1 and 2 (e.g., phosphorylated Ser-273-PPAR gamma or homolog thereof) and the difference between the level of expression of the marker or plurality of markers in the biological sample and the control sample classifies the biological sample according to the predicted treatment outcome. In one embodiment, the predicted treatment outcome is selected from the treatment outcomes listed in Tables 1 and 2, such as increased insulin sensitivity. In another embodiment, the biological sample is obtained after a PPAR gamma ligand as been administered to the subject from which the biological sample was obtained.

In another aspect, methods are provided for identifying a subject likely to have a predicted treatment outcome comprising comparing the level of expression of a marker or a plurality of markers in a biological sample from the subject and the level of expression of the marker or plurality of markers in a control sample, wherein the marker or plurality of markers are selected from the group consisting of the markers listed in Tables 1 and 2 and the difference between the level of expression of the marker or plurality of markers in the biological samples from the subject and the control sample predicts the likelihood of a predicted treatment outcome in the subject. In one embodiment, the predicted treatment outcome is selected from the treatment outcomes listed in Tables 1 and 2, such as increased insulin sensitivity. In another embodiment, the biological sample is obtained after a PPAR gamma ligand as been administered to the subject.

It will also be understood that certain embodiments of the present invention can be used with more than one method, composition, kit, etc. described herein, according to knowledge available to the skilled artisan.

BRIEF DESCRIPTION OF FIGURES

FIG. 1A shows conservation of phosphorylated serine residues of PPAR gamma polypeptides across numerous species (SEQ ID NOS 83-92, respectively, in order of appearance). FIG. 1B shows results of in vitro CDK kinase assays performed using cdk5/p35 or the indicated cdks/cyclins CDK5/p35 with either wild type (WT) or S273A mutated PPAR. Histone H1 or Rb were used as a positive controls. FIG. 1C shows cdk5-mediated phosphorylation of PPAR gamma in HEK293 cells following co-expression of PPAR gamma with either wild type or kinase inactive mutant (KD) of CDK5; IP, immunoprecipitate; IB, immunoblot. FIG. 1D shows that CDK5 phosphorylated PPAR gamma, but not PPAR alpha or PPAR delta isoforms.

FIG. 2A shows the results of treating differentiated 3T3-L1 cells with TNF-α, IL-6, or FFAs for the indicated times. Phosphorylation of PPAR gamma was detected using a phospho-S273 PPAR gamma antibody. FIG. 2B shows the results of Western blot analyses of PPAR gamma phosphorylation in differentiated 3T3-L1 adipocytes expressing scrambled or CDK5 shRNA. FIG. 2C shows the results of cells expressing scrambled or CDK5 shRNA stimulated with the indicated cytokines and analyzed with phospho-S273 PPAR gamma antibody. NT, no treatment.

FIG. 3A shows transcriptional activity of a PPAR-derived reporter gene in response to wild type or S273A mutant of PPAR gamma/RXRα in HEK-293 cells (±10 µM rosiglitazone) (n=3). FIG. 3B shows the results of PPAR gamma-null fibroblasts expressing retroviral wild type or S273A mutant PPAR gamma stained with Oil-Red-O 7 days after adipocyte differentiation. Expression of PPAR gamma was analyzed with an anti-PPAR gamma antibody. FIG. 3C shows the results of gene expression in these cells by real-time quantitative PCR (qPCR) for expression of various genes (n=3). FIG. 3D shows secreted adiponectin levels in cultured medium (n=3). FIG. 3E shows mRNA expression in transplanted fat pads as analyzed by real-time qPCR (n=5). Error bars are s.e.m.; * p<0.05; ** p<0.01).

FIG. 4A shows results of white adipose tissue (epididymal) from mice on HFD for the indicated time analyzed with phospho-S273 PPAR gamma, PPAR gamma, phospho-Y15 CDK5, CDK5 and p35 antibodies. FIG. 4B shows the results of selected metabolic parameters in mice fed chow or HFD. Results of body weights, glucose and insulin levels in C57BL/6J mice (n=6) on chow or HFD for 7- or 13-weeks after an overnight fast are shown (error bars are s.e.m.;  p<0.01; * p<0.001). FIG. 4C shows the results of epididymal (Epi.) or inguinal (Ing.) fat tissue from 13 weeks HFD mice analyzed with phospho-S273 antibody.

FIG. 5A shows the results of TNF-α-induced phosphorylation of PPAR gamma in 3T3-L1 adipocytes expressing either wild type or Q286P mutant of PPAR gamma treated as indicated with rosiglitazone and/or GW9662. FIG. 5B shows the results of an in vitro CDK5 kinase assay with CDK5/p35 and PPAR gamma incubated with either rosiglitazone or MRL24 and the indicated concentrations. FIG. 5C shows transcriptional activity of a PPAR-derived reporter gene in response to rosiglitazone or MRL24 in HEK-293 cells (n=3; error bars are s.e.m.). FIG. 5D shows the results of an in vitro kinase assay using CDK5/p35 and either Rb or PPAr gamma with rosiglitazone or MRL24. FIG. 5E shows TNF-α-induced phosphorylation of PPAR gamma in HEK-293 cells with rosiglitazone or MRL24 at the indicated concentrations. FIG. 5F shows the results of microarray analyses of differentiated PPAr gamma-null fibroblasts expressing wild type (NT, no treatment; rosiglitazone, or MRL24 treated) or S273A mutant PPAR gamma (n=3).

FIG. 6A shows results of in vitro CDK5 kinase assays performed using purified CDK5/p35 and PPAR gamma with different PPAR gamma ligands (rosiglitazone, Mbx-102, BVT.13, nTZDpa or MRL24) at the indicated concentrations. Phosphorylation of PPAR gamma, total PPAR gamma and CDK5 were detected by Western blotting. FIG. 6B shows structural diversity of numerous atypical PPAR gamma agonists. FIG. 6C shows that numerous atypical PPAR gamma agonists have very weak agonist activity on a PPAR transcriptional response element.

FIG. 8A shows histograms indicating the percent reduction in HDX for each peptide region. Values are calculated relative to the measured % D value for apo PPAR gamma-LBD (n=4; error bars are s.e.m.). FIG. 8B shows HDX data for the four peptides of interest plotted over the structures of PPAR gamma-LBD bound with rosiglitazone (left, PDB:2PRG) and MRL24 (right, PDB:2Q5P). Percent reduction in HDX relative to apo receptor is colored according to the key.

FIG. 9A shows the results of glucose-tolerance tests in 16-week HFD mice treated with vehicle, rosiglitazone or MRL24 (n=10). Fasting insulin levels (FIG. 9B) and body weight (FIG. 9C) of these mice are shown. FIG. 9D shows results of phosphorylation of PPAR gamma in WAT from these mice analyzed using a phospho-S273 antibody. FIG. 9E shows real-time qPCR results of WAT from these mice analyzed for the expression of gene sets regulated by PPAR gamma phosphorylation (Error bars are s.e.m.; * p<0.05;  p<0.01;* p<0.001).

FIG. 14A shows the results of pPPAR gamma/PPAR gamma in percentage terms before and after the rosiglitazone treatment regimen. FIG. 14B shows the correlation of insulin sensitivity in the subjects with the percentage change in the pPPAR gamma/PPAR gamma ratio due to the rosiglitazone treatment. FIG. 14C provides quantitative data.

BRIEF DESCRIPTION OF THE TABLES

Figure 1:
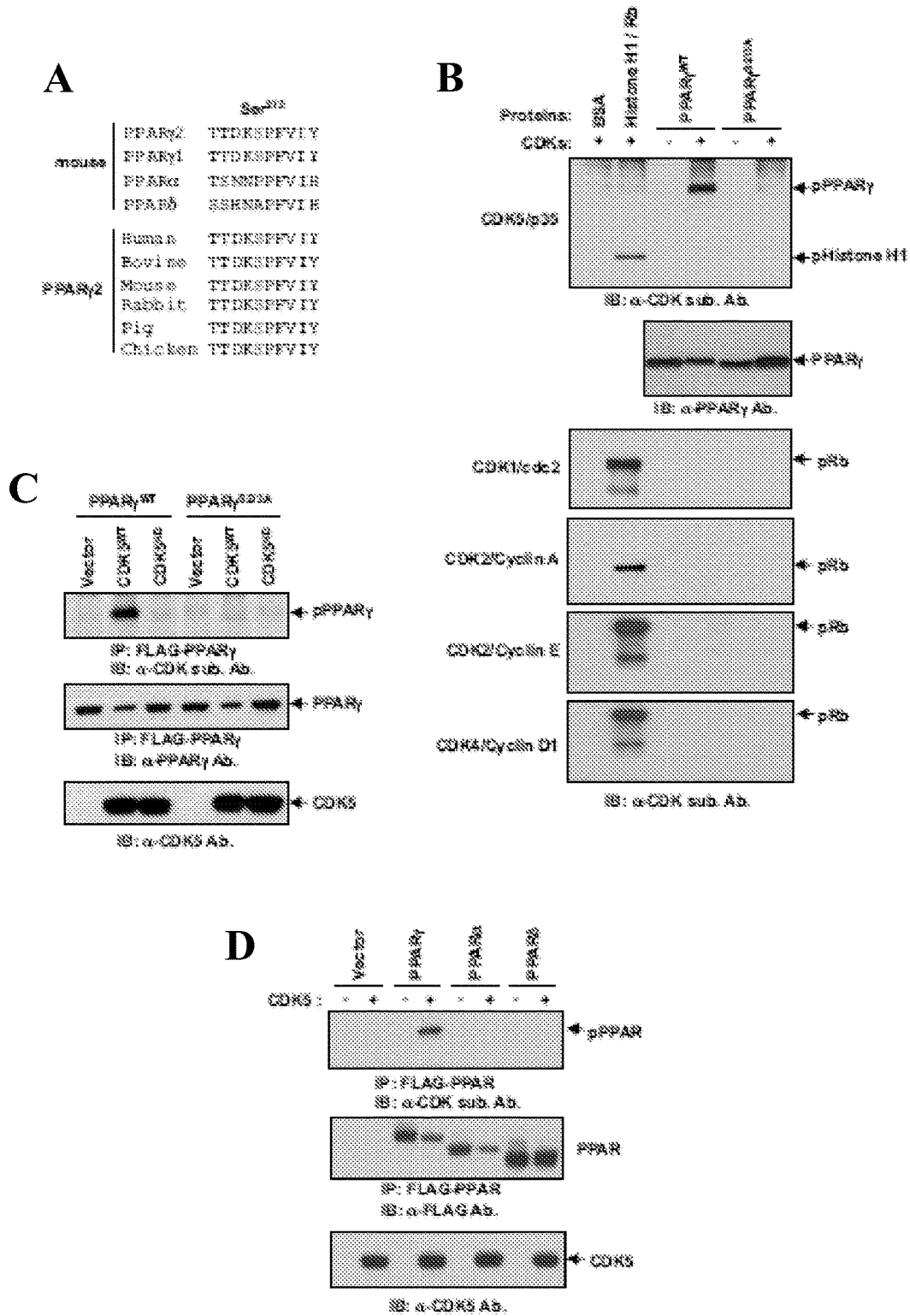
FIGS. 1A-1D depict results of cdk5-specific phosphorylation of serine 273 on murine PPAR gamma 2.

Table 1 is a listing of exemplary genes, activities and assays whose expression and/or activity is increased relative to a control.

Table 2 is a listing of exemplary genes, activities, and assays whose expression and/or activity is decreased relative to a control.

Table 3 is a listing of exemplary primer sequences useful for quantifying expression levels of markers of the present invention.

DETAILED DESCRIPTION OF THE INVENTION

In order that the present invention may be more readily understood, certain terms are first defined. Additional definitions are set forth throughout the detailed description.

The articles "a" and "an" are used herein to refer to one or to more than one (i.e., to at least one) of the grammatical object of the article. By way of example, "an element" means one element or more than one element.

The term "altered amount" of a biomarker or "altered level" of a biomarker refers to increased or decreased expression and/or activity of a biomarker of the present invention, at least in part, (e.g., the markers set forth in Tables 1 and 2) in a sample as compared to that in a control sample. The term "altered amount" of a biomarker also includes an increased or decreased protein level of a biomarker in a sample as compared to the protein level of the biomarker in a normal, control sample.

The term "altered level of expression" of biomarkers of the present invention, at least in part, (e.g., biomarkers set forth in Tables 1 and 2) refers to an expression level or copy number of a biomarker in a test sample such as a sample derived from a subject suffering from a metabolic disorder (e.g., diabetes and/or obesity), that is greater or less than the standard error of the assay employed to assess expression or copy number, and may be at least twice, at least twice three, at least twice four, at least twice five, or at least twice ten or more times the expression level or copy number of the biomarkers of the present invention, at least in part, (e.g., biomarkers set forth in Tables 1 and 2) in a control sample (e.g., a sample from a healthy subject not having the associated disease), or the average expression level or copy number of the biomarkers of the present invention, at least in part, (e.g., biomarkers set forth in Tables 1 and 2) in several control samples. The altered level of expression is greater or less than the standard error of the assay employed to assess expression or copy number, and is at least twice, at least three, at least four, at least five, at least ten or more times the expression level or copy number of the biomarkers of the present invention, at least in part, (e.g., biomarkers set forth in Tables 1 and 2) in a control sample (e.g., a sample from a healthy subject not having the associated disease), or the average expression level or copy number of the biomarkers of the present invention, at least in part, (e.g., biomarkers set forth in Tables 1 and 2) in several control samples.

The term "altered activity" of a biomarker refers to an activity of a biomarker which is increased or decreased in a disease state, e.g., in a metabolic disorder (e.g., diabetes and/or obesity) sample, as compared to the activity of the biomarker in a normal, control sample. Altered activity of a biomarker may be the result of, for example, altered expression of the biomarker, altered protein level of the biomarker, altered structure of the biomarker, or, e.g., an altered interaction with other proteins involved in the same or different pathway as the biomarker. Biological activities, as described herein, may include subject responses as set forth in this application, as measured by gene expression changes and/or assays listed in Tables 1 and 2.

The term "altered structure" of a biomarker refers to the presence of mutations or mutations within the biomarker gene or maker protein, e.g., mutations which affect expression or activity of the biomarker, as compared to the normal or wild-type gene or protein. For example, mutations include, but are not limited to inter- and intra-chromosomal rearrangement, substitutions, deletions, and insertion mutations. Mutations may be present in the coding or non-coding region of the biomarker.

"Binding compound" shall refer to a binding composition, such as a small molecule, an antibody, a peptide, a peptide or non-peptide ligand, a protein, an oligonucleotide, an oligonucleotide analog, such as a peptide nucleic acid, a lectin, or any other molecular entity that is capable of specifically binding to a target protein or molecule or stable complex formation with an analyte of interest, such as a complex of proteins.

"Binding moiety" means any molecule to which molecular tags can be directly or indirectly attached that is capable of specifically binding to an analyte. Binding moieties include, but are not limited to, antibodies, antibody binding compositions, peptides, proteins, nucleic acids and organic molecules having a molecular weight of up to about 1000 daltons and containing atoms selected from the group consisting of hydrogen, carbon, oxygen, nitrogen, sulfur and phosphorus.

A "biomarker" or "marker" is a gene, mRNA, or protein which may be altered, wherein said alteration is associated with a metabolic disorder (e.g., diabetes and/or obesity). The alteration may be in amount, structure, and/or activity in a metabolic disorder (e.g., diabetes and/or obesity) tissue or a metabolic disorder (e.g., diabetes and/or obesity) cell, as compared to its amount, structure, and/or activity, in a normal or healthy tissue or cell (e.g., a control), and is associated with a disease state, such as a metabolic disorder (e.g., diabetes and/or obesity). For example, a biomarker of the present invention, at least in part, which is associated with a metabolic disorder (e.g., diabetes and/or obesity) or predictive of responsiveness to anti-a metabolic disorder (e.g., diabetes and/or obesity) therapeutics may have an altered nucleotide sequence, amino acid sequence, chromosomal translocation, intra-chromosomal inversion, copy number, expression level, protein level, protein activity, or methylation status, in a metabolic disorder (e.g., diabetes and/or obesity) tissue or a metabolic disorder (e.g., diabetes and/or obesity) cell as compared to a normal, healthy tissue or cell. Furthermore, a "biomarker" includes a molecule whose structure is altered, e.g., mutated (contains an mutation), e.g., differs from the wild type sequence at the nucleotide or amino acid level, e.g., by substitution, deletion, or insertion, when present in a tissue or cell associated with a disease state, such as a metabolic disorder (e.g., diabetes and/or obesity). In some embodiments, the biomarkers of the present invention, at least in part, are selected from the group of biomarkers listed in Tables 1 and 2.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In certain embodiments, the first region comprises a first portion and the second region comprises a second portion, whereby, when the first and second portions are arranged in an antiparallel fashion, at least about 50%, at least about 75%, at least about 90%, or at least about 95% of the nucleotide residues of the first portion are capable of base pairing with nucleotide residues in the second portion. In other embodiments, all nucleotide residues of the first portion are capable of base pairing with nucleotide residues in the second portion.

The "copy number of a gene" or the "copy number of a biomarker" refers to the number of DNA sequences in a cell encoding a particular gene product. Generally, for a given gene, a mammal has two copies of each gene. The copy number can be increased, however, by gene amplification or duplication, or reduced by deletion.

As used herein, the term "diabetes" refers to a number of well-known conditions. Insulin resistance is defined as a state in which circulating insulin levels in excess of the normal response to a glucose load are required to maintain the euglycemic state (Ford E S, et al. JAMA. (2002) 287:356-9). Insulin resistance, and the response of a subject with insulin resistance to therapy, may be quantified by assessing the homeostasis model assessment to insulin resistance (HOMA-IR) score, a reliable indicator of insulin resistance (Katsuki A, et al. Diabetes Care 2001; 24:362-5). The estimate of insulin resistance by the homeostasis assessment model (HOMA)-IR score is calculated with the formula (Galvin P, et al. Diabet Med 1992; 9:921-8): HOMA-IR=[fasting serum insulin ($\mu$U/mL)]×[fasting plasma glucose (mmol/L)/22.5]. Subjects with a predisposition for the development of impaired glucose tolerance (IGT) or type 2 diabetes are those having euglycemia with hyperinsulinemia are by definition, insulin resistant. A typical subject with insulin resistance is usually overweight or obese. The term "pre-diabetes" is the condition wherein an individual is pre-disposed to the development of type 2 diabetes. Pre-diabetes extends the definition of impaired glucose tolerance to include individuals with a fasting blood glucose within the high normal range 100 mg/dL (J. B. Meigs, et al. Diabetes 2003; 52:1475-1484) and fasting hyperinsulinemia (elevated plasma insulin concentration). The scientific and medical basis for identifying pre-diabetes as a serious health threat is laid out in a Position Statement entitled "The Prevention or Delay of Type 2 Diabetes" issued jointly by the American Diabetes Association and the National Institute of Diabetes and Digestive and Kidney Diseases (Diabetes Care 2002; 25:742-749). Individuals likely to have insulin resistance are those who have two or more of the following attributes: 1) overweight or obese, 2) high blood pressure, 3) hyperlipidemia, 4) one or more 1.sup.st degree relative with a diagnosis of IGT or type 2 diabetes. Insulin resistance can be confirmed in these individuals by calculating HOMA-IR score. For the purpose of this invention, insulin resistance is defined as the clinical condition in which an individual has a HOMA-IR score>4.0 or a HOMA-IR score above the upper limit of normal as defined for the laboratory performing the glucose and insulin assays. Type 2 diabetes is defined as the condition in which a subject has a fasting blood glucose or serum glucose concentration greater than 125 mg/dl (6.94 mmol/L).

A biomarker is "fixed" to a substrate if it is covalently or non-covalently associated with the substrate such that the substrate can be rinsed with a fluid (e.g., standard saline citrate, pH 7.4) without a substantial fraction of the biomarker dissociating from the substrate.

"Hazard ratio", as used herein, refers to a statistical method used to generate an estimate for relative risk. "Hazard ratio" is the ratio between the predicted hazard of one group versus another group. For example, subject populations treated with a PPAR gamma ligand versus without a PPAR gamma ligand can be assessed for whether or not the PPAR gamma ligand is effective in treating a metabolic disorder (e.g., diabetes and/or obesity), particularly with regard to PPAR gamma phosphorylation status on serine 273.

The terms "homology" or "identity," as used interchangeably herein, refer to sequence similarity between two polynucleotide sequences or between two polypeptide sequences, with identity being a more strict comparison. The phrases "percent identity or homology" and "% identity or homology" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar, or any integer value there between. Identity or similarity can be determined by comparing a position in each sequence that may be aligned for purposes of comparison. When a position in the compared sequence is occupied by the same nucleotide base or amino acid, then the molecules are identical at that position. A degree of similarity or identity between polynucleotide sequences is a function of the number of identical or matching nucleotides at positions shared by the polynucleotide sequences. A degree of identity of polypeptide sequences is a function of the number of identical amino acids at positions shared by the polypeptide sequences. A degree of homology or similarity of polypeptide sequences is a function of the number of amino acids at positions shared by the polypeptide sequences. The term "substantial homology," as used herein, refers to homology of at least 50%, at least 60%, at least 65%, at least 70%, at least 75%, at least 80%, at least 85%, at least 90%, at least 95% or more.

"Likely to," as used herein, refers to an increased probability, that an item, object, thing or person will occur such as at least 5%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200%, or more (or any range inclusive). Thus, in one example, a subject that is likely to respond to treatment with the PPAR gamma ligands of the present invention, at least in part, has an increased probability of responding to treatment with the PPAR gamma ligand such that an anti-metabolic disorder activity is selectively promoted over classical PPAR gamma activation relative to a reference subject or group of subjects.

The terms "metabolic disorder" and "obesity related disorders" are used interchangeably herein and include a disorder, disease or condition which is caused or characterized by an abnormal metabolism (i.e., the chemical changes in living cells by which energy is provided for vital processes and activities) in a subject. Metabolic disorders include diseases, disorders, or conditions associated with aberrant thermogenesis or aberrant adipose cell (e.g., brown or white adipose cell) content or function. Metabolic disorders can be characterized by a misregulation (e.g., downregulation or upregulation) of expression, structure, and/or expression of one or more biomarkers (including fragments thereof) and/or assays listed in Tables 1 and 2. Metabolic disorders can detrimentally affect cellular functions such as cellular proliferation, growth, differentiation, or migration, cellular regulation of homeostasis, inter- or intra-cellular communication; tissue function, such as liver function, muscle function, or adipocyte function; systemic responses in an organism, such as hormonal responses (e.g., insulin response).

Examples of metabolic disorders include obesity, including insulin resistant obesity, diabetes, noninsulin dependent diabetes mellitus (NIDDM or Type H diabetes), insulin dependent diabetes mellitus (IDDM or Type I diabetes), type II diabetes, insulin resistance such as impaired glucose tolerance, glucose intolerance, atherosclerosis, atheromatous disease, heart disease, hypertension, stroke, Syndrome X, hyperphagia, endocrine abnormalities, triglyceride storage disease, Bardet-Biedl syndrome, Lawrence-Moon syndrome, Prader-Labhart-Willi syndrome, Werner's syndrome, dysfunctions associated with lipid biosynthesis, lipid transport, triglyceride levels, plasma levels, and plasma cholesterol, dyslipidemias associated with hyperlipidemia, elevated free fatty acids, hypercholesterolemia, hypertriglyceridemia, elevated low density lipoprotein-(LDL)-cholesterol, elevated very low density lipoprotein-(VLDL)-cholesterol, elevated intermediate density lipoprotein-(IDL)-cholesterol, or reduced high density lipoprotein-(HDL)-cholesterol. A metabolic disorder (e.g., diabetes and/or obesity) is "inhibited" if at least one symptom of the metabolic disorder (e.g., diabetes and/or obesity) is alleviated, terminated, slowed, or prevented. As used herein, a metabolic disorder (e.g., diabetes and/or obesity) is also "inhibited" if recurrence or metastasis of the metabolic disorder (e.g., diabetes and/or obesity) is reduced, slowed, delayed, or prevented.

In addition, metabolic disorders are associated with one or more discrete phenotypes. For example, body mass index (BMI) of a subject is defined as the weight in kilograms divided by the square of the height in meters, such that BMI has units of $kg/m^2$. Overweight is defined as the condition wherein the individual has a BMI greater than or 25 $kg/m^2$ and less than 30 $kg/m^2$. In some embodiments, obesity is defined as the condition wherein the individual has a BMI equal to or greater than 30 $kg/m^2$. In another aspect, the term obesity is used to mean visceral obesity which can be defined in some embodiments as a waist-to-hip ratio of 1.0 in men and 0.8 in women, which, in another aspect defines the risk for insulin resistance and the development of pre-diabetes. Euglycemia is defined as the condition in which a subject has a fasting blood glucose concentration within the normal range, greater than 70 mg/dl (3.89 mmol/L) and less than 110 mg/dl (6.11 mmol/L). The word fasting has the usual meaning as a medical term. Impaired glucose tolerance (IGT), is defined as the condition in which a subject has a fasting blood glucose concentration or fasting serum glucose concentration greater than 110 mg/dl and less than 126 mg/dl (7.00 mmol/L), or a 2 hour postprandial blood glucose or serum glucose concentration greater than 140 mg/dl (7.78 mmol/L) and less than 200 mg/dl (11.11 mmol/L). The term impaired glucose tolerance is also intended to apply to the condition of impaired fasting glucose. Hyperinsulinemia is defined as the condition in which a subject with insulin resistance, with or without euglycemia, in which the fasting or postprandial serum or plasma insulin concentration is elevated above that of normal, lean individuals without insulin resistance, having a waist-to-hip ration<1.0 (for men) or <0.8 (for women). The terms "diabetes", "prediabetes", and "insulin-sensitizing", "insulin resistance-improving" or "insulin resistance-lowering" (used interchangeably herein) have been described herein.

As used herein, "metabolic syndrome" refers to a condition present when more than one of these factors are present in a single individual. The factors include: central obesity (disproportionate fat tissue in and around the abdomen), atherogenic dyslipidemia (these include a family of blood fat disorders including, e.g., high triglycerides, low HDL cholesterol, and high LDL cholesterol that can foster plaque buildups in the vascular system, including artery walls), high blood pressure (130/85 mmHg or higher), insulin resistance or glucose intolerance (the inability to properly use insulin or blood sugar), a chronic prothrombotic state (e.g., characterized by high fibrinogen or plasminogen activator inhibitor [−1] levels in the blood), and a chronic proinflammatory state (e.g., characterized by higher than normal levels of high-sensitivity C-reactive protein in the blood). In some embodiments, the "Third Report of the National Cholesterol Education Program (NCEP) Expert Panel on Detection, Evaluation, and Treatment of High Blood Cholesterol in Adults (Adult Treatment Panel III)" may be used in the diagnosis of a metabolic disorder. Under the NCEP criteria, metabolic syndrome can be clinically identified by the presence of three or more of the following components in a single subject: (1) central obesity, as measured by waist circumference (women with a waist circumference greater than 35 inches; for men greater than 40 inches); (2) fasting blood triglycerides greater than or equal to 150 mg/dL; (3) blood HDL cholesterol (for women less than 50 mg/dL, for men less than 40 mg/dL); (4) blood pressure greater than or equal to 130/85 mmHg; and (5) fasting glucose greater than or equal to 110 mg/dL. Other features such as insulin resistance (e.g., increased fasting blood insulin), prothrombotic state or proinflammatory state are not generally required for clinical diagnosis, though they are certainly also indicative of metabolic syndrome and follow-up studies on these attributes can be used to further confirm diagnosis of metabolic syndrome. For example, insulin resistance, even in the absence of the NCEP criteria, is often indicative of metabolic syndrome.

A biomarker "nucleic acid" is a nucleic acid (e.g., DNA, mRNA, cDNA) encoded by or corresponding to a biomarker of the present invention, at least in part. For example, such biomarker nucleic acid molecules include DNA (e.g., genomic DNA and cDNA) comprising the entire or a partial sequence of any of the nucleic acid sequences set forth in Tables 1 and 2 or the complement or hybridizing fragment of such a sequence. The biomarker nucleic acid molecules also include RNA comprising the entire or a partial sequence of any of the nucleic acid sequences set forth in Tables 1 and 2 or the complement of such a sequence, wherein all thymidine residues are replaced with uridine residues. A "biomarker protein" is a protein encoded by or corresponding to a biomarker of the present invention, at least in part. A biomarker protein comprises the entire or a partial sequence of a protein encoded by any of the sequences set forth in Tables 1 and 2 or a fragment thereof. The terms "protein" and "polypeptide" are used interchangeably herein.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (for example, illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid. In addition, a skilled artisan will understand how to mutate nucleotides of a specific codon so as to specifically alter an encoded amino acid based on the relevant codon chart.

The "normal" copy number of a biomarker or "normal" level of expression of a biomarker is the level of expression, copy number of the biomarker, in a biological sample, e.g., a sample containing tissue, whole blood, serum, plasma, buccal scrape, saliva, cerebrospinal fluid, urine, stool, and bone marrow, from a subject, e.g., a human, not afflicted with a metabolic disorder (e.g., diabetes and/or obesity).

As used herein, "obesity" refers to a body mass index (BMI) of 30 kg/$^2$m or more (National Institute of Health, Clinical Guidelines on the Identification, Evaluation, and Treatment of Overweight and Obesity in Adults (1998)). However, the present invention, at least in part, is also intended to include a disease, disorder, or condition that is characterized by a body mass index (BMI) of 25 kg/$^2$m or more, 26 kg/$^2$m or more, 27 kg/$^2$m or more, 28 kg/$^2$m or more, 29 kg/$^2$m or more, 29.5 kg/$^2$m or more, or 29.9 kg/$^2$m or more, all of which are typically referred to as overweight (National Institute of Health, Clinical Guidelines on the Identification, Evaluation, and Treatment of Overweight and Obesity in Adults (1998)). The obesity described herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetics, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia. "Prevention of obesity" refers to preventing obesity or an obesity related disorder from occurring if the treatment is administered prior to the onset of the obese condition. Moreover, if treatment is commenced in subjects already suffering from or having symptoms of obesity or an obesity related disorder, such treatment is expected to prevent, or to prevent the progression of obesity or the obesity related disorder, and the medical sequalae of obesity, such as, e.g., arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis. "Treatment of obesity" refers to reducing the BMI of the mammal to less than about 25.9, and maintaining that weight for a period of time, e.g., for at least about 6 months. The treatment suitably results in an increase in metabolic activity.

An "overexpression" or "significantly higher level of expression, copy number, and/or activity" of biomarkers of the present invention, at least in part, (e.g., biomarkers set forth in Tables 1 and 2) refers to an expression level, copy number, and/or activity in a test sample that is greater than the standard error of the assay employed to assess expression or copy number, and may be at least two, at least three, at least four, at least five, or at least ten or more times the expression level or copy number of the biomarkers of the present invention, at least in part, (e.g., biomarkers set forth in Tables 1 and 2) in a control sample (e.g., a sample from a healthy subject not afflicted with a metabolic disorder (e.g., diabetes and/or obesity)), or the average expression level or copy number of the biomarkers of the present invention, at least in part, (e.g., biomarkers set forth in Tables 1 and 2) in several control samples.

The term "probe" refers to any molecule which is capable of selectively binding to a specifically intended target molecule, for example a biomarker of the present invention, at least in part. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic monomers.

As used herein, "PPAR gamma" refers to a member of the well known family, of the nuclear receptors. In addition, "Serine 273" or "phosphorylated Serine 273" of PPAR gamma refers to the amino acid numbering of the mouse PPAR gamma polypeptide from the N-terminus. Accordingly, a skilled artisan will readily understand that serine 273 of the mouse PAR gamma polypeptide is conserved across numerous species and that the compositions and methods of the present invention apply equally well to the serine residues of isoforms, homologs, and orthologs in other species corresponding to said serine 273, including, for example, humans. For example, representative PPAR gamma species, as opposed to other members of the PPAR nuclear receptor superfamily (such as PPAR alpha and PPAR delta) are provided herein as follows:

```
Mouse PPAR gamma 1
                                                          (SEQ ID NO: 1)
MVDTEMPFWPTNFGISSVDLSVMEDHSHSFDIKPFTTVDFSSISAPHYEDIPFTRADPMVAD

YKYDLKLQEYQSAIKVEPASPPYYSEKTQLYNRPHEEPSNSLMAIECRVCGDKASGFHYGVH

ACEGCKGFFRRTIRLKLIYDRCDLNCRIHKKSRNKCQYCRFQKCLAVGMSHNAIRFGRMPQA

EKEKLLAEISSDIDQLNPESADLRALAKHLYDSYIKSFPLTKAKARAILTGKTTDKSPFVIY

DMNSLMMGEDKIKFKHITPLQEQSKEVAIRIFQGCQFRSVEAVQEITEYAKNIPGFINLDLN

DQVTLLKYGVHEIIYTMLASLMNKDGVLISEGQGFMTREFLKNLRKPFGDFMEPKFEFAVKF

NALELDDSDLAIFIAVIILSGDRPGLLNVKPIEDIQDNLLQALELQLKLNHPESSQLFAKVL

QKMTDLRQIVTEHVQLLHVIKKTETDMSLHPLLQEIYKDLY
```

Mouse PPAR gamma 2

(SEQ ID NO: 2)

MGETLGDSPVDPEHGAFADALPMSTSQEITMVDTEMPFWPTNFGISSVDLSVMEDHSHSFDI
KPFTTVDFSSISAPHYEDIPFTRADPMVADYKYDLKLQEYQSAIKVEPASPPYYSEKTQLYN
RPHEEPSNSLMAIECRVCGDKASGFHYGVHACEGCKGFFRRTIRLKLIYDRCDLNCRIHKKS
RNKCQYCRFQKCLAVGMSHNAIRFGRMPQAEKEKLLAEISSDIDQLNPESADLRALAKHLYD
SYIKSFPLTKAKARAILTGKTTDKSPFVIYDMNSLMMGEDKIKFKHITPLQEQSKEVAIRIF
QGCQFRSVEAVQEITEYAKNIPGFINLDLNDQVTLLKYGVHEIIYTMLASLMNKDGVLISEG
QGFMTREFLKNLRKPFGDFMEPKFEFAVKFNALELDDSDLAIFIAVIILSGDRPGLLNVKPI
EDIQDNLLQALELQLKLNHPESSQLFAKVLQKMTDLRQIVTEHVQLLHVIKKTETDMSLHPL
LQEIYKDLY

Human PPAR gamma (SEQ ID NO: 3)

MGETLGDSPIDPESDSFTDTLSANISQEMTMVDTEMPFWPTNFGISSVDLSVMEDHSHSF
DIKPFTTVDFSSISTPHYEDIPFTRTDPVVADYKYDLKLQEYQSAIKVEPASPPYYSEKT
QLYNKPHEEPSNSLMAIECRVCGDKASGFHYGVHACEGCKGFFRRTIRLKLIYDRCDLNC
RIHKKSRNKCQYCRFQKCLAVGMSHNAIRFGRMPQAEKEKLLAEISSDIDQLNPESADLR
ALAKHLYDSYIKSFPLTKAKARAILTGKTTDKSPFVIYDMNSLMMGEDKIKFKHITPLQE
QSKEVAIRIFQGCQFRSVEAVQEITEYAKSIPGFVNLDLNDQVTLLKYGVHEIIYTMLAS
LMNKDGVLISEGQGFMTREFLKSLRKPFGDFMEPKFEFAVKFNALELDDSDLAIFIAVII
LSGDRPGLLNVKPIEDIQDNLLQALELQLKLNHPESSQLFAKLLQKMTDLRQIVTEHVQL
LQVIKKTETDMSLHPLLQEIYKDLY

Bovine PPAR gamma (SEQ ID NO: 4)

MGETLGDALIDPESEPFAVTVSARTSQEITMVDTEMPFWPTNFGISSVDLSMMDDHSHAF
DIKPFTTVDFSSISTPHYEDIPFPRADPMVADYKYDLKLQEYQSAIKVEPVSPPYYSEKT
QLYSKPHEEPSNSLMAIECRVCGDKASGFHYGVHACEGCKGFFRRTIRLKLIYDRCDLNC
RIHKKSRNKCQYCRFQKCLAVGMSHNAIRFGRMPQAEKEKLLAEISSDIDQLNPESADLR
ALAKHLYDSYIKSFPLTKAKARAILTGKTTDKSPFVIYDMNSLMMGEDKIKFKHISPLQE
PSKEVAIRIFQGCQFRSVEAVQEITEYAKNIPGFVNLDLNDQVTLLKYGVHEIIYTMLAS
LMNKDGVLISEGQGFMTREFLKSLRKPFGDFMEPKFEFAVKFNALELDDSDLAIFIAVII
LSGDRPGLLNVKPIEDIQDNLLQALELQLKLNHPESSQLFAKLLQKMTDLRQIVTEHVQL
LQVIKKTETDMSLHPLLQEIYKDLY

Rabbit PPAR gamma (SEQ ID NO: 5)

MVDTEMPFWPTNFGIGSVDLSVMDDHSHSFDIKPFTTVDFSSISAPHYEDLPFARADPMV
ADYKYDLKLQEYQSAIKVEPASPPYYSEKTQLYNKTHEEPSNSLMAIECRVCSDKASGFH
YGVHACEGCKGFFRRTIRLKLIYDRCDLNCRIHKKSRNKCQYCRFQKCLAVGMSHNAIRF
GRMPQAEKEKLLAEISSDIDQLNPESADLRALAKHLYDSYIKSFPLTKAKARAILTGKTT
DKSPFVIYDMNSLMMGEDKIKFKHITPLQEQSKEVAIRIFQGCQFRSVEAVQEITEYAKN
IPGFVSLDLNDQVTLLKYGVHEIIYTMLASLMNKDGVLISEGQGFMTREFLKSLRKPFGD
FMEPKFEFAVKFNALELDDSDLAIFIAVIILSGDRPGLLNVKPIEDIQDNLLQALELQLK
LNHPEASQLFAKLLQKMTDLRQIVTEHVQLLQVIKKTETDMSLHPLLQEIYKDLY

-continued

Pig PPAR gamma (SEQ ID NO: 6)
MGETLGDSLIDPESDAFDTLSANISQEVTMVDTEMPFWPTNFGISSVDLSVMDDHSHSFD

IKPFTTVDFSSISTPHYEDIPFPRADPMVADYKDLKLQDYQSAIKVEPVSPPYYSEKTQ

LYNKPHEEPSNSLMAIECRVCGDKASGFHYGVHACEGCKGFFRRTIRLKLIYDRCDLNCR

IHKKSRNKCQYCRFQKCLAVGMSHNAIRFGRMPQAEKEKLLAEISSDIDQLNPESADLRA

LAKHLYDSYIKSFPLTKAKARAILTGKTTDKSPFVIYDMNSLMMGEDKIKFKHITPLQEQ

SKEVAIRIFQGCQFRSVEAVQEITEYAKNIPGFVNLDLNDQVTLLKYGVHEIIYTMLASL

MNKDGVLISEGQGFMTREFLKSLRKPFGDFMEPKFEFAVKFNALELDDSDLAIFIAVIIL

SGDRPGLLNVKPIEDIQDNLLQALELQLKLNHPESSQLFAKLLQKMTDLRQIVTEHVQLL

QVIKKTETDMSLHPLLQEIYKDLY

Chicken PPAR gamma (SEQ ID NO: 7)
MVDTEMPFWPVNFGISPVDLSAMDDHMHSFDIKPFTTVDFSSISSPHYEDIPLGRADQTSIDYKYDI

KLQDCQSAIKMEPPSPPYFSEKVQLYNKPHEESSNSLMAIECRVCGDKASGFHYGVHACEGCKGFFR

RTIRLKLIYDRCDLNCRIHKKSRNKCQYCRFQKCLAVGMSHNAIRFGRMPQAEKEKLLAEISSDIDQ

LNPESADLRALAKHLYDSYIKSFPLTKAKARAILTGKTTDKSPFVIYDMNSLRMGEDQIKCKHASPL

QEQNKEVAIRIFQRCQFRSVEAVQEITEFAKNIPGFVNLDLNDQVTLLKYGVHEIIYTLLASLMNKD

GVLISDGQGFMTREFLKSLRKPFCDFMEPKFEFAVKFNALELDDSDLAIFIAVIILSGDRPGLLNVK

PIEDIQDNLLQALELQLKLNHPESSQLFAKLLQKMTDLRQIVTEHVQLLQIIKKTETDMSLHPLLQE

IYKDLY

Mouse PPAR alpha (SEQ ID NO: 8)
MVDTESPICPLSPLEADDLESPLSEEFLQEMGNIQEISQSIGEESSGSFGFADYQYLGSCPGSEGSV

ITDTLSPASSPSSVSCPVIPASTDESPGSALNIECRICGDKASGYHYGVHACEGCKGFFRRTIRLKL

VYDKCDRSCKIQKKNRNKCQYCRFHKCLSVGMSHNAIRFGRMPRSEKAKLKAEILTCEHDLKDSETA

DLKSLGKRIHEAYLKNFNMNKVKARVILAGKTSNNPPFVIHDMETLCMAEKTLVAKMVANGVEDKEA

EVRFFHCCQCMSVETVTELTEFAKAIPGFANLDLNDQVTLLKYGVYEAIFTMLSSLMNKDGMLIAYG

NGFITREFLKNLRKPFCDIMEPKFDFAMKFNALELDDSDISLFVAAIICCGDRPGLLNIGYIEKLQE

GIVHVLKLHLQSNHPDDTFLFPKLLQKMVDLRQLVTEHAQLVQVIKKTESDAALHPLLQEIYRDMY

Mouse PPAR delta (SEQ ID NO: 9)
MEQPQEETPEAREEEKEEVAMGDGAPELNGGPEHTLPSSSCADLSQNSSPSSLLDQLQMGCDGASGG

SLNMECRVCGDKASGFHYGVHACEGCKGFFRRTIRMKLEYEKCDRICKIQKKNRNKCQYCRFQKCLA

LGMSHNAIRFGRMPEAEKRKLVAGLTASEGCQHNPQLADLKAFSKHIYNAYLKNFNMTKKKARSILT

GKSSHNAPFVIHDIETLWQAEKGLVWKQLVNGLPPYNEISVHVFYRCQSTTVETVRELTEFAKNIPN

FSSLFLNDQVTLLKYGVHEAIFAMLASIVNKDGLLVANGSGFVTHEFLRSLRKPFSDIIEPKFEFAV

KFNALELDDSDLALFIAAIILCGDRPGLMNVPQVEAIQDTILRALEFHLQVNHPDSQYLFPKLLQKM

ADLRQLVTEHAQMMQWLKKTESETLLHPLLQEIYKDMY

Mouse PPAR gamma 2 mRNA (SEQ ID NO: 10; NM_011146.3)
  1 caaaacacca gtgtgaatta cagcaaatct ctgtttatg ctgttatggg tgaaactctg 61 ggagattctc ctgttgaccc agagcatggt gccttcgctg atgcactgcc tatgagcact 121 tcacaagaaa ttaccatggt tgacacagag atgccattct ggcccaccaa cttcggaatc 181 agctctgtgg acctctccgt gatggaagac cactcgcatt cctttgacat caagcccttt 241 accacagttg atttctccag catttctgct ccacactatg aagacattcc attcacaaga -continued

```
 301 gctgacccaa tggttgctga ttacaaatat gacctgaagc tccaagaata ccaaagtgcg
 361 atcaaagtag aacctgcatc tccaccttat tattctgaaa agacccagct ctacaacagg
 421 cctcatgaag aaccttctaa ctccctcatg ccattgagt gccgagtctg tggggataaa
 481 gcatcaggct tccactatgg agttcatgct tgtgaaggat gcaagggttt tttccgaaga
 541 accatccgat tgaagcttat ttatgatagg tgtgatctta actgccggat ccacaaaaaa
 601 agtagaaata aatgtcagta ctgtcggttt cagaagtgcc ttgctgtggg gatgtctcac
 661 aatgccatca ggtttgggcg gatgccacag gccgagaagg agaagctgtt ggcggagatc
 721 tccagtgata tcgaccagct gaacccagag tctgctgatc tgcgagccct ggcaaagcat
 781 ttgtatgact catacataaa gtccttcccg ctgaccaaag ccaaggcgag ggcgatcttg
 841 acaggaaaga caacggacaa atcaccattt gtcatctacg acatgaattc cttaatgatg
 901 ggagaagata aaatcaagtt caaacatatc accccctgc aggagcagag caaagaggtg
 961 gccatccgaa tttttcaagg gtgccagttt cgatccgtag aagccgtgca agagatcaca
1021 gagtatgcca aaaatatccc tggtttcatt aaccttgatt tgaatgacca agtgactctg
1081 ctcaagtatg gtgtccatga gatcatctac acgatgctgg cctccctgat gaataaagat
1141 ggagtcctca tctcagaggg ccaaggattc atgaccaggg agttcctcaa aagcctgcgg
1201 aagccctttg gtgactttat ggagcctaag tttgagtttg ctgtgaagtt caatgcactg
1261 gaattagatg acagtgactt ggctatattt atagctgtca ttattctcag tggagaccgc
1321 ccaggcttgc tgaacgtgaa gcccatcgag gacatccaag acaacctgct gcaggccctg
1381 gaactgcagc tcaagctgaa tcacccagag tcctctcagc tgttcgccaa ggtgctccag
1441 aagatgacag acctcaggca gatcgtcaca gagcacgtgc agctactgca tgtgatcaag
1501 aagacagaga cagacatgag ccttcacccc ctgctccagg atctacaa ggacttgtat
1561 tagcaggaaa gtcccacccg ctgacaacgt gttccttcta ttgattgcac tattattttg
1621 agggaaaaaa atctgacacc taagaaattt actgtgaaaa agcatttaaa aacaaaaagt
1681 tttagaacat gatctatttt atgcatattg tttataaaga tacatttaca atttactttt
1741 aatattaaaa attaccacat tataaaatt
```
Mouse PPAR gamma 2 mRNA coding sequence
                                        (SEQ ID NO: 11; NM_011146.3)
```
   1 atgggtgaaa ctctgggaga ttctcctgtt gacccagagc atggtgcctt cgctgatgca
  61 ctgcctatga gcacttcaca agaaattacc atggttgaca cagagatgcc attctggccc
 121 accaacttcg gaatcagctc tgtggacctc tccgtgatgg aagaccactc gcattccttt
 181 gacatcaagc ccttttaccac agttgatttc tccagcattt ctgctccaca ctatgaagac
 241 attccattca agagctgac ccaatggttt gctgattaca atatgaccct gaagctccaa
 301 gaataccaaa gtgcgatcaa agtagaacct gcatctccac cttattattc tgaaaagacc
 361 cagctctaca caggcctca tgaagaacct tctaactccc tcatggccat tgagtgccga
 421 gtctgtgggg ataaagcatc aggcttccac tatggagttc atgcttgtga aggatgcaag
 481 ggttttttcc gaagaaccat ccgattgaag cttatttatg ataggtgtga tcttaactgc
 541 cggatccaca aaaaagtag aaataaatgt cagtactgtc ggtttcagaa gtgccttgct
 601 gtggggatgt ctcacaatgc catcaggttt ggcggatgc cacaggccga aggagaag
 661 ctgttggcgg agatctccag tgatatcgac cagctgaacc cagagtctgc tgatctgcga
 721 gccctggcaa agcatttgta tgactcatac ataaagtcct tcccgctgac caaagccaag
 781 gcgagggcga tcttgacagg aaagacaacg gacaaatcac catttgtcat ctacgacatg
```

```
 841 aattccttaa tgatgggaga agataaaatc aagttcaaac atatcacccc cctgcaggag 901 cagagcaaag aggtggccat ccgaattttt caagggtgcc agtttcgatc cgtagaagcc 961 gtgcaagaga tcacagagta tgccaaaaat atccctggtt tcattaacct tgatttgaat 1021 gaccaagtga ctctgctcaa gtatggtgtc catgagatca tctacacgat gctggcctcc 1081 ctgatgaata aagatggagt cctcatctca gagggccaag gattcatgac cagggagttc 1141 ctcaaaagcc tgcggaagcc ctttggtgac tttatggagc taagtttga gtttgctgtg 1201 aagttcaatg cactggaatt agatgacagt gacttggcta tatttatagc tgtcattatt 1261 ctcagtggag accgcccagg cttgctgaac gtgaagccca tcgaggacat ccaagacaac 1321 ctgctgcagg ccctggaact gcagctcaag ctgaatcacc cagagtcctc tcagctgttc 1381 gccaaggtgc tccagaagat gacagacctc aggcagatcg tcacagagca cgtgcagcta 1441 ctgcatgtga tcaagaagac agagacagac atgagccttc accccctgct ccaggagatc 1501 tacaaggact tgtattag
```

Human PPAR gamma 2 mRNA
(SEQ ID NO: 12; NM_015869.4)

```
   1 ttcaagtctt tttcttttaa cggattgatc ttttgctaga tagagacaaa atatcagtgt 61 gaattacagc aaaccccctat tccatgctgt tatgggtgaa actctgggag attctcctat 121 tgacccagaa agcgattcct tcactgatac actgtctgca acatatcac aagaaatgac 181 catggttgac acagagatgc cattctggcc caccaacttt gggatcagct ccgtggatct 241 ctccgtaatg gaagaccact cccactcctt tgatatcaag cccttcacta ctgttgactt 301 ctccagcatt tctactccac attacgaaga cattccattc acaagaacag atccagtggt 361 tgcagattac aagtatgacc tgaaacttca agagtaccaa agtgcaatca agtggagcc 421 tgcatctcca ccttattatt ctgagaagac tcagctctac aataagcctc atgaagagcc 481 ttccaactcc ctcatggcaa ttgaatgtcg tgtctgtgga gataaagctt ctggatttca 541 ctatggagtt catgcttgtg aaggatgcaa gggtttcttc cggagaacaa tcagattgaa 601 gcttatctat gacagatgtg atcttaactg tcggatccac aaaaaagta gaaataaatg 661 tcagtactgt cggtttcaga atgccttgc agtggggatg tctcataatg ccatcaggtt 721 tgggcggatg ccacaggccg agaaggagaa gctgttggcg gagatctcca gtgatatcga 781 ccagctgaat ccagagtccg ctgacctccg ggccctggca aaacatttgt atgactcata 841 cataaagtcc ttcccgctga ccaaagcaaa ggcgagggcg atcttgacag aaagacaac 901 agacaaatca ccattcgtta tctatgacat gaattcctta atgatgggag aagataaaat 961 caagttcaaa cacatcaccc ccctgcagga gcagagcaaa gaggtggcca tccgcatctt 1021 tcagggctgc cagtttcgct ccgtggaggc tgtgcaggag atcacagagt atgccaaaag 1081 cattcctggt tttgtaaatc ttgacttgaa cgaccaagta actctcctca aatatggagt 1141 ccacgagatc atttacacaa tgctggcctc cttgatgaat aaagatgggg ttctcatatc 1201 cgagggccaa ggcttcatga caagggagtt ctaaagagc ctgcgaaagc cttttggtga 1261 ctttatggag cccaagtttg agtttgctgt gaagttcaat gcactggaat tagatgacag 1321 cgacttggca atatttattg ctgtcattat tctcagtgga accgcccag gtttgctgaa 1381 tgtgaagccc attgaagaca ttcaagacaa cctgctacaa gccctggagc tccagctgaa 1441 gctgaaccac cctgagtcct cacagctgtt tgccaagctg ctccagaaaa tgacagacct 1501 cagacagatt gtcacggaac acgtgcagct actgcaggtg atcaagaaga cggagacaga 1561 catgagtctt caccccgctc ctgcaggagat ctacaaggac ttgtactagc agagagtcct 1621 gagccactgc caacatttcc cttcttccag ttgcactatt ctgagggaaa atctgacacc
```

-continued

```
1681 taagaaattt actgtgaaaa agcattttaa aaagaaaagg ttttagaata tgatctattt 1741 tatgcatatt gtttataaag acacatttac aatttacttt taatattaaa aattaccata 1801 ttatgaaatt gctgatagta
```

Human PPAR gamma 2 mRNA coding sequence
(SEQ ID NO: 13; NM_015869.4)

```
   1 atgggtgaaa ctctgggaga ttctcctatt gacccagaaa gcgattcctt cactgataca 61 ctgtctgcaa acatatcaca agaaatgacc atggttgaca cagagatgcc attctggccc 121 accaactttg ggatcagctc cgtggatctc tccgtaatgg aagaccactc ccactccttt 181 gatatcaagc ccttcactac tgttgacttc tccagcattt ctactccaca ttacgaagac 241 attccattca caagaacaga tccagtggtt gcagattaca agtatgacct gaaacttcaa 301 gagtaccaaa gtgcaatcaa agtggagcct gcatctccac cttattattc tgagaagact 361 cagctctaca ataagcctca tgaagagcct tccaactccc tcatggcaat tgaatgtcgt 421 gtctgtggag ataaagcttc tggatttcac tatggagttc atgcttgtga aggatgcaag 481 ggtttcttcc ggagaacaat cagattgaag cttatctatg acagatgtga tcttaactgt 541 cggatccaca aaaaagtag aaataaatgt cagtactgtc ggtttcagaa atgccttgca 601 gtggggatgt ctcataatgc catcaggttt gggcggatgc cacaggccga gaaggagaag 661 ctgttggcgg agatctccag tgatatcgac cagctgaatc cagagtccgc tgacctccgg 721 gccctggcaa acatttgta tgactcatac ataaagtcct tcccgctgac caaagcaaag 781 gcgagggcga tcttgacagg aaagacaaca gacaaatcac cattcgttat ctatgacatg 841 aattccttaa tgatgggaga agataaaatc aagttcaaac acatcacccc cctgcaggag 901 cagagcaaag aggtggccat ccgcatcttt cagggctgcc agtttcgctc cgtggaggct 961 gtgcaggaga tcacagagta tgccaaaagc attcctggtt ttgtaaatct tgacttgaac 1021 gaccaagtaa ctctcctcaa atatggagtc cacgagatca tttacacaat gctggcctcc 1081 ttgatgaata aagatggggt tctcatatcc gagggccaag gcttcatgac aagggagttt 1141 ctaaagagcc tgcgaaagcc ttttggtgac tttatggagc ccaagtttga gtttgctgtg 1201 aagttcaatg cactggaatt agatgacagc gacttggcaa tatttattgc tgtcattatt 1261 ctcagtggag accgcccagg tttgctgaat gtgaagccca ttgaagacat tcaagacaac 1321 ctgctacaag ccctggagct ccagctgaag ctgaaccacc ctgagtcctc acagctgttt 1381 gccaagctgc tccagaaaat gacagacctc agacagattg tcacggaaca cgtgcagcta 1441 ctgcaggtga tcaagaagac ggagacagac atgagtcttc acccgctcct gcaggagatc 1501 tacaaggact gtgtactag
```

"PPAR gamma agonist," as used herein, refers to any compound that, by any mechanism, increases, or causes an increase in the activity of PPAR gamma or the heterodimer of PPAR gamma with the retinoid X receptor (RXR), either by direct binding to either PPAR gamma or RXR or indirectly through any other mechanism that affects the ability of PPAR gamma or the PPAR gamma-RXR heterodimer to influence gene expression.

A "classical PPAR gamma agonist" as used herein refers to a PPAR gamma ligand that promotes PPAR gamma-mediated gene expression, which is associated with promoting metabolic disorders. A classical PPAR gamma agonist promotes expression of "adipogenic" genes (see, for example, genes, activities and assays set forth in Table 2 below). Genes that are regulated by the PPAR gamma agonist, rosiglitazone, are an example. Side effects associated with classical PPAR gamma agonists, include, for instance, weight gain, white adipocyte gain, fluid retention, peripheral edema, and pulmonary edema.

An "atypical PPAR gamma agonist" or "selective PPAR gamma agonist" as used herein refers to a PPAR gamma ligand that regulates expression of genes that are regulated predominantly and/or exclusively through cdk5-mediated phosphorylation of PPAR gamma. Examples include "anti-diabetic," "brown fat," and/or "increased respiration/oxygen consumption" genes (see, for example, Table 1). An example of an atypical PPAR gamma ligand is, for example, MRL24. In certain embodiments, atypical PPAR gamma agonists may promote anti-metabolic disorder activities without one or more of the side effects associated with classical PPAR gamma agonists, including, for example, weight gain, white adipocyte gain, fluid retention, peripheral edema, and pulmonary edema. Accordingly, exemplary atypical PPAR gamma ligands of the present invention, at least in part, may comprise compounds or pharmaceutical compositions having, for example, a blood sugar reducing effect, a blood lipid reducing effect, a blood insulin reducing effect, an insulin sensitivity enhancing effect, an insulin resistance improving effect, a body weight reducing effect, a central body girth (measured as waist:hip ratio) reducing effect, and/or, a body fat mass reducing effect.

PPAR gamma ligands include, but are not limited to, thiazolidinediones (e.g., rosiglitazone, pioglitazone, MK-0533, MK 767 (KRP-297), MCC-555, netoglitazone, balaglitazone, rivoglitazone), non-thiazolidinediones (e,g, JTT-501, LSN862, DRF 4832, LM 4156, LY 510929, LY 519818, TY 51501, X 334), certain tyrosine-based derivatives (e.g., GW1929, GW7845), phenylacetic acid-based derivatives, phenoxazine phenyl propanoic acid derivatives (e.g., DRF 2725, DRF 2189), cinammic and dihydrocinammic acid-based derivatives (e.g., tesaglitazar (AZ 242)), and 3-Phenyl-7-propylbenzisoxazoles (Adams A D, et al. Bioorg Med Chem. Lett. (2003) 13:931-5), MRL-20, MRL-24, nTZDpa, SR145, SR147, Mbx-102, and BVT.13.

"Responsiveness," to "respond" to treatment, and other forms of this verb, as used herein, refer to the reaction of a subject to treatment with a PPAR gamma ligand. As an example, a subject responds to treatment with a PPAR gamma ligand if an anti-metabolic activity in the subject is retarded by about 10%, 20%, 30%, 40%, 50%, 60%, 70%, 80%, 90% or more. In another example, a subject responds to treatment with an atypical PPAR gamma ligand if the subject experiences a life expectancy extended by about 5%, 10%, 20%, 30%, 40%, 50% or more beyond the life expectancy predicted if no treatment is administered. In another example, a subject responds to treatment with a PPAR gamma ligand if the subject has an increased metabolic disorder-free survival, overall survival or increased time to progression of a metabolic disorder.

"Sample," "tissue sample," "subject sample," "subject cell or tissue sample" or "specimen" each refer to a collection of similar cells obtained from a tissue of a subject or subject. The source of the tissue sample may be solid tissue as from a fresh, frozen and/or preserved organ, tissue sample, biopsy, or aspirate; blood or any blood constituents; bodily fluids such as cerebral spinal fluid, amniotic fluid, peritoneal fluid or interstitial fluid; or cells from any time in gestation or development of the subject. The tissue sample may contain compounds that are not naturally intermixed with the tissue in nature such as preservatives, anticoagulants, buffers, fixatives, nutrients, antibiotics or the like.

The amount of a biomarker, e.g., expression or copy number of biomarkers of the present invention, at least in part, (e.g., biomarkers set forth in Tables 1 and 2), in a subject is "significantly" higher or lower than the normal amount of a biomarker, if the amount of the biomarker is greater or less, respectively, than the normal level by an amount greater than the standard error of the assay employed to assess amount, or at least two, three, four, five, ten or more times that amount. Alternately, the amount of the biomarker in the subject can be considered "significantly" higher or lower than the normal amount if the amount is at least about two, at least about three, at least about four, or at least about five times, higher or lower, respectively, than the normal amount of the biomarker.

As used herein, the terms "subject" and "patient" are used interchangeably. As used herein, the terms "subject" and "subjects" refer to an animal, e.g., a mammal including a non-primate (e.g., a cow, pig, horse, donkey, goat, camel, cat, dog, guinea pig, rat, mouse, sheep) and a primate (e.g., a monkey, such as a cynomolgous monkey, gorilla, chimpanzee and a human).

As used herein, "time course" shall refer to the amount of time between an initial event and a subsequent event. For example, with respect to a subject's metabolic disorder (e.g., diabetes and/or obesity), time course may relate to a subject's disease and may be measured by gauging significant events in the course of the disease, wherein the first event may be diagnosis and the subsequent event may be significant weight loss, insulin sensitivity, etc.

"Time to progression" or "TTP" refers to a time as measured from the start of the treatment to progression of metabolic disorder (e.g., diabetes and/or obesity) or censor. Censoring may come from a study end or from a change in treatment. Time to progression can also be represented as a probability as, for example, in a Kaplin-Meier plot where time to progression may represent the probability of being progression free over a particular time, that time being the time between the start of the treatment to progression or censor.

A "transcribed polynucleotide" is a polynucleotide (e.g., an RNA, a cDNA, or an analog of one of an RNA or cDNA) which is complementary to or homologous with all or a portion of a mature RNA made by transcription of a biomarker of the present invention, at least in part, and normal post-transcriptional processing (e.g., splicing), if any, of the transcript, and reverse transcription of the transcript.

"Treat," "treatment," and other forms of this word refer to the administration of a PPAR gamma ligand to impede growth of a metabolic disorder (e.g., diabetes and/or obesity), to cause a metabolic disorder (e.g., diabetes and/or obesity) to be ameliorated, to extend the expected survival time of the subject and/or time to progression of a metabolic disorder or the like.

An "underexpression" or "significantly lower level of expression, copy number, and/or activity" of biomarkers of the present invention, at least in part, (e.g., biomarkers set forth in Tables 1 and 2) refers to an expression level or copy number in a test sample that is greater than the standard error of the assay employed to assess expression or copy number, for example, at least twice, at least three, at least four, at least five, or at least ten or more times less than the expression level, copy number, and/or activity of the biomarkers of the present invention, at least in part, (e.g., biomarkers set forth in Tables 1 and 2) in a control sample (e.g., a sample from a healthy subject not afflicted with a metabolic disorder (e.g., diabetes and/or obesity)), or the average expression level, copy number, and/or activity of the biomarkers of the present invention, at least in part, (e.g., biomarkers set forth in Tables 1 and 2) in several control samples.

"Unlikely to" refers to a decreased probability that an event, item, object, thing or person will occur with respect to a reference. Thus, a subject that is unlikely to respond to treatment with a PPAR gamma ligand has a decreased probability of responding to treatment with a PPAR gamma ligand relative to a reference subject or group of subjects (such as decreased by at least 5%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200%, or more (or any range inclusive).

I. Nucleic Acids of the Invention

One aspect of the invention pertains to compositions and methods utilizing isolated nucleic acid molecules that encode PPAR gamma polypeptides or biologically active portions thereof that cannot be phosphorylated at serine 273 of the mouse as well as to corresponding isoforms, homologs, and orthologs in other species corresponding to said serine 273, including, for example, humans, that cannot be phosphorylated at corresponding serine residues (i.e., hereinafter referred to as non-phosphorylatable PPAR gamma), as well as nucleic acid fragments sufficient for use as hybridization probes to identify non-phosphorylatable PPAR gamma polypeptides or biologically active portions thereof-encoding nucleic acid (i.e., mRNA). As used herein, the term "nucleic acid molecule" is intended to include DNA molecules (i.e., cDNA or genomic DNA) and RNA molecules (i.e., mRNA) and analogs of the DNA or RNA generated using nucleotide analogs. The nucleic acid molecule can be single-stranded or double-stranded DNA. An "isolated" nucleic acid molecule is one which is separated from other nucleic acid molecules which are present in the natural source of the nucleic acid. An "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated non-phosphorylatable PPAR gamma nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (i.e., a brown adipocyte). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, at least in part, i.e., a nucleic acid molecule listed in Tables 1 and 2 or a nucleotide sequence which is at least about 50%, at least about 60%, at least about 70%, at least about 80%, at least about 90%, and at least about 95% or more (e.g., about 96%, 96.5%, 97%, 97.5%, 98%, 98.5%, 99%, 99.5%, 99.6%, 99.7%, 99.8%, 99.9% or more) homologous to a nucleotide sequence shown in Tables 1 and 2 or a portion thereof (i.e., 400, 450, 500, or more nucleotides), can be isolated using standard molecular biology techniques and the sequence information provided herein. For example, a human non-phosphorylatable PPAR gamma cDNA can be isolated from a human liver, heart, kidney, or brain cell line (from Stratagene, LaJolla, Calif., or Clontech, Palo Alto, Calif.) using all or portion of the nucleotide sequence shown in Tables 1 and 2 as a hybridization probe and standard hybridization techniques (i.e., as described in Sambrook, J., Fritsh, E. F., and Maniatis, T. *Molecular Cloning: A Laboratory Manual*. 2nd, ed., Cold Spring Harbor Laboratory, Cold Spring Harbor Laboratory Press, Cold Spring Harbor, N.Y., 1989). Moreover, a nucleic acid molecule encompassing all or a portion of a nucleotide sequence shown in Tables 1 and 2 or a nucleotide sequence which is at least about 50%, at least about 60%, at least about 70%, at least about 80%, at least about 90%, and at least about 95% or more homologous to the nucleotide sequence shown in a nucleotide sequence shown in Tables 1 and 2 can be isolated by the polymerase chain reaction and/or site-directed mutagenesis using oligonucleotide primers designed based upon the sequence of a nucleotide sequence shown in Tables 1 and 2 or the homologous nucleotide sequence. For example, mRNA can be isolated from liver cells, heart cells, kidney cells, brain cells, or brown adipocytes (i.e., by the guanidinium-thiocyanate extraction procedure of Chirgwin et al. (1979) *Biochemistry* 18: 5294-5299) and cDNA can be prepared using reverse transcriptase (i.e., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in a nucleotide sequence shown in Tables 1 and 2 or to the homologous nucleotide sequence. A nucleic acid of the invention can be amplified using cDNA or, alternatively, genomic DNA (including both germline and somatic genomic DNA), as a template and appropriate oligonucleotide primers according to standard PCR amplification techniques. The nucleic acid so amplified can be cloned into an appropriate vector and characterized by DNA sequence analysis. Furthermore, oligonucleotides corresponding to a non-phosphorylatable PPAR gamma nucleotide sequence can be prepared by standard synthetic techniques, i.e., using an automated DNA synthesizer.

Probes based on the non-phosphorylatable PPAR gamma nucleotide sequences can be used to detect transcripts or genomic sequences encoding the same or homologous proteins. In certain embodiments, the probe further comprises a label group attached thereto, i.e., the label group can be a radioisotope, a fluorescent compound, an enzyme, or an enzyme co-factor. Such probes can be used as a part of a diagnostic test kit for identifying cells or tissue which express a non-phosphorylatable PPAR gamma protein, such as by measuring a level of a PPAR gamma polypeptides or biologically active portions thereof that cannot be phosphorylated at serine 273-encoding nucleic acid in a sample of cells from a subject, i.e., detecting non-phosphorylatable PPAR gamma mRNA levels.

Nucleic acid molecules encoding other non-phosphorylatable PPAR gamma family members and thus which have a nucleotide sequence which differs from the wild type PPAR gamma sequences of the sequences listed in Tables 1 and 2 are intended to be part of the invention. Moreover, nucleic acid molecules encoding non-phosphorylatable PPAR gamma proteins from different species, and thus which have a nucleotide sequence which differs from the non-phosphorylatable PPAR gamma sequences listed in Tables 1 and 2 are intended to be within the scope of the invention. For example, rat or monkey non-phosphorylatable PPAR gamma cDNA can be identified and/or synthesized based on known nucleotide sequences and engineered mutations of a human and/or mouse non-phosphorylatable PPAR gamma nucleic acid sequence.

In one embodiment, the nucleic acid molecule of the invention encodes a protein or portion thereof which includes an amino acid sequence which is sufficiently homologous to an amino acid sequence listed in Tables 1 and 2 such that the protein or portion thereof maintains one or more of the following biological activities described herein for mouse PPAR gamma polypeptide having a mutation of serine 273 to alanine (e.g., the inability of the 273th amino acid to become phosphorylated). For example, any nucleic acid mutation that prevents encoding of serine or a phosphorylatable amino acid residue such as threonine or tyrosine, is contemplated. Any and all such mutations are readily known to a person having ordinary skill in the art based upon the degeneracy of the genetic code and codon algorithms in a species of interest.

In another embodiment, the protein is at least about 50%, at least about 60%, at least about 70%, at least about 80%, at least about 90%, at least about 95% or more homologous to the entire amino acid sequence listed in Tables 1 and 2.

Portions of proteins encoded by the non-phosphorylatable PPAR gamma nucleic acid molecule of the invention are biologically active portions of the non-phosphorylatable PPAR gamma protein. As used herein, the term "biologically active portion of non-phosphorylatable PPAR gamma" is intended to include a portion, e.g., a domain/motif, of non-phosphorylatable PPAR gamma that selectively promotes anti-metabolic disorder activity over classical PPAR gamma activation according to one or more criteria as described herein (for example, a consensus cdk5 phosphorylation motif and/or mutated PPAR gamma non-phosphorylatable at Ser-273).

Standard binding assays, e.g., immunoprecipitations and yeast two-hybrid assays, as described herein, can be performed to determine the ability of a non-phosphorylatable PPAR gamma protein or a biologically active portion thereof to interact with a target of interest in assays that can be either PPAR gamma ligand-dependent or independent. To determine whether a non-phosphorylatable PPAR gamma family member of the present invention, at least in part, modulates a biomarker listed in Tables 1 and 2, in vitro transcriptional assays can be performed. To perform such an assay, the full length promoter/enhancer region of the gene of interest can be linked to a reporter gene such as chloramphenicol acetyl-transferase (CAT) or luciferase and introduced into host cells (e.g., liver cells such as Fao hepatoma cells, or COS cells). The same host cells can then be transfected with a nucleic acid molecule encoding the non-phosphorylatable PPAR gamma molecule. The effect of the non-phosphorylatable PPAR gamma molecule can be measured by testing CAT or luciferase activity and comparing it to CAT or luciferase activity in cells which do not contain nucleic acid encoding the non-phosphorylatable PPAR gamma molecule. An increase or decrease in CAT or luciferase activity indicates a modulation of expression of the gene of interest. In another embodiment, because expression of the biomarkers listed in Tables 1 and 2 are known to be a critical component in the cascade of events leading to discrete biological pathways, this assay can also measure the ability of the non-phosphorylatable PPAR gamma molecule to modulate such pathways, including, for example, fatty acid uptake, induction of brown fat by histology, gene expression, uncoupled oxygen consumption, mitochondrial biogenesis, etc., energy expenditure in vivo by increased oxygen consumption, thermogenesis, no change in food intake, etc., serum fatty acid levels, serum adipokine (adiponectin for example) levels, white fat depots, fat mass, lean mass, fasting glucose, glucose tolerance, insulin tolerance, insulin sensitivity, insulin-dependent glucose uptake, suppression of obesity-induced inflammation by analyzing TNF-alpha secretion, MCP1 inflammation gene expression, etc. Such analyses are well known in the art.

The invention further encompasses nucleic acid molecules that differ from the nucleotide sequence shown in Tables 1 and 2 (and portions thereof) due to degeneracy of the genetic code and thus encode non-phosphorylatable PPAR gamma protein in a number of ways readily known to a person having ordinary skill in the art. For example, the skilled artisan will further appreciate that changes can be introduced by mutation into the nucleotide sequence of Tables 1 and 2 thereby leading to changes in the amino acid sequence of the encoded non-phosphorylatable PPAR gamma protein, without altering the functional ability of the non-phosphorylatable PPAR gamma protein having the S273A mutation described in the examples. For example, nucleotide substitutions leading to amino acid substitutions at "non-essential" amino acid residues can be made in the sequence of. A "non-essential" amino acid residue is a residue that can be altered from the wild-type sequence of non-phosphorylatable PPAR gamma (e.g., the sequence listed in Tables 1 and 2) without altering the activity of non-phosphorylatable PPAR gamma, whereas an "essential" amino acid residue is required for non-phosphorylatable PPAR gamma activity. Other amino acid residues, however, (e.g., those that are not conserved or only semi-conserved between mouse and human) may not be essential for activity and thus are likely to be amenable to alteration without altering non-phosphorylatable PPAR gamma activity. Furthermore, amino acid residues that are essential for non-phosphorylatable PPAR gamma functions related to thermogenesis and/or adipogenesis, but not essential for non-phosphorylatable PPAR gamma functions related to gluconeogenesis, are likely to be amenable to alteration.

Accordingly, another aspect of the invention pertains to nucleic acid molecules encoding non-phosphorylatable PPAR gamma proteins that contain changes in amino acid residues that are not essential for non-phosphorylatable PPAR gamma activity. Such non-phosphorylatable PPAR gamma proteins differ in amino acid sequence from Tables 1 and 2 yet retain at least one of the non-phosphorylatable PPAR gamma activities described herein.

"Sequence identity or homology", as used herein, refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous or sequence identical at that position. The percent of homology or sequence identity between two sequences is a function of the number of matching or homologous identical positions shared by the two sequences divided by the number of positions compared×100. For example, if 6 of 10, of the positions in two sequences are the same then the two sequences are 60% homologous or have 60% sequence identity. By way of example, the DNA sequences ATTGCC and TATGGC share 50% homology or sequence identity. Generally, a comparison is made when two sequences are aligned to give maximum homology. Unless otherwise specified "loop out regions", e.g., those arising from, from deletions or insertions in one of the sequences are counted as mismatches.

The comparison of sequences and determination of percent homology between two sequences can be accomplished using a mathematical algorithm. The alignment can be performed using the Clustal Method. Multiple alignment parameters include GAP Penalty=10, Gap Length Penalty=10. For DNA alignments, the pairwise alignment parameters can be Htuple=2, Gap penalty=5, Window=4, and Diagonal saved=4. For protein alignments, the pairwise alignment parameters can be Ktuple=1, Gap penalty=3, Window=5, and Diagonals Saved=5.

In a certain embodiments, the percent identity between two amino acid sequences is determined using the Needleman and Wunsch (J. Mol. Biol. (48):444-453 (1970)) algorithm which has been incorporated into the GAP program in the GCG software package (available online), using either a Blossom 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences is determined using the GAP program in the GCG software package (available online), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0) (available online), using a PAM120 weight residue table, a gap length penalty of 12 and a gap penalty of 4.

An isolated nucleic acid molecule encoding a non-phosphorylatable PPAR gamma protein homologous to the protein listed in Tables 1 and 2 can be created by introducing one or more nucleotide substitutions, additions or deletions into the nucleotide sequence of Tables 1 and 2 or a homologous nucleotide sequence such that one or more amino acid substitutions, additions or deletions are introduced into the encoded protein. Mutations can be introduced into Tables 1 and 2 or the homologous nucleotide sequence by standard techniques, such as site-directed mutagenesis and PCR-mediated mutagenesis. Conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in non-phosphorylatable PPAR gamma is replaced with another amino acid residue from the same side chain family. Alternatively, in another embodiment, mutations can be introduced randomly along all or part of a non-phosphorylatable PPAR gamma coding sequence, such as by saturation mutagenesis, and the resultant mutants can be screened for a non-phosphorylatable PPAR gamma activity described herein to identify mutants that retain non-phosphorylatable PPAR gamma activity. Following mutagenesis of the sequence selected from Tables 1 and 2, the encoded protein can be expressed recombinantly (as described herein) and the activity of the protein can be determined using, for example, assays described herein.

Non-phosphorylatable PPAR gamma levels may be assessed by any of a wide variety of well known methods for detecting expression of a transcribed molecule or protein. Non-limiting examples of such methods include immunological methods for detection of proteins, protein purification methods, protein function or activity assays, nucleic acid hybridization methods, nucleic acid reverse transcription methods, and nucleic acid amplification methods.

In some embodiments, non-phosphorylatable PPAR gamma levels are ascertained by measuring gene transcript (e.g., mRNA), by a measure of the quantity of translated protein, or by a measure of gene product activity. Expression levels can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In a particular embodiment, the non-phosphorylatable PPAR gamma mRNA expression level can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding non-phosphorylatable PPAR gamma. Other suitable probes for use in the diagnostic assays of the invention are described herein. Hybridization of an mRNA with the probe indicates that non-phosphorylatable PPAR gamma is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in a gene chip array, e.g., an Affymetrix™ gene chip array. A skilled artisan can readily adapt known mRNA detection methods for use in detecting the level of the non-phosphorylatable PPAR gamma mRNA expression levels.

An alternative method for determining the non-phosphorylatable PPAR gamma mRNA expression level in a sample involves the process of nucleic acid amplification, e.g., by rtPCR (the experimental embodiment set forth in Mullis, 1987, U.S. Pat. No. 4,683,202), ligase chain reaction (Barany, 1991, *Proc. Natl. Acad. Sci. USA*, 88:189-193), self sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well-known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the cells prior to detection. In such methods, a cell or tissue sample is prepared/processed using known histological methods. The sample is then immobilized on a support, typically a glass slide, and then contacted with a probe that can hybridize to the non-phosphorylatable PPAR gamma mRNA.

As an alternative to making determinations based on the absolute non-phosphorylatable PPAR gamma expression level, determinations may be based on the normalized non-phosphorylatable PPAR gamma expression level. Expression levels are normalized by correcting the absolute non-phosphorylatable PPAR gamma expression level by comparing its expression to the expression of a non-non-phosphorylatable PPAR gamma gene, e.g., a housekeeping gene that is constitutively expressed. Suitable genes for normalization include housekeeping genes such as the actin gene, or epithelial cell-specific genes. This normalization allows the comparison of the expression level in one sample, e.g., a subject sample, to another sample, e.g., a normal sample, or between samples from different sources.

The level or activity of a non-phosphorylatable PPAR gamma protein can also be detected and/or quantified by detecting or quantifying the expressed polypeptide. The non-phosphorylatable PPAR gamma polypeptide can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, and the like. A skilled artisan can readily adapt known protein/antibody detection methods for use in determining whether cells express non-phosphorylatable PPAR gamma.

In addition to the nucleic acid molecules encoding non-phosphorylatable PPAR gamma proteins described above, another aspect of the invention pertains to isolated nucleic acid molecules which are antisense thereto. An "antisense" nucleic acid comprises a nucleotide sequence which is complementary to a "sense" nucleic acid encoding a protein, i.e., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire non-phosphorylatable PPAR gamma coding strand, or to only a portion thereof. In one embodiment, an antisense nucleic acid molecule is antisense to a "coding region" of the coding strand of a nucleotide sequence encoding non-phosphorylatable PPAR gamma. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding non-phosphorylatable PPAR gamma. The term "noncoding region" refers to 5' and 3' sequences which flank the coding region that are not translated into amino acids (i.e., also referred to as 5' and 3' untranslated regions).

II. Recombinant Expression Vectors and Host Cells

Another aspect of the invention pertains to the use of vectors and expression vectors containing a nucleic acid encoding non-phosphorylatable PPAR gamma (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. Adenoviral vectors comprising a non-phosphorylatable PPAR gamma nucleic acid molecule are used in certain embodiments.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., non-phosphorylatable PPAR gamma proteins, mutant forms of non-phosphorylatable PPAR gamma, fusion proteins, etc.).

The recombinant expression vectors of the invention can be designed for expression of non-phosphorylatable PPAR gamma in prokaryotic or eukaryotic cells. For example, non-phosphorylatable PPAR gamma can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the non-phosphorylatable PPAR gamma is cloned into a pGEX expression vector to create a vector encoding a fusion protein comprising, from the N-terminus to the C-terminus, GST-thrombin cleavage site-non-phosphorylatable PPAR gamma. The fusion protein can be purified by affinity chromatography using glutathione-agarose resin. Recombinant non-phosphorylatable PPAR gamma unfused to GST can be recovered by cleavage of the fusion protein with thrombin.

Examples of suitable inducible non-fusion E. coli expression vectors include pTrc (Amann et al., (1988) Gene 69:301-315) and pET 11d (Studier et al., Gene Expression Technology: Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression in E. coli is to express the protein in a host bacteria with an impaired capacity to proteolytically cleave the recombinant protein (Gottesman, S., Gene Expression Technology: Methods in Enzymology 185, Academic Press, San Diego, Calif. (1990) 119-128). Another strategy is to alter the nucleic acid sequence of the nucleic acid to be inserted into an expression vector so that the individual codons for each amino acid are those utilized in E. coli (Wada et al. (1992) Nucleic Acids Res. 20:2111-2118). Such alteration of nucleic acid sequences of the invention can be carried out by standard DNA synthesis techniques.

In another embodiment, the non-phosphorylatable PPAR gamma expression vector is a yeast expression vector. Examples of vectors for expression in yeast S. cerivisae include pYepSec1 (Baldari, et al., (1987) EMBO J. 6:229-234), pMFa (Kurjan and Herskowitz, (1982) Cell 30:933-943), pJRY88 (Schultz et al., (1987) Gene 54:113-123), and pYES2 (Invitrogen Corporation, San Diego, Calif.).

Alternatively, non-phosphorylatable PPAR gamma can be expressed in insect cells using baculovirus expression vectors. Baculovirus vectors available for expression of proteins in cultured insect cells (e.g., Sf 9 cells) include the pAc series (Smith et al. (1983) Mol. Cell. Biol. 3:2156-2165) and the pVL series (Lucklow and Summers (1989) Virology 170:31-39).

In yet another embodiment, a nucleic acid of the invention is expressed in mammalian cells using a mammalian expression vector. Examples of mammalian expression vectors include pCDM8 (Seed, B. (1987) Nature 329:840) and pMT2PC (Kaufman et al. (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), in particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) Science 249:374-379) and the α-fetoprotein promoter (Campes and Tilghman (1989) Genes Dev. 3:537-546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to non-phosphorylatable PPAR gamma mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, non-phosphorylatable PPAR gamma protein can be expressed in bacterial cells such as E. coli, insect cells, yeast or mammalian cells (such as Fao hepatoma cells, primary hepatocytes, Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable biomarker (e.g., resistance to antibiotics) is generally introduced into the host cells along with the gene of interest. Selectable markers include those which confer resistance to drugs, such as G418, hygromycin and methotrexate. Nucleic acid encoding a selectable biomarker can be introduced into a host cell on the same vector as that encoding non-phosphorylatable PPAR gamma or can be introduced on a separate vector. Cells stably transfected with the introduced nucleic acid can be identified by drug selection (e.g., cells that have incorporated the selectable biomarker gene will survive, while the other cells die).

A host cell of the invention, such as a prokaryotic or eukaryotic host cell in culture, can be used to produce (i.e., express) non-phosphorylatable PPAR gamma protein. Accordingly, the invention further provides methods for producing non-phosphorylatable PPAR gamma protein using the host cells of the invention. In one embodiment, the method comprises culturing the host cell of invention (into which a recombinant expression vector encoding non-phosphorylatable PPAR gamma has been introduced) in a suitable medium until non-phosphorylatable PPAR gamma is produced. In another embodiment, the method further comprises isolating non-phosphorylatable PPAR gamma from the medium or the host cell.

The host cells of the invention can also be used to produce nonhuman transgenic animals (e.g., knock-in animals). The nonhuman transgenic animals can be used in screening assays designed to identify agents or compounds, e.g., drugs, pharmaceuticals, etc., which are capable of ameliorating detrimental symptoms of selected disorders such as glucose homeostasis disorders, weight disorders or disorders associated with insufficient insulin activity. For example, in one embodiment, a host cell of the invention is a fertilized oocyte or an embryonic stem cell into which non-phosphorylatable PPAR gamma-coding sequences (for example, murine PPAR gamma encoding alanine or other non-phosphorylatable amino acid at position 273 rather than serine) have been introduced. Such host cells can then be used to create non-human transgenic animals in which exogenous non-phosphorylatable PPAR gamma sequences have been introduced into their genome or homologous recombinant animals in which endogenous non-phosphorylatable PPAR gamma sequences have been altered. Such animals are useful for studying the function and/or activity of non-phosphorylatable PPAR gamma and for identifying and/or evaluating modulators of non-phosphorylatable PPAR gamma activity using the methods and criteria described herein. As used herein, a "transgenic animal" is a nonhuman animal, a mammal, a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, a mammal, a mouse, in which an endogenous non-phosphorylatable PPAR gamma gene has been altered by homologous recombination between the endogenous gene and an exogenous DNA molecule introduced into a cell of the animal, e.g., an embryonic cell of the animal, prior to development of the animal.

A transgenic animal of the invention can be created by introducing non-phosphorylatable PPAR gamma-encoding nucleic acid into the male pronuclei of a fertilized oocyte, e.g., by microinjection, retroviral infection, and allowing the oocyte to develop in a pseudopregnant female foster animal. The human non-phosphorylatable PPAR gamma cDNA sequence can be introduced as a transgene into the genome of a nonhuman animal. Alternatively, a nonhuman homologue of the human non-phosphorylatable PPAR gamma gene, such as a mouse non-phosphorylatable PPAR gamma gene, can be used as a transgene. Intronic sequences and polyadenylation signals can also be included in the transgene to increase the efficiency of expression of the transgene. A tissue-specific regulatory sequence(s) can be operably linked to the non-phosphorylatable PPAR gamma transgene to direct expression of non-phosphorylatable PPAR gamma protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the non-phosphorylatable PPAR gamma transgene in its genome and/or expression of non-phosphorylatable PPAR gamma mRNA in tissues or cells of the animals. A transgenic founder animal can then be used to breed additional animals carrying the transgene. Moreover, transgenic animals carrying a transgene encoding non-phosphorylatable PPAR gamma can further be bred to other transgenic animals carrying other transgenes.

To create a homologous recombinant animal, a vector is prepared which contains at least a portion of a non-phosphorylatable PPAR gamma gene into which a deletion, addition or substitution has been introduced to thereby alter, e.g., replace, the wild-type, phosphorylatable PPAR gamma gene. The non-phosphorylatable PPAR gamma gene can be a human gene (e.g., from a human genomic clone isolated from a human genomic library screened with the cDNA of a sequence listed in Tables 1 and 2), and also a nonhuman homologue of a human non-phosphorylatable PPAR gamma gene. For example, a mouse non-phosphorylatable PPAR gamma gene can be used to construct a homologous recombination vector suitable for altering an endogenous phosphorylatable PPAR gamma gene in the mouse genome. In certain embodiments, the vector is designed such that, upon homologous recombination, the endogenous phosphorylatable PPAR gamma gene is functionally disrupted (i.e., no longer encodes a phosphorylatable protein; also referred to as a "knock in" vector). In the homologous recombination vector, the altered portion of the non-phosphorylatable PPAR gamma gene is flanked at its 5' and 3' ends by additional nucleic acid of the non-phosphorylatable PPAR gamma gene to allow for homologous recombination to occur between the exogenous non-phosphorylatable PPAR gamma gene carried by the vector and an endogenous non-phosphorylatable PPAR gamma gene in an embryonic stem cell. The additional flanking non-phosphorylatable PPAR gamma nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) Cell 51:503 for a description of homologous recombination vectors). The vector is introduced into an embryonic stem cell line (e.g., by electroporation) and cells in which the introduced non-phosphorylatable PPAR gamma gene has homologously recombined with the endogenous non-phosphorylatable PPAR gamma gene are selected (see e.g., Li, E. et al. (1992) Cell 69:915). The selected cells are then injected into a blastocyst of an animal (e.g., a mouse) to form aggregation chimeras (see e.g., Bradley, A. in Teratocarcinomas and Embryonic Stem Cells: A Practical Approach, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) Current Opinion in Biotechnology 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic nonhuman animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) Proc. Natl. Acad. Sci. USA 89:6232-6236. Another example of a recombinase system is the FLP recombinase system of Saccharomyces cerevisiae (O'Gorman et al. (1991) Science 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut, I. et al. (1997) Nature 385:810-813 and PCT International Publication Nos. WO 97/07668 and WO 97/07669. In brief, a cell, e.g., a somatic cell, from the transgenic animal can be isolated and induced to exit the growth cycle and enter $G_O$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring borne of this female foster animal will be a clone of the animal from which the cell, e.g., the somatic cell, is isolated.

Transgenic animals, such as S273A PPAR gamma mutant knock-in animals, have numerous uses, as further described herein.

In one embodiment, for example, knock-in animals homozygous for the S273A mutation of PPAR gamma can be used to test the efficacy of potential anti-metabolic disorder therapeutics. MRL-24 and similar compounds which block the phosphorylation of PPAR gamma at serine 273 by cdk5 (phopho-blockers) are believed to improve metabolic disorders without having the side-effects of classical agonists, such as TZDs. For example, PPAR gamma is active in both lean and obese individuals; however in these states, PPAR gamma exhibits slightly different transcription of target genes. It is believed that this difference in transcriptional activity is due to the inhibitory phosphorylation of PPAR gamma at Ser-273. Mice with both copies of PPAR gamma mutated at Ser-273 to alanine or other non-phosphorylatable amino acid residue should retain normal glucose tolerance when faced with the challenge of a high-fat diet. The glucose lowering effect of MRL-24 does not require PPAR gamma agonism, an effect that is likely responsible for weight gain and fluid retention observed upon administration of classical PPAR gamma agonists. In general, it is believed that such classical PPAR gamma agonists (e.g., rosiglitizone) will have the positive glucose lowering only in WT mice but not in S273A mice. However the side effects, such as weight gain and fluid retention are believed to still occur in both strains. Hence, an ideal compound would have no effect in the knock-in mice making it a good model for testing off-target effects of the drug.

In another embodiment, cells lines taken from these knock-in mice can be used for in vitro testing of potential compounds. Specific chemical entities are believed to only alter target genes in wild-type cells, not in knock-in cells.

In still another embodiment, bone marrow transplantation from a wild type animal to S273A knock-in animals and vice versa can be used to analyze activity of such mutant polypeptides in immune system cells (e.g., macrophages and monocytes) in a wild type host background and vice versa. One example of this use would be to determine whether risk of atherosclerosis due to CD36-dependent decreased lipid uptake is mediated by immune system cells.

III. Isolated Non-Phosphorylatable PPAR Gamma Proteins and Anti-Non-Phosphorylatable PPAR Gamma Antibodies Another aspect of the invention pertains to the use of isolated non-phosphorylatable PPAR gamma proteins, and biologically active portions thereof, as well as peptide fragments suitable for use as immunogens to raise anti-non-phosphorylatable PPAR gamma antibodies. An "isolated" or "purified" protein or biologically active portion thereof is substantially free of cellular material when produced by recombinant DNA techniques, or chemical precursors or other chemicals when chemically synthesized. The language "substantially free of cellular material" includes preparations of non-phosphorylatable PPAR gamma protein in which the protein is separated from cellular components of the cells in which it is naturally or recombinantly produced. In one embodiment, the language "substantially free of cellular material" includes preparations of non-phosphorylatable PPAR gamma protein having less than about 30% (by dry weight) of non-non-phosphorylatable PPAR gamma protein (also referred to herein as a "contaminating protein"), less than about 20% of non-non-phosphorylatable PPAR gamma protein, less than about 10% of non-non-phosphorylatable PPAR gamma protein, and less than about 5% non-non-phosphorylatable PPAR gamma protein. When the non-phosphorylatable PPAR gamma protein or biologically active portion thereof is recombinantly produced, it is also substantially free of culture medium, i.e., culture medium represents less than about 20%, less than about 10%, and less than about 5% of the volume of the protein preparation. The language "substantially free of chemical precursors or other chemicals" includes preparations of non-phosphorylatable PPAR gamma protein in which the protein is separated from chemical precursors or other chemicals which are involved in the synthesis of the protein. In one embodiment, the language "substantially free of chemical precursors or other chemicals" includes preparations of non-phosphorylatable PPAR gamma protein having less than about 30% (by dry weight) of chemical precursors or non-non-phosphorylatable PPAR gamma chemicals, less than about 20% chemical precursors or non-non-phosphorylatable PPAR gamma chemicals, less than about 10% chemical precursors or non-non-phosphorylatable PPAR gamma chemicals, and less than about 5% chemical precursors or non-non-phosphorylatable PPAR gamma chemicals. In certain embodiments, isolated proteins or biologically active portions thereof lack contaminating proteins from the same animal from which the non-phosphorylatable PPAR gamma protein is derived. Typically, such proteins are produced by recombinant expression of, for example, a human non-phosphorylatable PPAR gamma protein in a nonhuman cell.

An exemplary isolated non-phosphorylatable PPAR gamma protein or a portion thereof of the invention selectively promotes anti-metabolic disorder activity over classical PPAR gamma activation according to one or more criteria as described herein.

The portion of the protein may be a biologically active portion as described herein. In another embodiment, the non-phosphorylatable PPAR gamma protein has an amino acid sequence shown in Tables 1 and 2, respectively, or an amino acid sequence which is at least about 50%, at least about 60%, at least about 70%, at least about 80%, at least about 90%, and at least about 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or more homologous to the amino acid sequence shown in Tables 1 and 2. In yet another embodiment, the non-phosphorylatable PPAR gamma protein has an amino acid sequence which is encoded by a nucleotide sequence which hybridizes, e.g., hybridizes under stringent conditions, to the nucleotide sequence listed in Tables 1 and 2 or a nucleotide sequence which is at least about 50%, at least about 60%, at least about 70%, at least about 80%, at least about 90%, and at least about 95% or more homologous to the nucleotide sequence shown in Tables 1 and 2. The non-phosphorylatable PPAR gamma proteins of the present invention, at least in part, also possess at least one of the non-phosphorylatable PPAR gamma biological activities described herein. For example, a non-phosphorylatable PPAR gamma protein of the present invention, at least in part, includes an amino acid sequence encoded by a nucleotide sequence which hybridizes, e.g., hybridizes under stringent conditions, to the nucleotide sequence listed in Tables 1 and 2 and which selectively promotes anti-metabolic disorder activity over classical PPAR gamma activation according to one or more criteria as described herein.

As used herein, the twenty conventional amino acids and their abbreviations follow conventional usage. See Immunology—A Synthesis (2.sup.nd Edition, E. S. Golub and D. R. Gren, Eds., Sinauer Associates, Sunderland, Mass. (1991)), which is incorporated herein by reference. The term "amino acid" or "amino acid residue," as used herein, refers to naturally occurring L amino acids or to D amino acids. The commonly used one- and three-letter abbreviations for amino acids are used herein (Bruce Alberts et al., Molecular Biology of the Cell, Garland Publishing, Inc., New York (4th ed. 2002)). Stereoisomers (e.g., D-amino acids) of the twenty conventional amino acids, unnatural amino acids such as alpha,alpha-disubstituted amino acids, N-alkyl amino acids, lactic acid, and other unconventional amino acids may also be suitable components for polypeptides of the present invention, at least in part. Examples of unconventional amino acids include: 4-hydroxyproline, .gamma.-carboxyglutamate, .epsilon.-N,N,N-trimethyllysine, .epsilon.-N-acetyllysine, O-phosphoserine, N-acetylserine, N-formylmethionine, 3-methylhistidine, 5-hydroxylysine, .sigma.-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

In other embodiments, the non-phosphorylatable PPAR gamma protein is substantially homologous to the amino acid sequence listed in Tables 1 and 2 and retains the functional activity of the protein listed in Tables 1 and 2 yet differs in amino acid sequence due to natural allelic variation or mutagenesis, as described in detail in subsection I above. Accordingly, in another embodiment, the non-phosphorylatable PPAR gamma protein is a protein which comprises an amino acid sequence which is at least about 50%, at least about 60%, at least about 70%, at least about 80%, at least about 90%, and at least about 95% or more homologous to the amino acid sequence listed in Tables 1 and 2.

Biologically active portions of the non-phosphorylatable PPAR gamma protein include peptides comprising amino acid sequences derived from the amino acid sequence of the non-phosphorylatable PPAR gamma protein, e.g., the amino acid sequence shown in Tables 1 and 2 or the amino acid sequence of a protein homologous to the non-phosphorylatable PPAR gamma protein, which include fewer amino acids than the full length non-phosphorylatable PPAR gamma protein or the full length protein which is homologous to the non-phosphorylatable PPAR gamma protein, and exhibit at least one activity of the non-phosphorylatable PPAR gamma protein. Typically, biologically active portions (peptides, e.g., peptides which are, for example, 5, 10, 15, 20, 30, 35, 36, 37, 38, 39, 40, 50, 100 or more amino acids in length) comprise a domain or motif, e.g., a consensus cdk5 phosphorylation motif and/or mutated PPAR gamma non-phosphorylatable at Ser-273. Moreover, other biologically active portions, in which other regions of the protein are deleted, can be prepared by recombinant techniques and evaluated for one or more of the activities described herein. The biologically active portions of the non-phosphorylatable PPAR gamma protein include one or more selected domains/motifs or portions thereof having biological activity.

Non-phosphorylatable PPAR gamma proteins are produced by recombinant DNA techniques. For example, a nucleic acid molecule encoding the protein is cloned into an expression vector (as described above), the expression vector is introduced into a host cell (as described above) and the non-phosphorylatable PPAR gamma protein is expressed in the host cell. The non-phosphorylatable PPAR gamma protein can then be isolated from the cells by an appropriate purification scheme using standard protein purification techniques. Alternative to recombinant expression, a non-phosphorylatable PPAR gamma protein, polypeptide, or peptide can be synthesized chemically using standard peptide synthesis techniques. Moreover, native non-phosphorylatable PPAR gamma protein can be isolated from cells (e.g., brown adipocytes), for example using an anti-non-phosphorylatable PPAR gamma antibody (described further below).

The invention also provides non-phosphorylatable PPAR gamma chimeric or fusion proteins. As used herein, a non-phosphorylatable PPAR gamma "chimeric protein" or "fusion protein" comprises a non-phosphorylatable PPAR gamma polypeptide operatively linked to a non-non-phosphorylatable PPAR gamma polypeptide. A "non-phosphorylatable PPAR gamma polypeptide" refers to a polypeptide having an amino acid sequence corresponding to non-phosphorylatable PPAR gamma, whereas a "non-non-phosphorylatable PPAR gamma polypeptide" refers to a polypeptide having an amino acid sequence corresponding to a protein which is not substantially homologous to the non-phosphorylatable PPAR gamma protein, e.g., a protein which is different from the non-phosphorylatable PPAR gamma protein and which is derived from the same or a different organism. Within the fusion protein, the term "operatively linked" is intended to indicate that the non-phosphorylatable PPAR gamma polypeptide and the non-non-phosphorylatable PPAR gamma polypeptide are fused in-frame to each other. The non-non-phosphorylatable PPAR gamma polypeptide can be fused to the N-terminus or C-terminus of the non-phosphorylatable PPAR gamma polypeptide. For example, in one embodiment the fusion protein is a GST-non-phosphorylatable PPAR gamma fusion protein in which the non-phosphorylatable PPAR gamma sequences are fused to the C-terminus of the GST sequences. Such fusion proteins can facilitate the purification of recombinant non-phosphorylatable PPAR gamma. In another embodiment, the fusion protein is a non-phosphorylatable PPAR gamma protein containing a heterologous signal sequence at its N-terminus. In certain host cells (e.g., mammalian host cells), expression and/or secretion of non-phosphorylatable PPAR gamma can be increased through use of a heterologous signal sequence.

A non-phosphorylatable PPAR gamma chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A non-phosphorylatable PPAR gamma-encoding nucleic acid can be cloned into such an expression vector such that the fusion moiety is linked in-frame to the non-phosphorylatable PPAR gamma protein.

The present invention, at least in part, also pertains to homologues of the non-phosphorylatable PPAR gamma proteins which function as either a non-phosphorylatable PPAR gamma agonist (mimetic) or a non-phosphorylatable PPAR gamma antagonist. In a certain embodiments, the non-phosphorylatable PPAR gamma agonists and antagonists stimulate or inhibit, respectively, a subset of the biological activities of the naturally occurring form of the non-phosphorylatable PPAR gamma protein. Thus, specific biological effects can be elicited by treatment with a homologue of limited function. In one embodiment, treatment of a subject with a homologue having a subset of the biological activities of the naturally occurring form of the protein has fewer side effects in a subject relative to treatment with the naturally occurring form of the non-phosphorylatable PPAR gamma protein.

Homologues of the non-phosphorylatable PPAR gamma protein can be generated by mutagenesis, e.g., discrete point mutation or truncation of the non-phosphorylatable PPAR gamma protein. As used herein, the term "homologue" refers to a variant form of the non-phosphorylatable PPAR gamma protein which acts as an agonist or antagonist of the activity of the non-phosphorylatable PPAR gamma protein. An agonist of the non-phosphorylatable PPAR gamma protein can retain substantially the same, or a subset, of the biological activities of the non-phosphorylatable PPAR gamma protein.

In an alternative embodiment, homologues of the non-phosphorylatable PPAR gamma protein can be identified by screening combinatorial libraries of mutants, e.g., truncation mutants, of the non-phosphorylatable PPAR gamma protein for non-phosphorylatable PPAR gamma protein agonist or antagonist activity. In one embodiment, a variegated library of non-phosphorylatable PPAR gamma variants is generated by combinatorial mutagenesis at the nucleic acid level and is encoded by a variegated gene library. A variegated library of non-phosphorylatable PPAR gamma variants can be produced by, for example, enzymatically ligating a mixture of synthetic oligonucleotides into gene sequences such that a degenerate set of potential non-phosphorylatable PPAR gamma sequences is expressible as individual polypeptides, or alternatively, as a set of larger fusion proteins (e.g., for phage display) containing the set of non-phosphorylatable PPAR gamma sequences therein. There are a variety of methods which can be used to produce libraries of potential non-phosphorylatable PPAR gamma homologues from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential non-phosphorylatable PPAR gamma sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of the non-phosphorylatable PPAR gamma protein coding can be used to generate a variegated population of non-phosphorylatable PPAR gamma fragments for screening and subsequent selection of homologues of a non-phosphorylatable PPAR gamma protein. In one embodiment, a library of coding sequence fragments can be generated by treating a double stranded PCR fragment of a non-phosphorylatable PPAR gamma coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the non-phosphorylatable PPAR gamma protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of non-phosphorylatable PPAR gamma homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify non-phosphorylatable PPAR gamma homologues (Arkin and Youvan (1992) *Proc. Natl. Acad. Sci. USA* 89:7811-7815; Delagrave et al. (1993) *Protein Engineering* 6(3):327-331).

In one embodiment, an isolated non-phosphorylatable PPAR gamma protein, or a portion or fragment thereof, can be used as an immunogen to generate antibodies that bind non-phosphorylatable PPAR gamma using standard techniques for polyclonal and monoclonal antibody preparation. For example, a peptide having the sequence, KTTDK(pS) PFVIYDC (SEQ ID NO: 14), with or without serine phosphorylation, can be used for this purpose. Alternatively, the full-length non-phosphorylatable PPAR gamma protein can be used or, alternatively, antigenic peptide fragments of non-phosphorylatable PPAR gamma can be used as immunogens. A non-phosphorylatable PPAR gamma immunogen typically is used to prepare antibodies by immunizing a suitable subject, (e.g., rabbit, goat, mouse or other mammal) with the immunogen. An appropriate immunogenic preparation can contain, for example, recombinantly expressed non-phosphorylatable PPAR gamma protein or a chemically synthesized non-phosphorylatable PPAR gamma peptide. The preparation can further include an adjuvant, such as Freund's complete or incomplete adjuvant, or similar immunostimulatory agent. Immunization of a suitable subject with an immunogenic non-phosphorylatable PPAR gamma preparation induces a polyclonal anti-non-phosphorylatable PPAR gamma antibody response.

Accordingly, another aspect of the invention pertains to the use of anti-non-phosphorylatable PPAR gamma antibodies. The term "antibody" as used herein refers to immunoglobulin molecules and immunologically active portions of immunoglobulin molecules, i.e., molecules that contain an antigen binding site which specifically binds (immunoreacts with) an antigen, such as non-phosphorylatable PPAR gamma. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind non-phosphorylatable PPAR gamma. The term "monoclonal antibody" or "monoclonal antibody composition", as used herein, refers to a population of antibody molecules that contain only one species of an antigen binding site capable of immunoreacting with a particular epitope of non-phosphorylatable PPAR gamma. A monoclonal antibody composition thus typically displays a single binding affinity for a particular non-phosphorylatable PPAR gamma protein with which it immunoreacts.

Polyclonal anti-non-phosphorylatable PPAR gamma antibodies can be prepared as described above by immunizing a suitable subject with a non-phosphorylatable PPAR gamma immunogen. The anti-non-phosphorylatable PPAR gamma antibody titer in the immunized subject can be monitored over time by standard techniques, such as with an enzyme linked immunosorbent assay (ELISA) using immobilized non-phosphorylatable PPAR gamma. If desired, the antibody molecules directed against non-phosphorylatable PPAR gamma can be isolated from the mammal (e.g., from the blood) and further purified by well known techniques, such as protein A chromatography to obtain the IgG fraction. At an appropriate time after immunization, i.e., when the anti-non-phosphorylatable PPAR gamma antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer*) 29:269-75), the more recent human B cell hybridoma technique (Kozbor et al. (1983) *Immunol. Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387-402; M. L. Gefter et al. (1977) *Somatic Cell Genet.* 3:231-36). Briefly, an immortal cell line (typically a myeloma) is fused to lymphocytes (typically splenocytes) from a mammal immunized with a non-phosphorylatable PPAR gamma immunogen as described above, and the culture supernatants of the resulting hybridoma cells are screened to identify a hybridoma producing a monoclonal antibody that binds non-phosphorylatable PPAR gamma.

Any of the many well-known protocols used for fusing lymphocytes and immortalized cell lines can be applied for the purpose of generating an anti-non-phosphorylatable PPAR gamma monoclonal antibody (see, i.e., G. Galfre et al.

(1977) *Nature* 266:550-52; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention, at least in part, with an immortalized mouse cell line. In some embodiments, immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, i.e., the P3-NS1/1-Ag4-1, P3-x63-Ag8.653 or Sp2/O—Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind non-phosphorylatable PPAR gamma, i.e., using a standard ELISA assay.

Alternative to preparing monoclonal antibody-secreting hybridomas, a monoclonal anti-non-phosphorylatable PPAR gamma antibody can be identified and isolated by screening a recombinant combinatorial immunoglobulin library (e.g., an antibody phage display library) with non-phosphorylatable PPAR gamma to thereby isolate immunoglobulin library members that bind non-phosphorylatable PPAR gamma. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1369-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clackson et al. (1991) *Nature* 352:624-628; Gram et al. (1992) *Proc. Natl. Acad. Sci. USA* 89:3576-3580; Garrard et al. (1991) *Bio/Technology* 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. *Nature* (1990) 348:552-554.

Additionally, recombinant anti-non-phosphorylatable PPAR gamma antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

An anti-non-phosphorylatable PPAR gamma antibody (e.g., monoclonal antibody) can be used to isolate non-phosphorylatable PPAR gamma by standard techniques, such as affinity chromatography or immunoprecipitation. An anti-non-phosphorylatable PPAR gamma antibody can facilitate the purification of natural non-phosphorylatable PPAR gamma from cells and of recombinantly produced non-phosphorylatable PPAR gamma expressed in host cells. Moreover, an anti-non-phosphorylatable PPAR gamma antibody can be used to detect non-phosphorylatable PPAR gamma protein (e.g., in a cellular lysate or cell supernatant) in order to evaluate the abundance and pattern of expression of the non-phosphorylatable PPAR gamma protein. Anti-non-phosphorylatable PPAR gamma antibodies can be used to monitor protein levels in a cell or tissue, e.g., adipose cells or tissue, as part of a clinical testing procedure, e.g., in order to monitor a safe dosage of an uncoupling agent. Detection can be facilitated by coupling (e.g., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and acquorin, and examples of suitable radioactive material include $^{125}$I, $^{131}$I, $^{35}$S or $^3$H.

In vivo techniques for detection of non-phosphorylatable PPAR gamma protein include introducing into a subject a labeled antibody directed against the protein. For example, the antibody can be labeled with a radioactive biomarker whose presence and location in a subject can be detected by standard imaging techniques.

IV. Methods and Compounds of the Invention

The methods of the invention relate to the identification and use of PPAR gamma ligands that selectively promote anti-metabolic disorder activity over classical PPAR gamma activation. Such ligands are referred to herein as "atypical."

The term "selectively promotes" is intended to encompass any differential regulation of PPAR gamma activity that promotes, activates, stimulates, enhances, or results in promotion of genes regulated predominantly and/or exclusively through cdk5-mediated phosphorylation of PPAR gamma, such as "anti-diabetic" and/or "brown fat" and/or "increased respiration/oxygen consumption" genes (e.g., those selectively promoted by the atypical PPAR gamma ligand, MRL24), in contrast to promoting metabolic disorders, such as "adipogenic" genes (e.g., those regulated by the classical PPAR gamma agonist, rosiglitazone). In another aspect, the invention is related to methods for identifying such genes regulated predominantly and/or exclusively through cdk5-mediated phosphorylation of PPAR gamma, such as "anti-diabetic" and/or "brown fat" and/or "increased respiration/oxygen consumption" genes, such as those selectively promoted by the atypical PPAR gamma ligand, MRL24, by assaying gene expression profiles of samples, for example, in the presence or absence of test compounds that selectively inhibit PPAR gamma phosphorylation or in the presence or absence (wild type PPR gamma) of non-phosphorylatable PPAR gamma. In another aspect, the invention relates to methods for treating metabolic disorders, e.g., diabetes and/or obesity, in a subject comprising administering to the subject an agent that selectively regulates genes predominantly and/or exclusively through cdk5-mediated phosphorylation of PPAR gamma, such as "anti-diabetic" and/or "brown fat" and/or "increased respiration/oxygen consumption" genes, such as those selectively promoted by the atypical PPAR gamma ligand, MRL24.

As used herein, the term "agent" and "therapeutic agent" is defined broadly as anything that cells from a subject with obesity or an obesity-related disorder may be exposed to in a therapeutic protocol.

A. PPAR Gamma Ligand Screening Assays

The invention provides methods for identifying compounds or agents which can selectively promote anti-metabolic disorder activity over classical PPAR gamma activation, such as atypical PPAR gamma ligands. These methods are also referred to herein as drug screening assays and typically include the step of screening a candidate/test compound or agent for the ability to interact with (e.g., bind to) a PPAR gamma protein, to modulate the interaction of a PPAR gamma protein and a target molecule, and/or to modulate PPAR gamma nucleic acid expression and/or PPAR gamma protein activity. Candidate/test compounds or agents which have one or more of these abilities can be used as drugs to treat disorders characterized by aberrant, abnormal, and/or unwanted PPAR gamma nucleic acid expression and/or PPAR gamma protein activity. Candidate/test compounds include, for example, small organic and inorganic molecules (e.g., molecules obtained from combinatorial and natural product libraries).

The test compounds of the present invention, at least in part, can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner USP '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222: 301-310); (Ladner supra.).

In one embodiment, the invention provides assays for screening candidate/test compounds which interact with (e.g., bind to) PPAR gamma protein. Typically, the assays are cell-based assays. The cell, for example, can be of mammalian origin, e.g., a liver cell, a skeletal muscle cell, immune cell, such as a monocyte or macrophage, or a fat cell, such as a preadipocyte, white adipocyte, and/or brown adipocyte, In other embodiments, the cell can endogenously harbor non-phosphorylatable PPAR gamma encoding nucleic acid sequences, such as in the case of knock-in animals described herein.

In other embodiments, the assays are cell-free assays which include the steps of combining a PPAR gamma protein or a biologically active portion thereof, and a candidate/test compound, e.g., under conditions which allow for interaction of (e.g., binding of) the candidate/test compound to the PPAR gamma protein or portion thereof to form a complex, and detecting the formation of a complex, in which the ability of the candidate compound to interact with (e.g., bind to) the PPAR gamma polypeptide or fragment thereof is indicated by the presence of the candidate compound in the complex. Formation of complexes between the PPAR gamma protein and the candidate compound can be quantitated, for example, using standard immunoassays. Such analyses would identify test compounds as PPAR gamma ligands.

In another embodiment, the invention provides screening assays to identify candidate/test compounds which modulate (e.g., stimulate or inhibit) the interaction (and most likely PPAR gamma activity as well) between a PPAR gamma protein and a molecule (target molecule) with which the PPAR gamma protein normally interacts. Examples of such target molecules include proteins in the signaling pathway promoting anti-metabolic disorder activity by PPAR gamma over classical PPAR gamma activation Typically, the assays are cell-free assays which include the steps of combining a PPAR gamma protein or a biologically active portion thereof, a PPAR gamma target molecule and a candidate/test compound, e.g., under conditions wherein but for the presence of the candidate compound, along with known modulators and/or cofactors, such as cdk5 and/or p35/p25 that bind to or modulate the target molecule, and detecting the formation of a complex which includes the PPAR gamma protein and the target molecule or detecting the interaction/reaction of the PPAR gamma protein and the target molecule. Detection of complex formation can include direct quantitation of the complex by, for example, measuring inductive effects of the PPAR gamma protein. A statistically significant change, such as a decrease, in the interaction of the PPAR gamma and target molecule (e.g., in the formation of a complex between the PPAR gamma and the target molecule) in the presence of a candidate compound (relative to what is detected in the absence of the candidate compound) is indicative of a modulation (e.g., stimulation or inhibition) of the interaction between the PPAR gamma protein and the target molecule. Modulation of the formation of complexes between the PPAR gamma protein and the target molecule can be quantitated using, for example, an immunoassay.

To perform the above drug screening assays, it is desirable to immobilize either PPAR gamma or its target molecule to facilitate separation of complexes from uncomplexed forms of one or both of the proteins, as well as to accommodate automation of the assay. Interaction (e.g., binding of) of PPAR gamma to a target molecule, in the presence and absence of a candidate compound, can be accomplished in any vessel suitable for containing the reactants. Examples of such vessels include microtitre plates, test tubes, and microcentrifuge tubes. In one embodiment, a fusion polypeptide can be provided which adds a domain that allows the polypeptide to be bound to a matrix. For example, glutathione-S-transferase/PPAR gamma fusion polypeptides can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of PPAR gamma-binding polypeptide found in the bead fraction quantitated from the gel using standard electrophoretic techniques.

Other techniques for immobilizing polypeptides on matrices can also be used in the exemplary drug screening assays of the invention. For example, either PPAR gamma or its target molecule can be immobilized utilizing conjugation of biotin and streptavidin. Biotinylated PPAR gamma molecules can be prepared from biotin-NHS(N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with PPAR gamma, such as phospher-Ser-273-specific anti-PPAR gamma antibodies, but which do not interfere with binding of the polypeptide to its target molecule can be derivatized to the wells of the plate, and PPAR gamma trapped in the wells by antibody conjugation. As described above, preparations of a PPAR gamma-binding polypeptide and a candidate compound are incubated in the PPAR gamma-presenting wells of the plate, and the amount of complex trapped in the well can be quantitated. Methods for detecting such complexes, in addition to those described above for the GST-immobilized complexes, include immunodetection of complexes using antibodies reactive with the PPAR gamma target molecule, or which are reactive with PPAR gamma polypeptide and compete with the target molecule; as well as enzyme-linked assays which rely on detecting an enzymatic activity associated with the target molecule.

In yet another embodiment, the invention provides a method for identifying a compound or agent (e.g., a screening assay) capable of selectively promoting anti-metabolic disorder activity over classical PPAR gamma activation. Such compounds would also be useful for the treatment of a metabolic disorder, as described further herein. Methods for assaying the ability of the compound or agent to modulate the expression of the PPAR gamma nucleic acid or activity of the PPAR gamma protein can be cell-free or cell-based assays.

Accordingly, the samples can comprise in vitro, ex vivo, and/or in vivo samples. Such samples can also be selected from any number of cell types relevant for metabolic disorder analyses, including, for example, preadipocytes, white adipocytes, brown adipocytes, monocytes, and macrophages.

In addition, the cell-free and/or cell-based assays described herein can be used according to methods well-known to the skilled artisan for determining the effect of a compound or agent to differentially regulate PPAR gamma activity that promotes, activates, stimulates, enhances, or results in promotion of genes regulated predominantly and/or exclusively through cdk5-mediated phosphorylation of PPAR gamma, such as "anti-diabetic" and/or "brown fat" and/or "increased respiration/oxygen consumption" genes, such as those selectively promoted by the atypical PPAR gamma ligand, MRL24, in contrast to promoting metabolic disorders, such as "adipogenic" genes especially those regulated by the classical PPAR gamma agonist, rosiglitazone. This can involve identifying genes regulated predominantly and/or exclusively through cdk5-mediated phosphorylation of PPAR gamma, such as "anti-diabetic" and/or "brown fat" and/or "increased respiration/oxygen consumption" genes, according to methods well known in the art. Such genes can be analyzed in their endogenous cellular contexts or assayed according to any of a number of well-known gene reporter systems, such as using transcriptional assays operatively-linked to PPAR gamma responsive promoters, PPAR gamma transactivation assays (e.g., GAL4-PPAR gamma on a upstream activation site (UAS) promoter), etc.

Candidate compounds which produce a statistically significant change in PPAR gamma-dependent responses (either stimulation or inhibition) can be identified. Such statistically significant changes can be measured according to a number of criteria and/or relative to a number of controls. For example, significant modulation of gene expression, assay change, etc. can be assessed if the output under analysis is greater than or less than 1.1-, 1.2-, 1.3-, 1.4-, 1.5-, 1.6-, 1.7-, 1.8-, 1.9-, 2.0-, 2.1-, 2.2-, 2.3-, 2.4-, 2.5-, 2.6-, 2.7-, 2.8-, 2.9-, 3.0-, 3.1-, 3.2-, 3.3-, 3.4-, 3.5-, 3.6-, 3.7-, 3.8-, 3.9-, 4.0-, 4.1-, 4.2-, 4.3-, 4.4-, 4.5-, 4.6-, 4.7-, 4.8-, 4.9-, 5.0-, 5.5-, 6.0, 6.5-, 7.0-, 7.5-, 8.0-, 8.5-, 9.0- 9.5-, 10-, 11-, 12-, 13-, 14-, 15-, 16-, 17-, 18-, 19-, 20-fold or more different (including any range inclusive), relative to a control.

Generally, determining expression profiles can be performed using arrays involving the following steps: (a) obtaining an RNA sample from a subject and preparing labeled nucleic acids therefrom (the "target nucleic acids" or "targets"); (b) contacting the target nucleic acids with the array under conditions sufficient for target nucleic acids to bind with corresponding probes on the array, e.g., by hybridization or specific binding; (c) optionally removing unbound targets from the array; (d) detecting bound targets, and (e) analyzing the results. As used herein, "nucleic acid probes" or "probes" are nucleic acids attached to the array, whereas "target nucleic acids" are nucleic acids that are hybridized to the array. Each of these steps and methods and variations for carrying them out are well known to a skilled artisan.

In certain embodiments, it is sufficient to determine the expression of a relatively small number of genes (e.g., one or only a few genes), as opposed to hundreds or thousands of genes. Although microarrays can be used in these embodiments, various other methods of detection of gene expression are available. Although certain similarities with array-based detection, such as RNA isolation, labeling, etc. may be common, the following methods can offer advantages in terms of ease-of-use and time constraints.

In one embodiment, RNA obtained form a sample is reverse transcribed into a first cDNA strand and subjected to PCR, e.g., RT-PCR. House keeping genes, or other genes whose expression does not vary can be used as internal controls and controls across experiments. Following the PCR reaction, the amplified products can be separated by electrophoresis and detected. By using quantitative PCR, the level of amplified product will correlate with the level of RNA that was present in the sample. The amplified samples can also be separated on a agarose or polyacrylamide gel, transferred onto a filter, and the filter hybridized with a probe specific for the gene of interest. Numerous samples can be analyzed simultaneously by conducting parallel PCR amplification, e.g., by multiplex PCR.

Quantitative PCR techniques can also be used based on numerous technologies, such as TaqMan or probes labeled at the 5' and 3' ends with a reporter and quencher fluorescent dye, respectively (FQ probe), which anneals between the two PCR primers. Only specific product will be detected when the probe is bound between the primers. As PCR amplification proceeds, the 5'-nuclease activity of Taq polymerase initially cleaves the reporter dye from the probe. The signal generated when the reporter dye is physically separated from the quencher dye is detected by measuring the signal with an attached CCD camera. Each signal generated equals one probe cleaved which corresponds to amplification of one target strand. PCR reactions may be set up using the PE Applied Biosystem TaqMan PCR Core Reagent Kit according to the instructions supplied. This technique is further described, e.g., in U.S. Pat. No. 6,326,462.

In other embodiments, dot blot, "sandwich" hybridization, deep sequencing, SAGE, Northern blotting, in situ hybridization, and other similar methods can be used, especially as further described, for example, in Sambrook et al., "Molecular Cloning: A Laboratory Manual" (New York, Cold Spring Harbor Laboratory, 1989).

In other methods, the level of expression of a gene can be detected by measuring the level of protein encoded by the gene. This can be done, e.g., by immunoprecipitation, ELISA, or immunohistochemistry using an agent, e.g., an antibody, that specifically detects the protein encoded by the gene. Other techniques include Western blot analysis. Immunoassays are commonly used to quantitate the levels of proteins in cell samples, and many other immunoassay techniques are known in the art. The invention is not limited to a particular assay procedure, and therefore is intended to include both homogeneous and heterogeneous procedures. Exemplary immunoassays which can be conducted according to the invention include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA), ELISA, etc. alone or in combination or alternatively with NMR, MALDI-TOF, LC-MS/MS. An indicator moiety, or label group, can be attached to the subject antibodies and is selected so as to meet the needs of various uses of the method which are often dictated by the availability of assay equipment and compatible immunoassay procedures. General techniques to be used in performing the various immunoassays noted above are known to those of ordinary skill in the art.

In the case of polypeptides which are secreted from cells, such as adipokines, such as adiponectin, or obesity-induced inflammation proteins, such as TNF-alpha, the level of expression of these polypeptides can be measured in biological fluids.

Complementing such gene expression analyses, assays that phenotypically report markers of metabolic disorder activity can also be performed. For example, assays reporting the induction of anti-metabolic disorder activity such as anti-obesity, anti-diabetes, brown fat induction (e.g., in white fat cells and/or de novo from preadipocytes), etc. can be assessed according to expression of brown fat specific genes, including UCP-1, cidea, and PGC-1a, as well as genes involved in mitochondrial biogenesis and uncoupled oxygen consumption. In other embodiments, phenotypic assays for brown fat induction can also be assessed, such as analyzing histology, uncoupled oxygen consumption, uncoupled respiration by mitochondria, fatty acid beta oxidation, thermogenesis (heat production), respiration measurements, weight changes, fluid retention, mitochondrial biogenesis, energy expenditure, adipogenesis, serum fatty acid levels, serum adipokine levels, white and/or brown fat depots, fat and/or lean mass (e.g., as assayed by dual energy X-ray absorptiometry (DEXA) scanning), glucose tolerance tests, insulin tolerance tests, and modulation of obesity-induced inflammation.

In yet another aspect of the invention, the PPAR gamma proteins can be used as "bait proteins" in two-hybrid, three-hybrid, etc. assays (see, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent WO 94/10300), to identify other proteins, which bind to or interact with PPAR gamma ("PPAR gamma-binding proteins" or "PPAR gamma-bp") and selectively modulate PPAR gamma activity that promotes anti-metabolic activities over classical PPAR gamma activation. Such interactions can comprise ligand-dependent or ligand-independent methods.

In all of these methods, the use of proper controls can be important. In one embodiment, atypical PPAR gamma modulators of the present invention, at least in part, can be identified in a method as described herein such that the assay output (e.g., the genes and assays listed in Tables 1 and 2) is compared relative to a cell in the absence of the candidate compound. In one embodiment, comparison can be made relative to a cell contacted with a known PPAR gamma agonist, such as the robust classical PPAR gamma agonist, rosiglitazone. In another embodiment, comparison can be made relative to a cell comprising encoding and/or expressing a non-phosphorylatable PPAR gamma polypeptide (e.g., a S273A mutant). In still another embodiment, comparison can be made relative to ratios of gene expression an analyses, for example, the ratio of expression of a gene listed in Table 1 relative to that of a gene listed in Table 2 or vice versa.

B. Compounds

PPAR gamma ligands known in the art and/or identified using the methods described herein, as well as endpoints analyzed using the methods described herein, can be described according to a number of criteria. For example, the compound or agents can have less than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or less of the classical PPAR agonist activity (or any range inclusive) relative to another PPAR gamma agonist, such as the robust classical PPAR gamma agonist, rosiglitazone. Besides rosiglitazone, other classical PPAR gamma agonists, such as pioglitazone, can be used. In some embodiments, the classical PPAR agonist activity can be measured according to methods described herein, including, for example, analyzing gene expression of biomarkers listed in Tables 1 and 2. For example, significant modulation of gene expression, assay change, etc. can be assessed if the output under analysis is greater than or less than 1.1-, 1.2-, 1.3-, 1.4-, 1.5-, 1.6-, 1.7-, 1.8-, 1.9-, 2.0-, 2.1-, 2.2-, 2.3-, 2.4-, 2.5-, 2.6-, 2.7-, 2.8-, 2.9-, 3.0-, 3.1-, 3.2-, 3.3-, 3.4-, 3.5-, 3.6-, 3.7-, 3.8-, 3.9-, 4.0-, 4.1-, 4.2-, 4.3-, 4.4-, 4.5-, 4.6-, 4.7-, 4.8-, 4.9-, 5.0-, 5.5-, 6.0, 6.5-, 7.0-, 7.5-, 8.0-, 8.5-, 9.0- 9.5-, 10-, 11-, 12-, 13-, 14-, 15-, 16-, 17-, 18-, 19-, 20-fold or more, different (including any range inclusive) relative to a control.

In another embodiment, the compound or agent can have an EC50 binding affinity for PPAR gamma at a dose of 100 µM, 90 µM, 80 µM, 70 µM, 60 µM, 50 µM, 40 µM, 30 µM, 20 µM, 10 µM, 9 µM, 8 µM, 7 µM, 6 µM, 5 µM, 4.5 µM, 4 µM, 3.5 µM, 3 µM, 2.5 µM, 2 µM, 1.5 µM, 1 µM, 900 nM, 850 nM, 800 nM, 750 nM, 700 nM, 650 nM, 600 nM, 550 nM, 500 nM, 450 nM, 400 nM, 350 nM, 300 nM, 250 nM, 200 nM, 150 nM, 100 nM, 95 nM, 90 nM, 85 nM, 80 nM, 75 nM, 70 nM, 65 nM, 60 nM, 55 nM, 50 nM, 45 nM, 40 nM, 35 nM, 30 nM, 25 nM, 20 nM, 15 nM, 10 nM, 5 nM, 4 nM, 3 nM, 2 nM, 1 nM or less (or any range inclusive). An $EC_{50}$ value may be determined and used for comparative purposes. This value is the concentration of drug needed to inhibit a relevant PPAR gamma function by 50% relative to the control.

In still another embodiment, the compound or agent can stabilize certain domains of the PPAR gamma polypeptide, for example, as measured using HDX techniques. Without being bound by theory, it is believed that helix 12 is only stabilized by classical PPAR agonists (i.e., strong/full), whereas atypical PPAR agonists (i.e., partial/intermediate) agonists, such as compounds and agents obtained using the screening methods described herein, do not exhibit statistically significant stabilization patterns of helix 12. In one embodiment, by contrast, the atypical agonists stabilize the beta sheet. In another embodiment, the atypical agonists stabilize helix 3. Assays to determine protein domain stabilization are well known in the art and described, for example, in Bruning et al. (2007) Structure 15:1258-1271, which is incorporated in its entirety herein by this reference. In some embodiments, the compound or agent can stabilize the beta sheet and/or helix 3 by at least 100%, 95%, 90%, 95%, 90%, 85%, 80%, 75%, 70%, 65%, 60%, 55%, 50%, 45%, 40%, 35%, 30%, 25%, 20% (or any range inclusive) relative to control (e.g., a known atypical PPAR gamma agonist such as MRL24 and/or MRL-20).

In yet another embodiment, the compound or agent can belong to a structural class of compounds, such as a family of small molecules. Examples of classical PPAR gamma ligands that act as strong agonists include thizolidinediones (TZD) and thiazolidine derivatives known as thiazolidinediones, e.g., proglitazone (also known as AD-4833 and U-72107E), troglitazone (also known as CS-045) (Sankyo) and CI-991 (Parke-Davis), BRL 49653, ciglitazone, englitazone and chemical derivatives thereof. These compounds are conventionally known for the treatment of diabetes. See e.g., U.S. Pat. Nos. 4,812,570; 4,775,687; 4,725,610; 4,582,839; and 4,572,912 for exemplary sources of such compounds. U.S. Pat. No. 5,521,201 and European Patent Applications 0008203, 0139421, 0155845, 0177353, 0193256, 0207581 and 0208420, and Chem. Pharm. Bull 30 (10) 3580-3600 relate to thiazolidinedione derivatives, and describe commercial sources/synthetic schemes for a variety of TZD and TZD-like analogs, which may be useful in carrying out the methods of the present invention, at least in part. By contrast, examples of atypical PPAR gamma ligands that selectively promote anti-metabolic activities over classical PPAR gamma activation include MRL-20, MRL-24, nTZDpa, SR145, SR147, Mbx-102, and BVT.13, as described, for example, in Bruning et al. (2007) Structure 15:1258-1271, which is incorporated in its entirety herein by this reference C. Methods of Treatment Atypical PPAR gamma modulators of the present invention, at least in part, can be used to treat, for example, metabolic disorders described herein, including weight disorders, e.g., obesity, and disorders associated with insufficient insulin activity, e.g., diabetes. In some embodiments, such PPAR gamma modulators can also be used to determine the efficacy, toxicity, or side effects of treatment with such an agent. These methods of treatment generally include the steps of administering atypical PPAR gamma modulators in a pharmaceutical composition, as described in subsection V below, to a subject in need of such treatment, e.g., a subject with a disorder described herein.

The term "administering" is intended to include routes of administration which allow the agent to perform its intended function of increasing non-phosphorylatable PPAR gamma expression and/or activity. Examples of routes of administration which can be used include injection (subcutaneous, intravenous, parenterally, intraperitoneally, intrathecal, etc.), oral, inhalation, and transdermal. The injection can be bolus injections or can be continuous infusion. Depending on the route of administration, the agent can be coated with or disposed in a selected material to protect it from natural conditions which may detrimentally affect its ability to perform its intended function. The agent may be administered alone, or in conjunction with a pharmaceutically acceptable carrier. Further the agent may be coadministered with a pharmaceutically acceptable carrier. The agent also may be administered as a prodrug, which is converted to its active form in vivo.

The term "effective amount" of an agent that induces non-phosphorylatable PPAR gamma expression and/or activity is that amount necessary or sufficient to promote non-phosphorylatable PPAR gamma expression and/or activity in the subject or population of subjects. The effective amount can vary depending on such factors as the type of therapeutic agent(s) employed, the size of the subject, or the severity of the disorder.

It will be appreciated that individual dosages may be varied depending upon the requirements of the subject in the judgment of the attending clinician, the severity of the condition being treated and the particular compound being employed. In determining the therapeutically effective amount or dose, a number of additional factors may be considered by the attending clinician, including, but not limited to: the pharmacodynamic characteristics of the particular agent and its mode and route of administration; the desired time course of treatment; the species of mammal; its size, age, and general health; the specific disease involved; the degree of or involvement or the severity of the disease; the response of the individual subject; the particular compound administered; the mode of administration; the bioavailability characteristics of the preparation administered; the dose regimen selected; the kind of concurrent treatment; and other relevant circumstances.

Treatment can be initiated with smaller dosages which are less than the effective dose of the compound. Thereafter, in one embodiment, the dosage should be increased by small increments until the optimum effect under the circumstances is reached. For convenience, the total daily dosage may be divided and administered in portions during the day if desired.

The effectiveness of any particular agent to treat metabolic disorders can be monitored by comparing two or more samples obtained from a subject undergoing anti-metabolic disorder treatment. In general, a first sample is obtained from the subject prior to beginning therapy and one or more samples during treatment. In such a use, a baseline of expression of cells from subjects with metabolic disorders prior to therapy is determined and then changes in the baseline state of expression of cells from subjects with metabolic disorders is monitored during the course of therapy. Alternatively, two or more successive samples obtained during treatment can be used without the need of a pre-treatment baseline sample. In such a use, the first sample obtained from the subject is used as a baseline for determining whether the expression of cells from subjects with metabolic disorders is increasing or decreasing.

Another aspect of the invention relates to a method for identifying a compound or agent (e.g., peptides, peptidomimetics, small molecules or other drugs) capable of inducing the expression and/or activity of non-phosphorylatable PPAR gamma.

V. Pharmaceutical Compositions

In another aspect, the present invention, at least in part, provides pharmaceutically acceptable compositions which comprise a therapeutically-effective amount of an agent that selectively promotes anti-metabolic disorder activity over classical PPAR gamma activation, formulated together with one or more pharmaceutically acceptable carriers (additives) and/or diluents. As described in detail below, the pharmaceutical compositions of the present invention, at least in part, may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that selectively promotes anti-metabolic disorder activity over classical PPAR gamma activation, which is effective for producing some desired therapeutic effect, e.g., weight loss, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that induce non-phosphorylatable PPAR gamma expression and/or activity encompassed by the invention. These salts can be prepared in situ during the final isolation and purification of the agents, or by separately reacting a purified agents agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", *J. Pharm. Sci.* 66:1-19).

In other cases, the agents useful in the methods of the present invention, at least in part, may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that induce non-phosphorylatable PPAR gamma expression and/or activity. These salts can likewise be prepared in situ during the final isolation and purification of the agents, or by separately reacting the purified agents agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention, at least in part, include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, for example, from about 5 percent to about 70 percent, from about 10 percent to about 30 percent.

Methods of preparing these formulations or compositions include the step of bringing into association an agent that induces non-phosphorylatable PPAR gamma expression and/or activity with the carrier and, optionally, one or more accessory ingredients. In general, the formulations are prepared by uniformly and intimately bringing into association a agents agent with liquid carriers, or finely divided solid carriers, or both, and then, if necessary, shaping the product.

Particularly advantageous formulations contemplated for the compounds and compositions of the present invention, at least in part, include oral formulations. Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a agents agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that induces non-phosphorylatable PPAR gamma expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a agents agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that induces non-phosphorylatable PPAR gamma expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that induces non-phosphorylatable PPAR gamma expression and/or activity can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a agents agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that induces non-phosphorylatable PPAR gamma expression and/or activity in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the agents of the present invention, at least in part, are administered as pharmaceuticals, to humans and animals, they can be given per se or as a pharmaceutical composition containing, for example, 0.1 to 99.5% (e.g., 0.5 to 90%) of active ingredient in combination with a pharmaceutically acceptable carrier.

Actual dosage levels of the active ingredients in the pharmaceutical compositions of this invention may be determined by the methods of the present invention, at least in part, so as to obtain an amount of the active ingredient, which is effective to achieve the desired therapeutic response for a particular subject, composition, and mode of administration, without being toxic to the subject.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

TABLE 1

Increased Gene Expression Levels, Activities and/or Assays

| Gene Symbol | Gene Name | GenBank Gene Accession Number | GenBank Protein Accession Number | Gene ID |
|---|---|---|---|---|
| adipsin | complement factor D | e.g., NM_013459.2 and NM_001928.2 | e.g., NP_038487.1 and NP_001919.2 | e.g., 11537 and 1675 |
| fatty acid transporter cd36 | fatty acid transporter/cd36 | e.g., NM_007643.3 and NM_000072.3 and NM_001001547.2 and NM_001001548.2 and NM_001127443.1 and NM_001127444.1 | e.g., NP_031669.2 and NP_000063.2 and NP_001001547.1 and NP_001001548.1 and NP_001120915.1 and NP_001120916.1 | e.g., 12491 and 948 |
| adiponectin | adiponectin | e.g., NM_009605.4 and NM_004797.2 | e.g., NP_0033735.3 and NP_004788.1 | e.g., 11450 and 9370 |
| UCP-1 | uncoupling protein 1 | e.g., NM_009463.3 and NM_021833.4 | e.g., NP_033489.1 and NP_068605.1 | e.g., 22227 and 7350 |
| cidea | cell death-inducing DFFA-like effector a | e.g., NM_007702.2 and NM_001279.3 and NM_198289.2 | e.g., NP_031728.1 and NP_001270.1 and NP_938031.1 | e.g., 12683 and 1149 |
| PGC1a | Peroxisome porliferative activated receptor, gamma, coactivator 1 alpha | e.g., NM_008904.2 and NM_013261.3 | e.g., NP_032930.1 and NP_037393.1 | e.g., 19017 and 10891 |
| Elovl3 | elongation of very long chain fatty acids (FEN1/Elo2, SUR4/Elo3, yeast)-like 3 | e.g., NM_007703.2 and NM_152310.1 | e.g., NP_031729.1 and NP_689523.1 | e.g., 12686 and 83401 |
| C/EBPbeta | CCAAT/enhancer binding protein beta | e.g., NM_009883.3 and NM_005194.2 | e.g., NP_034013.1 and NP_005185.2 | e.g., 12608 and 1051 |
| Cox7a1 | cyotchrome c oxidase subunit VIIa polypeptide 1 | e.g., NM_009944.3 and NM_001864.2 | e.g., NP_034074.1 and NP_001855.1 | e.g., 12865 and 1346 |
| Otopetrin | Otopetrin 1 | e.g., NM_172709.3 and NM_177998.1 | e.g., NP_766297.2 and NP_819056.1 | e.g., 21906 and 133060 |
| Type II deiodinase | Deiodinase, iodothyronine, type II | e.g., NM_010050.2 and NM_000793.4 and NM_001007023.2 and NM_013989.3 | e.g., NP_034180.1 and NP_000784.2 and NP_001007024.1 and NP_054644.1 | e.g., 13371 and 1734 |
| cytochrome C | cytochrome c | e.g., NM_009989.2 and NM_018947.4 | e.g., NP_034119.1 and NP_061820.1 | e.g., 13067 and 54205 |
| cox4i1 | cytochrome c oxidase subunit IV isoform 1 | e.g., NM_009941.2 and NM_001861.2 | e.g., NP_034071.1 and NP_001852.1 | e.g., 12857 and 1327 |
| coxIII | mitochondrially encoded cytochrome c oxidase III | e.g., NC_005089.1 and ENST00000362079 | e.g., NP_904334.1 and ENSP00000354982 | e.g., 17705 and 4514 |
| cox5b | cytochrome c oxidase subunit Vb | e.g., NM_009942.2 and NM_001862.2 | e.g., NP_034072.2 and NP_001853.2 | e.g., 12859 and 1329 |
| cox8b | cytochrome c oxidase subunit 8B, mitochondrial precursor | e.g., NM_007751.3 | e.g., NP_031777.1 | e.g., 12869 and 404544 |
| glut4 | solute carrier family 2 (facilitated glucose transporter), member 4 | e.g., NM_009204.2 and NM_001042.2 | e.g., NP_033230.2 and NP_001033.1 | e.g., 20528 and 6517 |
| atpase b2 | ATPase, H+ transportying, lysosomal 56/58 kDa, V1 subunit B2 | e.g., NM_057213.2 and NM_001693.3 | e.g., NP_476561.1 and NP_001684.2 | e.g., 117596 and 526 |
| coxII | mitochondrially encoded cytochrome c oxidase II | e.g., NC_005089.1 and ENST00000361739 | e.g., NP_904331 and ENSP00000354876 | e.g., 17709 and 4513 |
| atp5o | ATP synthase, H+ transporting, mitochondrial F1 complex, O subunit | e.g., NM_138597.2 and NM_001697.2 | e.g., NP_613063.1 and NP_001688.1 | e.g., 28080 and 539 |
| ndufb5 | NADH dehydrogenase (ubiquinone) 1 beta subcomplex, 5, 16 kDa | e.g., NM_025316.2 and NM_002492.2 | e.g., NP_079592.2 and NP_002483.1 | e.g., 66046 and 4711 |
| Rarres2 | retinoic acid receptor responder (tazarotene induced) 2 | e.g., NM_027852.2 and NM_002889.3 | e.g., NP_082128.1 and NP_002880.1 | e.g., 71660 and 5919 |
| Car3 | carbonic anhydrase 3 | e.g., NM_007606.3 and NM_005181.3 | e.g., NP_031632.2 and NP_005172.1 | e.g., 12350 and 761 |
| Peg10 | paternally expressed 10 | e.g., NM_001040611.1 and NM_001040152.1 and NM_001172437.1 and NM_001172438.1 | e.g., NP_001035701.1 and NP_001035242.1 and NP_001165908.1 and | e.g., 170676 and 23089 |

TABLE 1-continued

| | Increased Gene Expression Levels, Activities and/or Assays | | | |
|---|---|---|---|---|
| | | and NM_015068.3 | NP_001165909.1 and NP_055883.2 | |
| Cidec | Cidec cell death-inducing DFFA-like effector c | e.g., NM_178373.3 and NM_022094.2 | e.g., NP_848460.1 and NP_071377.2 | e.g., 14311 and 63924 |
| Cd24a | CD24a antigen | e.g., NM_009846.2 and NM_013230.2 | e.g., NP_033976.1 and NP_037362.1 | e.g., 12484 and 100133941 |
| Nr1d2 | nuclear receptor subfamily 1, group D, member 2 | e.g., NM_011584.4 and NM_001145425.1 and NM_005126.4 | e.g., NP_035714.3 and NP_001138897.1 and NP_005117.3 | e.g., 353187 and 9975 |
| Ddx17 | DEAD (Asp-Glu-Ala-Asp (SEQ ID NO: 93)) box polypeptide 17 | e.g., NM_001040187.1 and NM_001098504.1 and NM_001098505.1 and NM_006386.4 and NM_030881.3 | e.g., NP_001035277.1 and NP_001091974.1 and NP_001091975.1 and NP_006377.2 and NP_112020.1 | e.g., 67040 and 10521 |
| Aplp2 | amyloid beta (A4) precursor-like protein 2 | e.g., NM_001102455.1 and NM_001142276.1 and NM_001142277.1 and NM_001142278.1 and NM_001642.2 | e.g., NP_001095925.1 and NP_001135748.1 and NP_001135749.1 and NP_001135750.1 and NP_001633.1 | e.g., 11804 and 334 |
| Nr3c1 | nuclear receptor subfamily 3, group C, member 1 | e.g., NM_008173.3 and NM_000176.2 and NM_001018074.1 and NM_001018075.1 and NM_001018076.1 and NM_001018077.1 and NM_001020825.1 and NM_001024094.1 | e.g., NP_032199.3 and NP_000167.1 and NP_001018084.1 and NP_001018085.1 and NP_001018086.1 and NP_001018087.1 and NP_001018661.1 and NP_001019265.1 | e.g., 14815 and 2908 |
| Rybp | RING1 and YY1 binding protein | e.g., NM_019743.3 and NM_012234.4 | e.g., NP_062717.2 and NP_036366.3 | e.g., 56353 and 23429 |
| Txnip | thioredoxin interacting protein | e.g., NM_001009935.2 and NM_006472.3 | e.g., NP_001009935.1 and NP_006463.3 | e.g., 56338 and 10628 |

| Assays |
|---|
| improved stabilization of Helix 3 |
| stabilization of beta sheet |
| Energy expenditure in vivo (including increase O2 consumption and heat production in combination with no change in food intake) |
| Mitochondrial biogenesis |
| Uncoupled oxygen consumption |
| Induction of brown fat program in white fat cells, including histological analysis |
| Fatty acid uptake into cells (monocytes, adipocytes) |

TABLE 2

| Decreased Gene Expression Levels, Activities, and/or Assays | | | | |
|---|---|---|---|---|
| Genes | | | | |
| Gene Symbol | Gene Name | GenBank Gene Accession Number | Gen Bank Protein Accession Number | GeneID |
| Phosphorylated PPAR gamma at Ser-273 or corresponding serine in a homolog | peroxisome proliferator activated receptor gamma | e.g., NM_011146.3 and NM_015869.4 | e.g., NP_035276.2 and NP_056953.2 | e.g., 19016 and 5468 |
| aP2 | adipocyte fatty-acid-binding protein 4 | e.g., NM_024406.1 and NM_001442.2 | e.g., NP_077717.1 and NP_001433.1 | e.g., 11770 and 2167 |
| C/EBPalpha | CCAAT/enhancer binding protein alpha | e.g., NM_007678.3 and NM_004364.3 | e.g., NP_031704.2 and NP_004355.2 | e.g., 12606 and 1050 |
| add1 | adipocyte determination and differentiation factor 1 | e.g., NM_011480.3 and NM_001005291.2 and NM_004176.4 | e.g., NP_035610.1 and NP_00100529.1 and NP_004167.3 | e.g., 20787 and 6720 |
| fatty acid synthase (FAS) | fatty acid synthase | e.g., NM_007988.3 and NM_004104.4 | e.g., NP_032014.3 and NP_004095.4 | e.g., 14104 and 2194 |
| leptin | leptin | e.g., NM_008493.3 and NM_000230.2 | e.g., NP_032519.1 and NP_000221.1 | e.g., 16846 and 3952 |
| LPL | lipoprotein lipase | e.g., NM_008509.2 and NM_000237.2 | e.g., NP_032535.2 and NP_000228.1 | e.g., 16956 and 4023 |

TABLE 2-continued

| | | Decreased Gene Expression Levels, Activities, and/or Assays | | |
|---|---|---|---|---|
| ACC1 | acetyl-coenzyme A carboxylase 1 | e.g., NM_133360.2 and NM_198834.1 and NM_198836.1 and NM_198837.1 and NM_198838.1 and NM_198839.1 | e.g., NP_579938.2 and NP_942131.1 and NP_942133.1 and NP_942134.1 and NP_942135.1 and NP_942136.1 | e.g., 107476 and 31 |
| Cyp2f2 | cytochrome P450, family 2, subfamily f, polypeptide 2 | e.g., NM_007817.2 and NM_000774.3 | e.g., NP_031843.2 and NP_000765.2 | e.g., 13107 and 1572 |
| Selenbp1 | selenium binding protein 1 | e.g., NM_009150.3 and NM_003944.2 | e.g., NP_033176.2 and NP_003935.2 | e.g., 20341 and 8991 |
| Acyl | acyl-Coenzyme A dehydrogenase, very long chain | e.g., NM_017366.2 and NM_000018.2 and NM_001033859.1 | e.g., NP_059062.1 and NP_000009.1 and NP_001029031.1 | e.g., 11370 and 37 |
| Nr1d1 | nuclear receptor subfamily 1, group D, member 1 | e.g., NM_145434.3 and NM_021724.2 | e.g., NP_663409.2 and NP_068370.1 | e.g., 217166 and 9572 |

| Assays |
|---|
| Glucose/insulin tolerance tests |
| Fasting glucose |
| White fat depots including fat mass and lean mass assayed by DEXA scan |
| Serum adipokine levels |
| Serum fatty acid levels |
| adipogenesis |
| Phosphorylation of Ser-273-PPAR gamma (assayed by Western blotting, Immunoprecipitation followed by western blotting, ELISA, NMR, MALDI-TOF mass spectorometry, LC-MS/MS) |
| insulin sensitivity in fat cells (insulin-dependent glucose uptake) |
| transcriptional (reporter gene) assays on PPARgamma responsive promoters |
| transactivation assay of PPAR gamma (GAL4-PPARgamma) on UAS promoter |
| derivation of cell lines from PPAR S273A knock-in mouse |
| use of existing PPARgamma null-cell lines stably expressing wild-type and mutant |
| Suppression of obesity-induced inflammation (TNF-alpha secretion, gene expression of inflammation genes such as MCP1) |

TABLE 3

Primer Sequences

| Gene | Forward primer | Reverse primer |
|---|---|---|
| aP2 | AAGGTGAAGAGCATCATAACCCT | TCACGCCTTTCATAACACATTCC |
| C/EBPα | CAAGAACAGCAACGAGTACCG | GTCACTGGTCAACTCCAGCAC |
| LPL | GGGAGTTTGGCTCCAGAGTTT | TGTGTCTTCAGGGGTCCTTAG |
| Fasn | GCTGGCATTCGTGATGGAGTCGT | AGGCCACCAGTGATGATGTAACTCT |
| CD36 | AAGCTATTGCGACATGATT | GATCCGAACACAGCGTAGAT |
| Glut4 | GTGACTGGAACACTGGTCCTA | CCAGCCACGTTGCATTGTAG |
| Adiponectin | TGTTCCTCTTAATCCTGCCCA | CCAACCTGCACAAGTTCCCTT |
| Adipsin | CATGCTCGGCCCTACATGG | CACAGAGTCGTCATCCGTCAC |
| Resistin | AAGAACCTTTCATTTCCCCTCCT | GTCCAGCAATTTAAGCCAATGTT |
| Angiotensinogen | TCTCCTTACCACAACAAGAGCA | CTTCTCATTCACAGGGGAGGT |
| TNF-α | CCCTCACACTCAGATCATCTTCT | GCTACGACGTGGGCTACAG |
| IL-6 | TAGTCCTTCCTACCCCAATTTCC | TTGGTCCTTAGCCACTCCTTC |
| PAI-1 | TTCAGCCCTTGCTTGCCTC | ACACTTTTACTCCGAAGTCGGT |
| Leptin | GAGACCCCTGTGTCGGTTC | CTGCGTGTGTGAAATGTCATTG |
| PPARγ | GCATGGTGCCTTCGCTGA | TGGCATCTCTGTGTCAACCATG |
| TBP | ACCCTTCACCAATGACTCCTATG | TGACTGCAGCAAATCGCTTGG |

TABLE 3-continued

Primer Sequences

| Gene | Forward primer | Reverse primer |
| --- | --- | --- |
| Cycp2f2 | GTCGGTGTTCACGGTGTACC | AAAGTTCCGCAGGATTTGGAC |
| Rarres2 | GCCTGGCCTGCATTAAAATGG | CTTGCTTCAGAATTGGGCAGT |
| Selenbp2 | ATGGCTACAAAATGCACAAAGTG | CCTGTGTTCCGGTAAATGCAG |
| Car3 | TGACAGGTCTATGCTGAGGGG | CAGCGTATTTTACTCCGTCCAC |
| Peg10 | TGCTTGCACAGAGCTACAGTC | AGTTTGGGATAGGGGCTGCT |
| Cidec | ATGGACTACGCCATGAAGTCT | CGGTGCTAACACGACAGGG |
| Cd24a | GTTGCACCGTTTCCCGGTAA | CCCCTCTGGTGGTAGCGTTA |
| Acy1 | CAGCCAAGGCAATTTCAGAGC | CTCGACGTTTGATTAACTGGTCT |
| Nr1d2 | TGAACGCAGGAGGTGTGATTG | GAGGACTGGAAGCTATTCTCAGA |
| Ddx17 | TCTTCAGCCAACAATCCCAATC | GGCTCTATCGGTTTCACTACG |
| Aplp2 | GTGGTGGAAGACCGTGACTAC | TCGGGGAACTTTAACATCGT |
| Nr3d1 | AGCTCCCCCTGGTAGAGAC | GGTGAAGACGCAGAAACCTTG |
| Rybp | CGACCAGGCCAAAAAGACAAG | CACATCGCAGATGCTGCATT |
| Txnip | TCTTTTGAGGTGGTCTTCAACG | GCTTTGACTCGGGTAACTTCACA |
| Nr1d1 | TACATTGGCTCTAGTGGCTCC | CAGTAGGTGATGGTGGGAAGTA |

EXEMPLIFICATION

This invention is further illustrated by the following examples, which should not be construed as limiting.

Example 1: Materials and Methods for Examples 1-10 a. Cell Culture

3T3-L1 and HEK-293 cells were obtained from ATCC. PPAR gamma-null mouse embryonic fibroblasts (MEFs) (Reaven et al., *Diabetes* 37: 1020-1024 (1988)) were cultured in Dulbecco's modified Eagle's medium and 10% fetal bovine serum. FLAG-PPAR gamma and FLAG-PPAR gamma S273A were subcloned into pMSCV-puro retroviral vector (Stratagene). For retrovirus production, Phoenix packaging cells were transfected with 10 μg retroviral vectors (Kinsella et al., *Hum. Gene Ther.* 7: 1405-1413 (1996)). After 48 hours, the viral supernatant was collected and filtered. Following infection of the cells with the retrovirus, cells expressing the ectopic protein were selected by incubation with 2 μg/ml puromycin. Adipocyte differentiation 3T3-L1 or MEFs was induced by treating cells with 1 μM dexamethasone, 0.5 mM isobutylmethylxanthine, and 850 mM insulin for 48 h and cells were switched to the maintenance medium containing 850 nM insulin. Lipid accumulation in the cells was detected by Oil Red 0 staining. The amount of secreted adiponectin into cell medium was analyzed by ELISA (Millipore). All chemicals for cell culture were obtained from Sigma unless otherwise indicated.

b. DNA Constructs and shRNA of CDK5

HA-WT CDK5, HA-KD CDK5 and Myc-p35 were obtained from Addgene. Murine PPARα or PPARδ were subcloned into FLAG-pcDNA3.1 (Invitrogen). The sequence used for lentivial shRNA expression vector (pLKO.1; Open Biosystems) targeting CDK5 was 5'-TG-TAAGAGAATAAAGCGTGAA-3' (SEQ ID NO: 81). For lentivirus production, HEK-293T cells (ATCC) were transfected with 10 μg lentiviral vectors (Kinsella et al., *Hum. Gene Ther.* 7: 1405-1413 (1996)). Following infection of the cells with the lentivirus, cells were selected by incubation with 2 μg/ml puromycin.

c. In Vitro Kinase Assay

Kinase assays were performed using an active cdk5/p35 protein and recombinant PPAR gamma protein as a substrate in kinase buffer in the presence of ATP. The reaction was stopped by adding sample buffer. Samples were then subjected to SDS-PAGE, and detected by CDK substrate antibody. In particular, active cdk5/p35, cdk1/cdc2, cdk2/cyclin A, cdk2/cyclin E or cdk4/cyclin D1 kinases were purchased from Millipore or Cell Signaling Technology. In vitro CDK kinase assay was performed according to the manufacturer's instructions (Cell Signaling Technology). Briefly, 1 μg of immuno-purified WT or S273A mutant of PPAR gamma were incubated with active CDK kinase in kinase assay buffer (25 mM Tris-HCl pH 7.5, 5 mM beta-glycerophosphate, 2 mM dithiothreitol (DTT), 0.1 mM $Na_3VO_4$, 10 mM $MgCl_2$) containing 20 μM ATP for 15 min at 30° C. Positive control for assay, purified histone H1 (Millipore) or Rb (Cell Signaling Technology) were used. Several PPAR gamma ligands were pre-incubated with substrates for 30 min, and the assay was performed. Phosphorylation of substrates after SDS-PAGE was analyzed with anti-CDK substrate antibody (Cell Signaling Technology).

d. Preparation of Cell or Tissue Lysates, Immunoprecipitation and Immunoblotting HEK-293 cells expressing CDK5 or PPAR gamma were collected after transfection. Total cell lysates were incubated with FLAG M2 agarose (Sigma) at 4° C. Immunoprecipitates or total cell lysates were analyzed with anti-CDK substrate, FLAG or HA (Roche) antibodies. Differentiated 3T3-L1 adipocytes were treated with TNF-α (50 ng/ml), IL-6 (50 ng/ml), IL-10 (50 ng/ml) or FFAs (400 µM palmitic acid and oleic acid mixtures) for the indicated times, and cell lysates were analyzed with phospho-specific or PPAR gamma antibodies. 3T3-L1 adipocytes were pre-treated with various PPAR gamma ligands, and incubated with TNF-α. For tissue lysates, WAT from mice was homogenized in RIPA buffer (50 mM Tris pH7.5, 150 mM NaCl, 1% NP-40, 0.5% sodium deoxycholate, 0.1% SDS with protease and phosphatase inhibitors). For western blotting, a rabbit polyclonal phospho-specific antibody against PPAR gamma Ser273 was produced by New England Peptides with a synthetic phosphopeptide corresponding to residues surrounding Ser273 of PPART gamma (Ac-KTTDKpSPFVI-YDC-amide (SEQ ID NO: 82)). Total tissue lysates were analyzed with anti-PPAR gamma, phospho-CDK5 (Y15), CDK5 and p35 antibodies (Santa Cruz). Phosphorylation of PPAR gamma on Ser112 or Ser273 was detected by phospho-specific antibodies (Ser112, Millipore, MAB3632).

e. Reporter Gene Assay

In some examples, HEK-293 cells were seeded in 12-well plates at $1.5 \times 10^5$ cells/well. HEK-293 cells were transfected with pDR-1 (3x, based on the UCP1 PPAR gamma recognition site)-luciferase reporter plasmid, PPAR gamma, RXRa and pRL-renillin using Lipofectamine 2000 (Invitrogen). Following an overnight transfection, the cells were treated with rosiglitazone or MRL24 for 24 hours. The cells were harvested and reporter gene assays were carried out using the Dual-Luciferase kit (Promega). Luciferase activity was normalized to renillia activity.

f. Gene Expression Analysis

Total RNA was isolated from cells or tissues using Trizol reagents (Invitrogen). The RNA was reverse-transcribed using ABI reverse transcription kit. Quantitative PCR reactions were performed with SYBR green fluorescent dye using an ABI9300 PCR machine. Relative mRNA expression was determined by the ΔΔ-Ct method normalized to TATA-binding protein (TBP) levels. The sequences of primers used in this study are found in Table 3.

g. Generation of Fat Pads in Nude Mice

PPAR gamma-null fibroblasts ($1 \times 10^7$) stably expressing WT or S273A mutant of PPAR gamma were implanted subcutaneously into 7-8 week-old male NCR nude mice (Taconic) according to the previous methods (n=5 mice per group) (Walkey et al., *J. Biol. Chem.* 283: 24290-24294 (2008)). Six weeks after injection, the fat pads were isolated for the analysis of gene expression.

h. Microarray Analysis

Total RNA was isolated from PPAR gamma-null fibroblasts expressing WT or S273A mutant of PPAR gamma or WT cells treated with 1 µM rosiglitazone or MRL24 for 24 hours. Array hybridization and scanning were performed by the Dana-Farber Cancer Institute Microarray Core Facility using Affymetrix GeneChip Mouse Genome 430 2.0 arrays according to established methods (Lockhart et al., *Nat. Biotechnol.* 14: 1675-1680 (1996)). The array data were analyzed using the DNA-Chip Analyzer (dChip) software (Li et al., *Proc. Natl. Acad. Sci. USA* 98: 31-36 (2001)) The statistical significance of differences in gene expression was assessed by an unpaired t-test (p<0.05). To create refined gene sets regulated by cdk5 phosphorylation of PPAR gamma, p-value as well as fold-change of gene expression in WT versus S273A mutant cells was first calculated, and —log p-value versus $\log_2$ fold-change was plotted. From this list of genes, 53 genes were selected which were changed in magnitude (4 fold difference) and statistical significance (p<0.05). The selected genes were validated in cells or transplanted fat pads by qPCR, the resulting gene set, consisting of 17 genes, was analyzed in WAT of mice using qPCR.

i. Animals

All animal experiments were performed according to procedures approved by Beth Israel Deaconess Medical Center's Institutional Animal Care and Use Committee. 4 to 5-week old male C57BL/6J mice were obtained from the Jackson Laboratory. Mice were fed a regular diet (10% kcal fat, D12450B, Research Diets Inc.) or a high fat diet (60% kcal fat, D12492, Research Diets Inc.) as indicated time periods. For glucose tolerant tests, mice were intraperitoneally (i.p.) injected daily 10 mg/kg rosiglitazone or MRL24 for 6 days, and fasted overnight prior to i.p. injection of 2 g/kg D-glucose. Glucose was measured in tail vain blood at intervals after glucose injection using a Truetrack glucometer. Serum insulin concentrations were determined by ELISA (Crystal Chem).

Example 2: cdk5 Specifically Phosphorylates Serine 273 of Mouse PPAR Gamma

Pro-inflammatory cytokines are secreted from both fat cells and immune cells residing in adipose tissue, specifically when animals or humans become obese (Hotamisligil et al., *Science* 259: 87-91 (1993)). Since PPAR gamma is a dominant regulator of adipogenesis and gene expression in fat cells, the structure of the molecule was analyzed and it was determined that the primary amino acid sequence of PPAR gamma contained a consensus site for phosphorylation by the protein kinase cdk5 at serine 273 of PPARγ2 (FIG. 1A). This protein kinase, despite being a member of the cdk gene family, is not regulated by cyclins and is instead activated by p35/25 which are targets of numerous cytokines and pro-inflammatory signals (Dhavan et al., *Nat. Rev. Mol. Cell. Biol.* 2: 749-759 (2001)). This cdk5 site is conserved in all sequenced mammalian PPAR gammas, but is not found in other members of the PPAR gene family. The cdk5 site in murine PPAR gamma can be phosphorylated when incubated in vitro with cdk5 and its activating cofactor p35. In fact, PPAR gamma is phosphorylated as efficiently under these conditions as is histone H1, a known substrate of the cdk5/p35 complex (FIG. 1B). Mutation of serine 273 to alanine completely blocks phosphorylation of PPAR gamma, indicating that there were no other cryptic sites for this protein kinase on PPAR gamma (FIG. 1B). Other members of the cdk protein family did not phosphorylate PPAR gamma. Cdk5 also phosphorylated PPAR gamma in cells, as shown by co-transfection of this kinase with the wild-type (WT) and mutant PPAR gamma (FIG. 1C). This phosphorylation in cells was detected with an antibody against a peptide phosphorylated at a consensus cdk5 site. A version of cdk5 with a mutation inactivating the kinase activity (KD) did not modify PPAR gamma. Moreover, these results were independent of phosphorylation of serine 112. Finally, cdk5 did not modify murine PPAR alpha or PPAR delta in cells (FIG. 1D).

Example 3: Phosphorylation of PPAR Gamma at Ser 273 Regulates Adipogenesis

Figure 2:
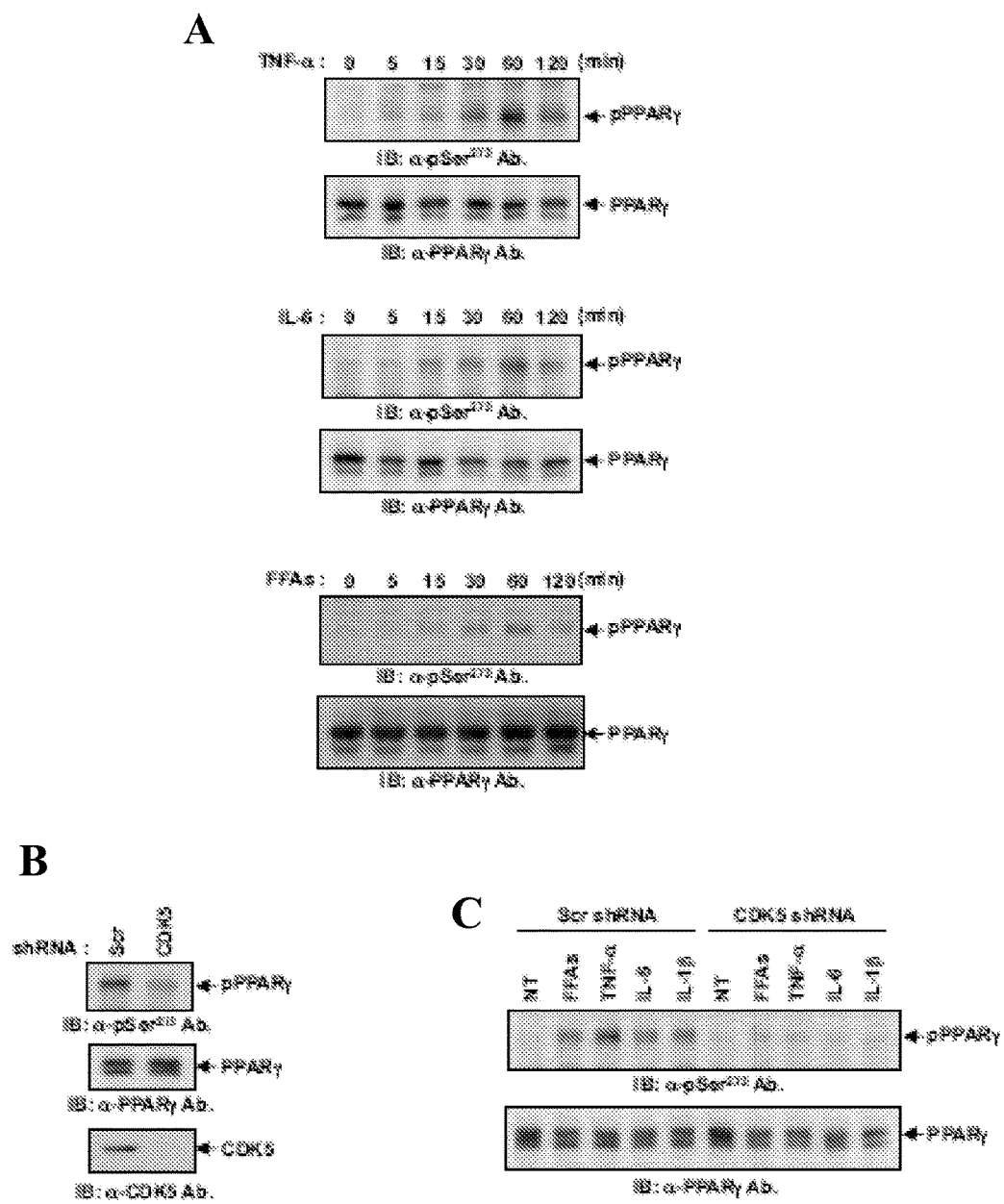
FIGS. 2A-2C depict results of cdk5-specific phosphorylation of PPAR gamma upon exposure of cells to pro-inflammatory cytokines or free fatty acids (FFA).

Obesity is characterized by elevated circulating levels of pro-inflammatory cytokines and free fatty acids. As noted above, cdk5 is known to be activated by cytokines (e.g., TNF-alpha) (Dhavan et al., *Nat. Rev. Mol. Cell. Biol.* 2: 749-759 (2001); Utreras. et al., *J. Biol. Chem.* 284: 2275-2284 (2009)). FIG. 2A shows that treatment of 3T3-L1 adipocytes with TNF-α or IL-6 causes phosphorylation of PPAR gamma at the cdk5 site, as shown by a specific antibody made against a phosphopeptide derived from the cdk5 site at serine 273. While there have been no reports of activation of cdk5 by free fatty acids (FFAs), these are known to be elevated in obesity (Reaven et al., *Diabetes* 37: 1020-1024 (1988)). FIG. 2A also shows that the phosphorylation of PPAR gamma at serine 273 occurs upon treatment of the fat cells with high levels of FFAs. The cytokine and FFA induced phosphorylations are indeed occurring through cdk5 and not a different kinase as shown in FIGS. 2B and 2C, where these modifications are ablated by treatment of cells with an shRNA which is directed against murine cdk5.

Figure 3:
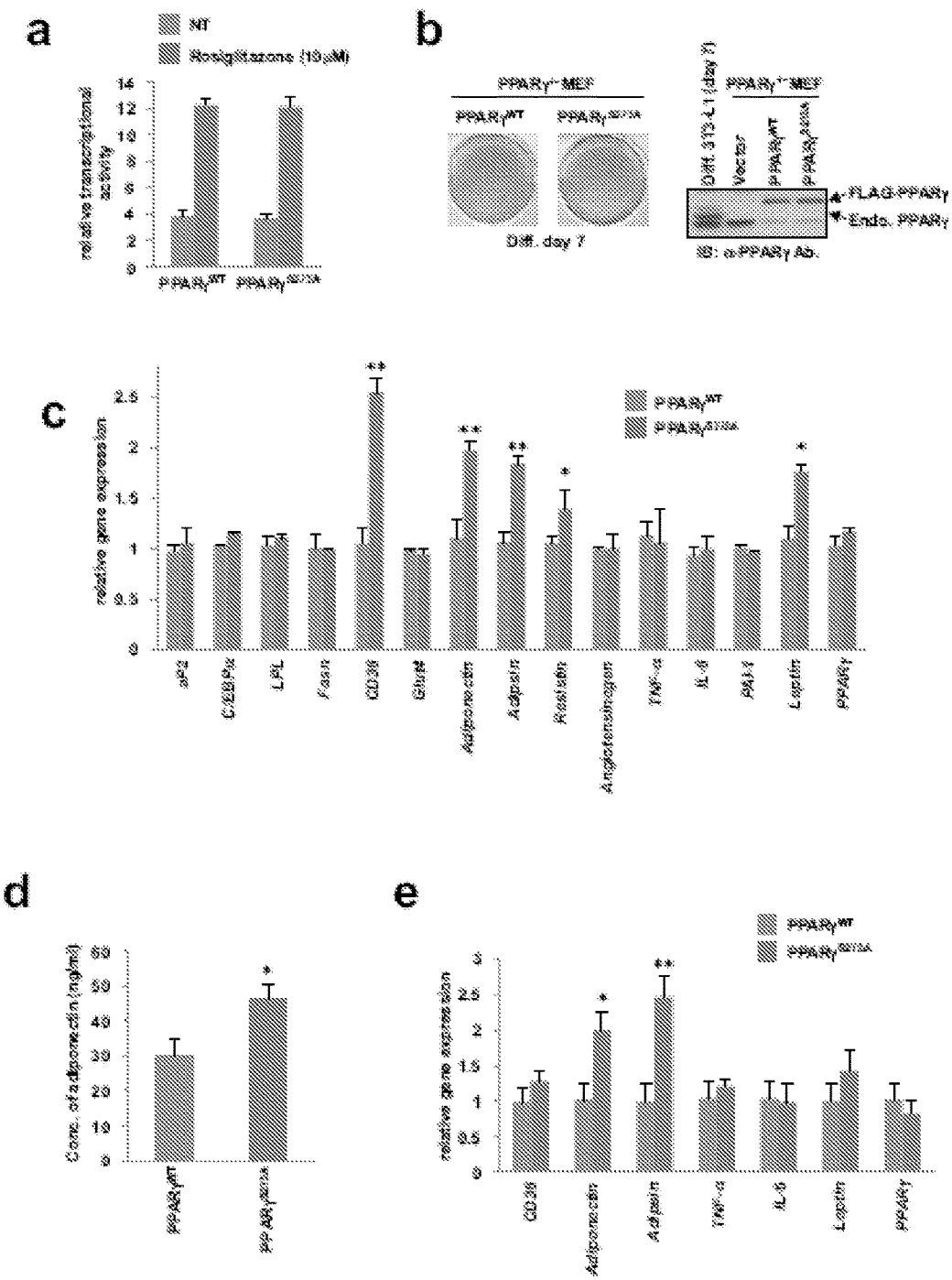
FIGS. 3A-3E depict results of specific fat cell gene dysregulation by the cdk-5 mediated S273 phosphorylation of PPAR gamma.

A study was performed to determine how the cdk5 modification of PPAR gamma altered the ability of this receptor to affect adipogenesis, and gene expression within differentiated fat cells. The wild type and S273A mutant alleles of PPAR gamma were expressed at equal RNA and protein levels in fibroblasts that completely lack PPAR gamma (FIGS. 3A and 3B; Rosen et al., *Genes & Dev.* 16: 22-26 (2002)). These initial experiments took advantage of the considerable basal level of cdk5-mediated phosphorylation in cultured cells (visible in the exposure shown in FIG. 2B), without addition of any other ligands. Serum has been shown to activate cdk5 in cultured cells (Musa et al., *J. Androl.* 21: 392-402 (2000)). Treatment of cells with cytokines and FFAs, which induce a more robust activation of cdk5, leads to a dedifferentiation of adipocytes, as has been shown earlier (Torti. et al., *Science* 229: 867-869 (1985)), and so could not be used in these experiments. The mutant and wild type PPAR gamma alleles both drove PPAR gamma transcriptional activity and adipogenesis with equal efficiency (FIGS. 3A and 3B). While most classical fat cell genes, like aP2 and C/EBPα were expressed to exactly equal levels, certain genes were sensitive to mutation in the PPAR gamma cdk5 site (FIG. 3C). These include the key fatty acid transporter, cd36, and the adipokines, adiponectin, adipsin and leptin. Mutation of the cdk5 site also caused an increase in the secretion of adiponectin into the culture medium (FIG. 3D).

Figure 8:
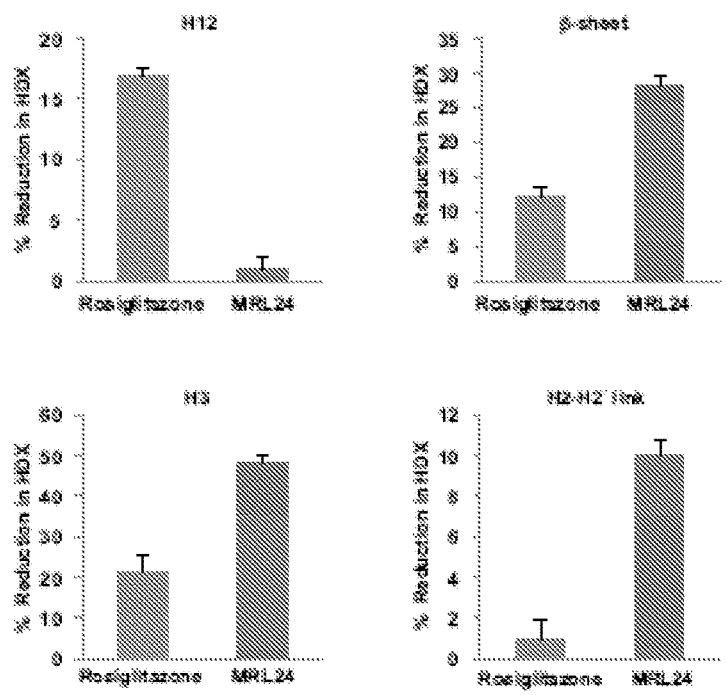
FIGS. 8A-8B depict differential HDX MS data for PPAR gamma-LBD±rosiglitazone and MRL24. The HDX data shown correspond to four regions of interest: Helix 3 (IRIFQGCQF (SEQ ID NO: 15)), the β-sheet region (ISEGQGFMTRE (SEQ ID NO: 16)), Helix 12 (QEIYKDLY (SEQ ID NO: 17)) and the Helix 2-2' link region containing the site of CDK5 phosphorylation (KTTDKSPFVIYDM (SEQ ID NO: 18)).
Figure 8:
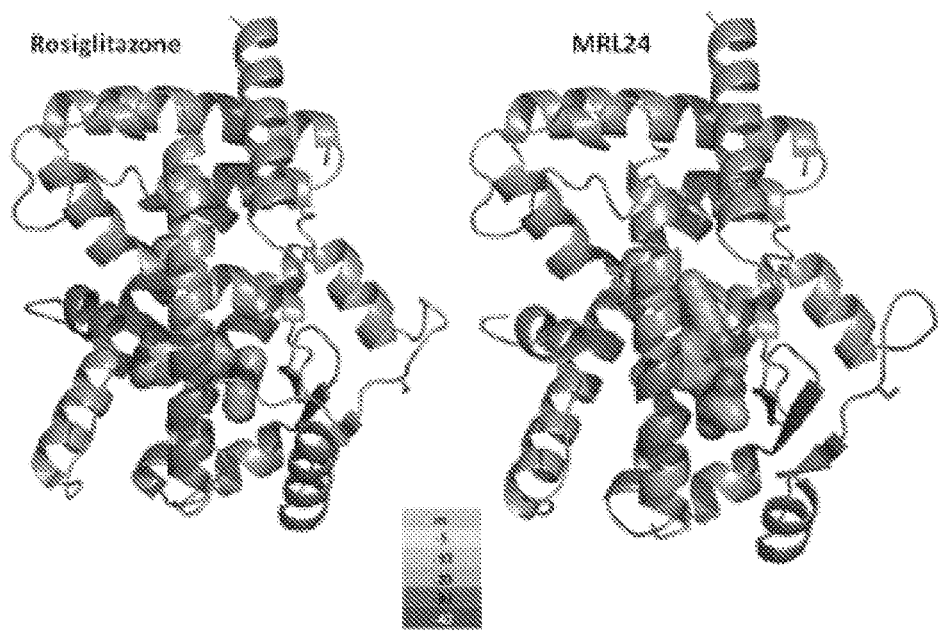

To examine the ability of this cdk5-mediated phosphorylation to alter fat cell gene expression in an in vivo context, wild type and mutant cells were transplanted under the skin of nude mice (FIG. 8A; Green et al., *J. Cell. Physiol.* 101: 169-171 (1979)). After 6 weeks, both cell types formed fat pads that could be isolated and analyzed for gene expression. Again, adiponectin and adipsin were both markedly dysregulated, being elevated in the cells expressing mutant vs. wt PPAR gamma (FIG. 10B). This implies that the cdk5-mediated phosphorylation of PPAR gamma reduced the expression of both of these adipokines. While both cd36 and leptin were expressed at slightly higher levels in the mutant vs. wt cells, this did not reach statistical significance in these transplant experiments.

Example 4: Phosphorylation of PPAR Gamma at Ser 273 Occurs in Obesity

Figure 4:
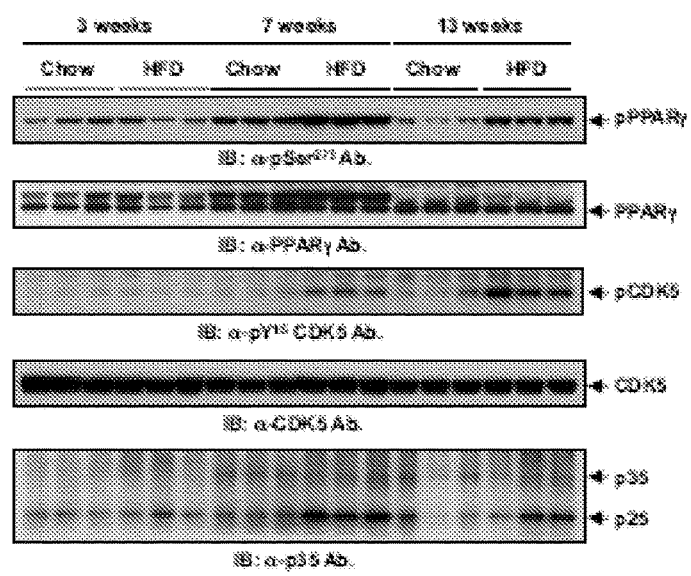
FIGS. 4A-4C depict results of CDK5-mediated phosphorylation of PPAR gamma increase in fat tissues of high fat diet fed mice (HFD).
Figure 4:
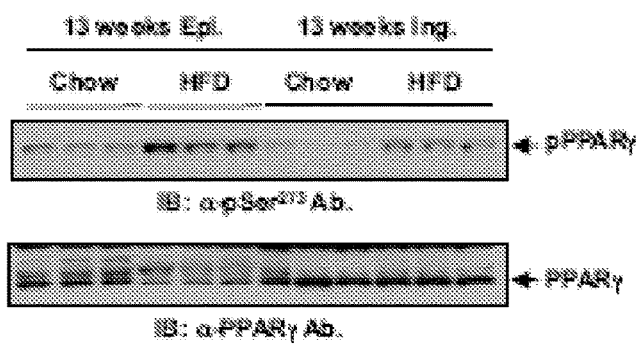

It is notable that several genes whose expression is dysregulated by the cdk5 mutation in PPAR gamma, such as adiponectin, adipsin and leptin, are known to be inappropriately regulated in many forms of animal and human obesity. In fact, the reduced levels of adiponectin in obesity has been shown to be at least partially responsible for the insulin-resistance that usually accompanies obesity (Hu et al., *J. Biol. Chem.* 271: 10697-10703 (1996)). This fact, along with the activation of cdk5 by cytokines and high fatty acid levels, directed experiments to test whether cdk5 is activated in the adipose tissues of obese mice and whether PPAR gamma is phosphorylated by cdk5 specifically in the context of obesity. Mice were placed on a standard chow or a high fat, high sugar diet containing 60% kcal from fat, and adipose tissues were harvested at several points after initiation of this protocol. Mice developed a trend toward elevated insulin, indicative of insulin resistance, at 7 weeks. Overt hyperinsulinemia, was apparent at 13 weeks after initiation of this diet (FIG. 4B). As shown in FIG. 4A, there was no activation of cdk5 (detectable by a specific phosphorylation at tyrosine 15 of murine cdk5) after 3 weeks of this high fate diet. However, activated cdk5 was easily observed after 7 weeks of the high fat diet. This time point also showed increased appearance of the cleaved p25 protein, the more stable form of this activating subunit for cdk4 (FIG. 4A; Dhavan et al., *Nat. Rev. Mol. Cell. Biol.* 2: 749-759 (2001)). There was a detectable basal level of phosphorylation on serine 273 in chow fed animals, and there was no increase in this modification after 3 weeks on the high fat diet. However, by 7 weeks on this diet, epidydimal fat tissues showed a clear increase in this phosphorylation of PPAR gamma compared to chow fed controls. This difference in phosphorylation between chow and high fat-fed animals was obvious after 13 weeks on this diet. Cdk5-mediated modification was also observed in two different white fat depots: inguinal fat, which is a type of subcutaneous fat, and epididymal fat, which is considered a visceral depot (Cinti, S., *Prostaglandins Leukot Essent Fatty Acids* 73: 9-15 (2005)). FIG. 4C illustrates that this increase in phosphorylation by cdk5 occurs in both white fat depots, with greater intensity of phosphorylation at S273 in the epididymal fat.

Example 5: PPAR Gamma Ligands can Inhibit Phosphorylation of PPAR Gamma at Ser 273

Anti-diabetic drugs of the thiazolidinedione (TZD) class, such as rosiglitazone, are known to bind to and activate PPAR gamma, improving insulin sensitivity of mice and humans (Willson et al., *Annu. Rev. Biochem.* 70: 341-367 (2001)). To ask whether TZDs and other anti-diabetic PPAR gamma ligands alter the cdk5-mediated phosphorylation of this receptor, fat cells expressing wild type PPAR gamma were treated with TNF alpha, rosiglitazone, or a combination of the two agents. FIG. 5A shows that rosiglitazone inhibited this modification at approximately 1 μM, similar to the dose required for other PPAR gamma mediated activities in adipose cells (Lehmann et al., *J. Biol. Chem.* 270: 12953-12956 (1995)). GW 9662, a PPAR gamma antagonist (Leesnitzer. et al., *Biochemistry* 41: 6640-6650 (2002)), completely blocked this effect of rosiglitazone. The effect of these compounds on the cdk5-mediated phosphorylation of a mutant form of PPAR gamma (Q286P; Sarraf et al. *Mol. Cell.* 3:799-804 (1999)), a naturally occurring mutant of the receptor that can no longer directly bind any known ligands was also examined. Rosiglitazone could not interfere with the cdk5 phosphorylation in this case, implying that direct binding of the ligand was required for this inhibition.

The most obvious interpretation of this data would be that the PPAR gamma agonist turned off the expression of the protein kinase or turned on the expression of a relevant protein phosphatase working on the receptor. However, a study was performed to determine whether rosiglitazone and other PPAR gamma ligands work directly to inhibit cdk5 phosphorylation in vitro. To address this, purified PPAR gamma and cdk5/p35 were mixed with or without rosiglitazone under appropriate conditions to achieve modification in vitro. Surprisingly, FIG. 5B shows that rosiglitazone blocked this cdk5-mediated phosphorylation in vitro, with a half-maximally effective dose of about 30 nM, near the $K_d$ of this compound for PPAR gamma binding (Lehmann et al. *J. Biol. Chem.* 270:12953-12956 (1995)). Importantly, this inhibition is not caused by a general inhibition of cdk5 activity, since incubation with rosiglitazone does not inhibit the ability of cdk5 to phosphorylate the Rb protein (FIG. 5D).

Figure 5:
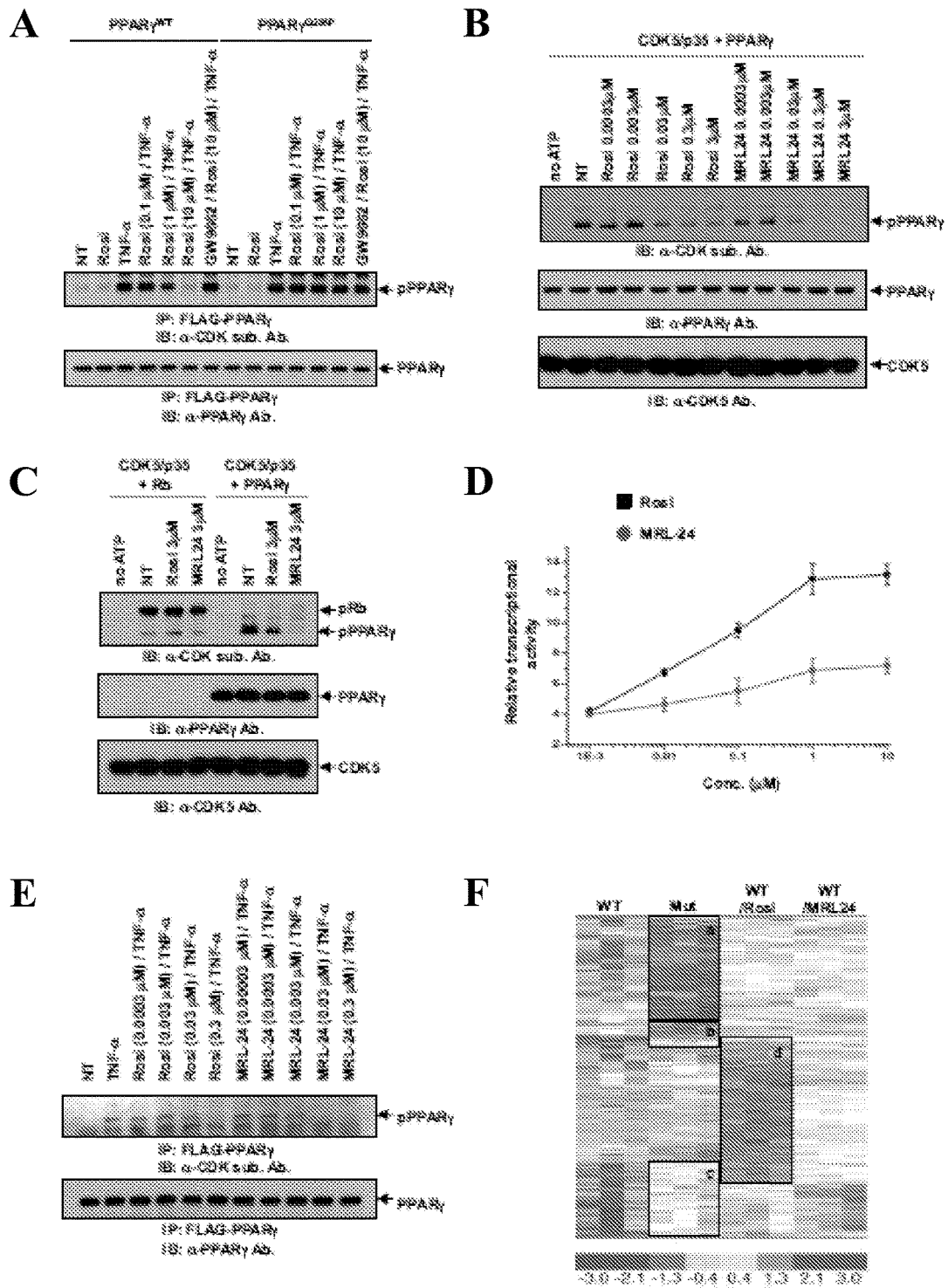
FIGS. 5A-5F depict results of PPAR gamma ligands inhibiting phosphorylation of PPAR gamma.
Figure 6:
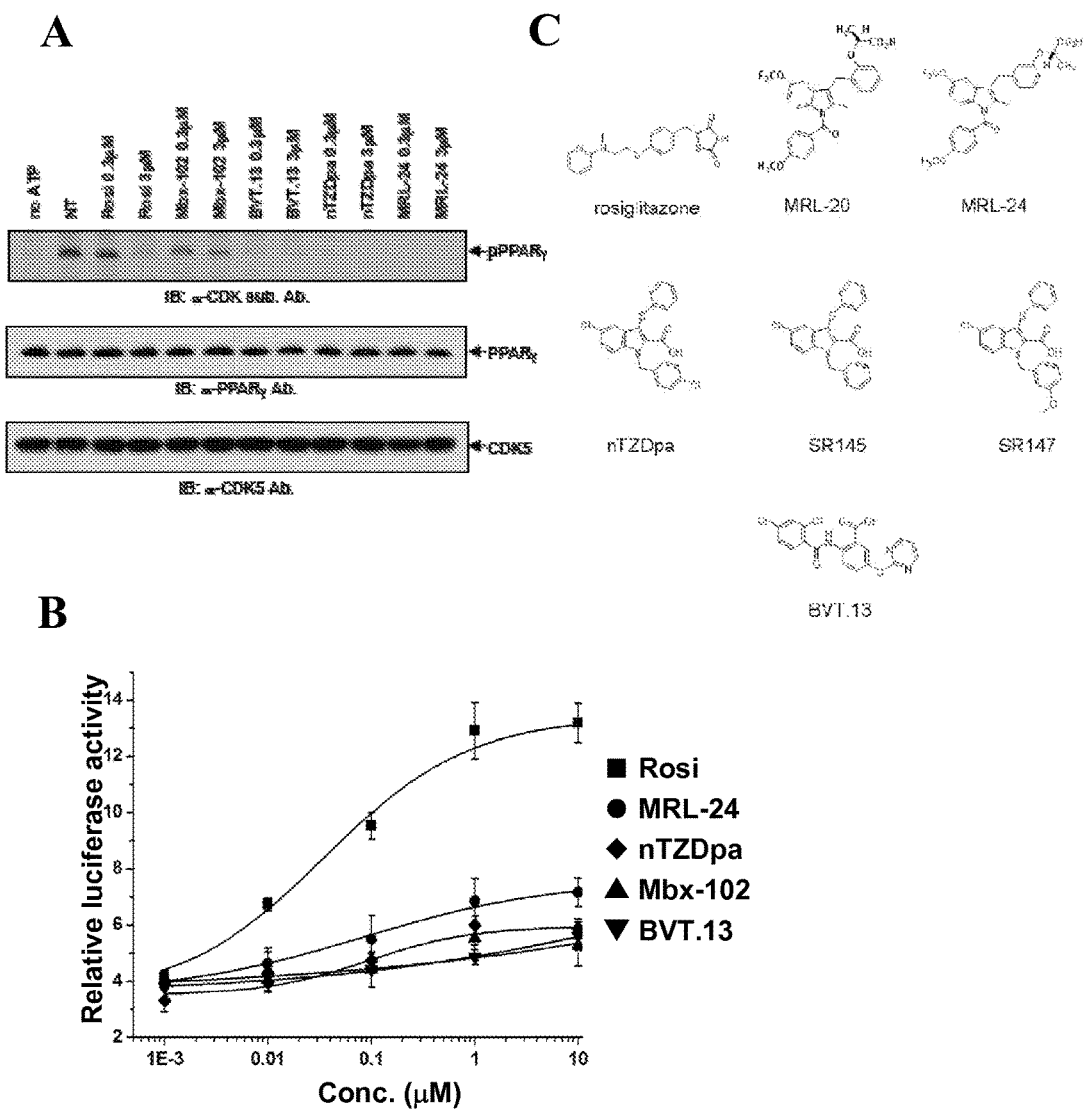
FIGS. 6A-6C depict results of atypical PPAR gamma ligands inhibiting CDK5-mediated phosphorylation of PPAR gamma.

Example 6: Atypical PPAR Gamma Agonists Selectively Inhibit Phosphorylation of PPAR Gamma at Ser 273 Over Classical Activation of PPAR Gamma Activity The fact that the PPAR gamma ligand rosiglitazone has the ability to block cdk5-mediated phosphorylation of PPAR gamma independent of both DNA binding and direct transcriptional agonism indicated an intriguing explanation for how some of PPAR gamma ligands with poor agonist properties can have substantial anti-diabetic activity. MRL24 is a non-TZD compound that has been reported to bind avidly to PPAR gamma and have excellent anti-diabetic activity in mice (Acton et al., *Bioorg. Med. Chem. Lett.* 15: 357-362 (2005)). However, this compound is a poor agonist toward PPAR gamma in transcription assays, and consequently has virtually no ability to promote adipogenesis, a classical effect of a PPAR gamma agonist. As reported previously (Acton et al., *Bioorg. Med. Chem. Lett.* 15: 357-362 (2005) and as shown in FIG. 5D, MRL24 has very weak agonist activity on a PPAR transcriptional response element, compared to rosiglitazone. On the other hand, MRL24 was very effective at blocking the cdk5-mediated phosphorylation of PPAR gamma (FIG. 5B). For example, 30 nM of MRL24 inhibited the modification of PPAR gamma as well as 300 nM of rosiglitazone, both in vitro and in cells (FIGS. 5B and 5E). Again, this effect was not a result of a general inhibition of cdk5 itself because this kinase retained full ability to phosphorylate Rb in the presence of MRL24 in vitro. MRL24 had only a small fraction of the agonist activity of rosiglitazone at every dose studied (FIG. 5D). In fact, 30 nM MRL24, which blocked the TNF-α-mediated phosphorylation of PPAR gamma essentially completely (FIG. 5E), had essentially undetectable agonist activity on PPAR gamma in the same cells (FIG. 5D). In addition, the ability of a number of additional anti-diabetic PPAR gamma ligands with poor agonist properties to inhibit cdk5-mediated phosphorylation was assessed (Gregoire et al., *Mol. Endocrinol.* 23: 975-988 (2009); Berger et al., *Mol. Endocrinol.* 17: 662-676 (2003); Ostberg et al., *J. Biol. Chem.* 279: 41124-41130 (2004)). As shown in FIG. 6, all were effective at inhibiting the cdk5-mediated phosphorylation of PPAR gamma.

Example 7: Atypical PPAR Gamma Agonists Selectively Improves Insulin Sensitivity Over Classical Activation of PPAR Gamma Activity To take a systematic view of changes in gene expression caused in the same cells by both the cdk5 mutation in PPAR gamma and these PPAR gamma ligands, Affimetrix analyses of gene expression with RNA from cells expressing the wild type and mutant PPAR gammas, plus wild type cells treated with rosiglitazone or MRL24 were tested. As shown in FIG. 5F, unsupervised clustering of all these data resulted in several notable clusters of gene expression. When the data derived from cells containing the cdk5 mutation in PPAR gamma (Mut) were compared to that from the wild type controls, the genes with differential expression segregate into four major groups. One group, labeled "a", were genes whose expression was decreased by this mutation, thus implying that these genes are activated by cdk5 phosphorylation of PPAR gamma. This same group of genes was also suppressed by both rosiglitazone and MRL24, though neither ligand functioned as dramatically in this suppression as did the non-phosphorylatable mutant of PPAR gamma. This is understandable in that it is unlikely that treatment with these ligands could drive the dephosphorylation of PPAR gamma comparable to the mutant protein. The very small cluster labeled "b" contained Ahnak nucleoprotein and proteolipid protein (plp) 1, which are both critical for myelination (Hakak et al., *Proc. Natl. Acad. Sci. USA* 98: 4746-4751 (2001); Salim et al., *Glia* 57: 535-549 (2009)), and sorting nexin 5 (Snx5), which is important for vesicle trafficking (Merino-Trigo et al., *J. Cell. Sci.* 117: 6413-6424 (2004)). A larger cluster, labeled "c", represented genes that were increased in the mutant cells, representing those that were decreased by the cdk5-mediated phosphorylation of PPAR gamma. Several of the genes known to be dysregulated in obesity, including adiponectin and adipsin, were present in this cluster. Rosiglitazone also increased essentially all of these genes, but FIG. 5F indicates that this occurred as part of a very large gene set increased by rosiglitzone action. Indeed, the genes induced most dramatically by rosiglitazone (labeled "d") did not correspond to the cdk5 mutation-induced gene set and were largely the classic genes of adipogenesis, like aP2 and lipoprotein lipase (Lpl). In sharp contrast, the gene cluster strongly increased by MRL 24 was much smaller than that induced by rosiglitazone, and corresponded remarkably well to the gene set induced by the mutation in the cdk5 site of PPAR gamma. These data indicate that both rosiglitazone and MRL24 control most of the same genes that are affected by the cdk5 phosphorylation of PPAR gamma, but that there is a much closer correspondence between the genes induced by MRL24 and those induced by the genetic inhibition of the cdk5-mediated PPAR gamma phosphorylation. Taken together, the data presented in FIGS. 3-5 indicate that the cdk5 modification of PPAR gamma is a major source of gene dysregulation and pathology of adipose tissues in obesity.

Figure 7:
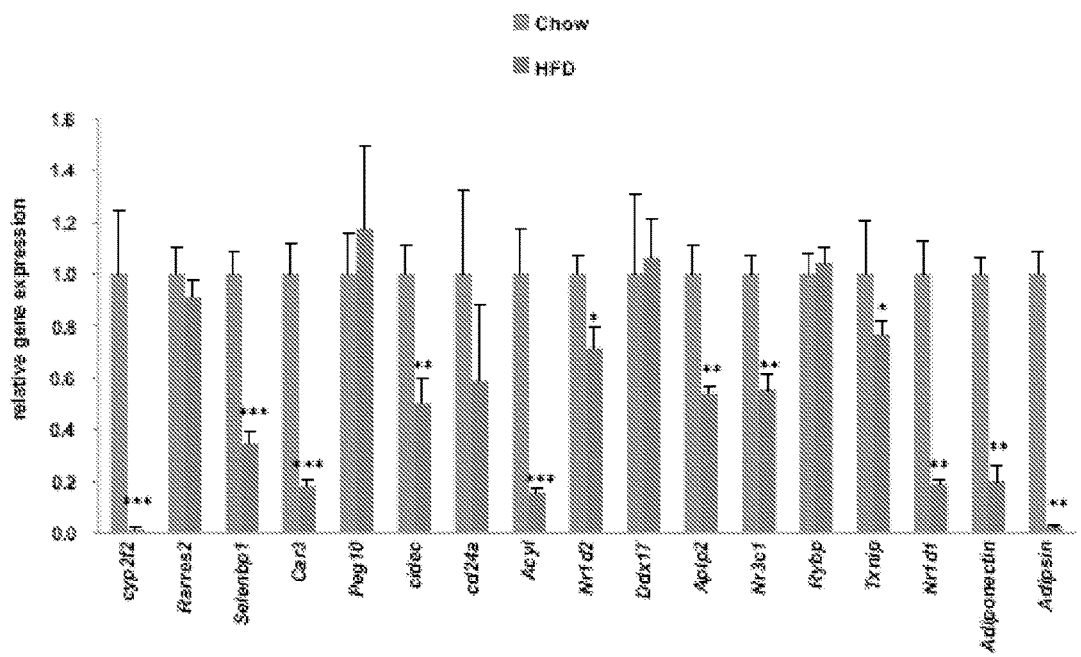
FIG. 7 depicts dysregulation of gene sets regulated by PPAR gamma phosphorylation in obese mice. mRNA expression of genes regulated by the phosphorylation of PPAr gamma in cells and transplanted fat pads in WAT of mice on either chow or HFD for 13 weeks (n=5; Error bars are s.e.m.; * p<0.05;  p<0.01;* p<0.001).

To further analyze the link, a refined gene set regulated by the cdk5 modification of PPAR gamma was created, using the concept of principal component analysis of gene expression data. For this, data was utilized from cell culture and from the transplantation of these cells in vivo. The expression of these genes was then examined in the adipose tissue of mice on a chow or high fat diet for 13 weeks. FIG. 7 shows that the great majority of these genes had dysregulated expression in an obesity-dependent manner. In total, of the 17 genes found to be most significantly reduced by cdk5 phosphorylation of PPAR gamma, at least 12 of these genes were quantitatively altered in obesity in the direction predicted. Genes well-known to be quantitatively dysregulated in obesity like adiponectin and adipsin were in this group. Also in this group were several genes not known to be associated with obesity, such as retinoic acid receptor responder 2 (Rarres2), selenium binding protein 1 (Slelnbp1), and carbonic anhydrase 3 (Car3).

To develop a structural understanding of how PPAR gamma ligands affect the cdk5-mediated phosphorylation of PPAR gamma, hydrogen/deuterium exchange (HDX) techniques linked to mass spectrometry were used 9 Maier et al., *Methods Enzymol.* 402: 312-360 (2005)).

As shown in FIG. 8a, rosiglitazone dramatically reduced H/D exchange in helix 12 (H12), the helix in the ligand-binding domain comprising part of the AF-2 surface of the receptor that is responsible for classical agonism (Nolte et al., *Nature* 395: 137-143 (1998); Bruning et al., *Structure* 15: 1258-1271 (2007)). By contrast, MRL24 had no statistically significant effect on the dynamics of this helix (Bruning et al., *Structure* 15: 1258-1271 (2007)). On the other hand, MRL24 had a more marked impact on H/D exchange kinetics across H3 (amino acids 309-315), the β-sheet at amino acids 369-379, and the cdk5 site itself at serine 273 in PPAR gamma. Rosiglitazone also affected the exchange across H3, and the beta sheet region, but did not alter the H/D exchange across serine 273 to any significant extent. When these HDX data are mapped onto the known co-crystal structures of PPAR gamma with each of these ligands bound, it is clear that both PPAR gamma ligands reduced the dynamic nature of this receptor in regions near the cdk5 site. However, MRL24 reduced the dynamic nature of these regions to a greater extent than rosiglitazone (FIG. 8b). It is thus believed that this reduced dynamic nature in the H3, β-sheet, and cdk5 site itself, induced by the PPAR gamma ligands (especially MRL24), "freezes" this region in a configuration less favorable to, or even incompatible with, the cdk5 phosphorylation.

Figure 9:
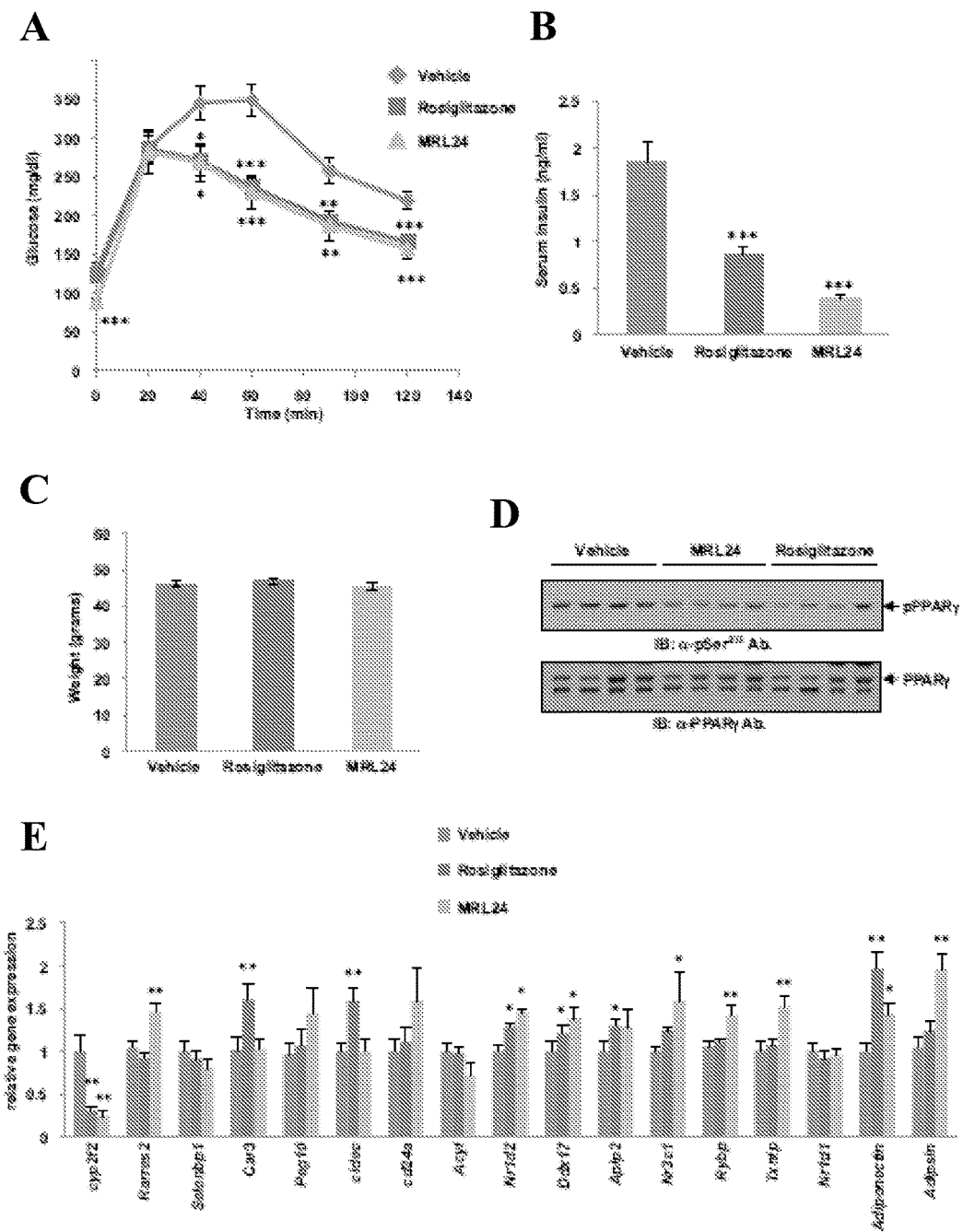
FIGS. 9A-9E depict results of anti-diabetic, atypical PPAR gamma agonists selectively inhibiting phosphorylation of PPAR gamma and reversing changes in gene expression in vivo.

In addition, it was further investigated whether the PPAR gamma ligands can alter the cdk5-mediated phosphorylation that occurs in vivo, and whether these agents regulate the genes controlled by cdk5 action on PPAR gamma. As shown in FIGS. 9A through 9C, treatment with either rosiglitazone or MRL24 at 10 mg/kg for 7 days dramatically improved glucose tolerance of high-fat fed mice and reduced fasting insulin levels without inducing changes in body weight. Importantly, these anti-diabetic doses of both of these compounds reduced the cdk5-mediated phosphorylation of PPAR gamma in the adipose tissue of every mouse treated with these agents (FIG. 9D). Furthermore 12 of the 17 genes most significantly controlled by cdk5 action on PPAR gamma (as described above) were altered by the action of one or both agents (FIG. 9E). These data indicate that these anti-diabetic PPAR gamma ligands inhibited cdk5 phosphorylation of PPAR gamma in vivo and reversed changes in gene expression due to that modification.

Figure 10:
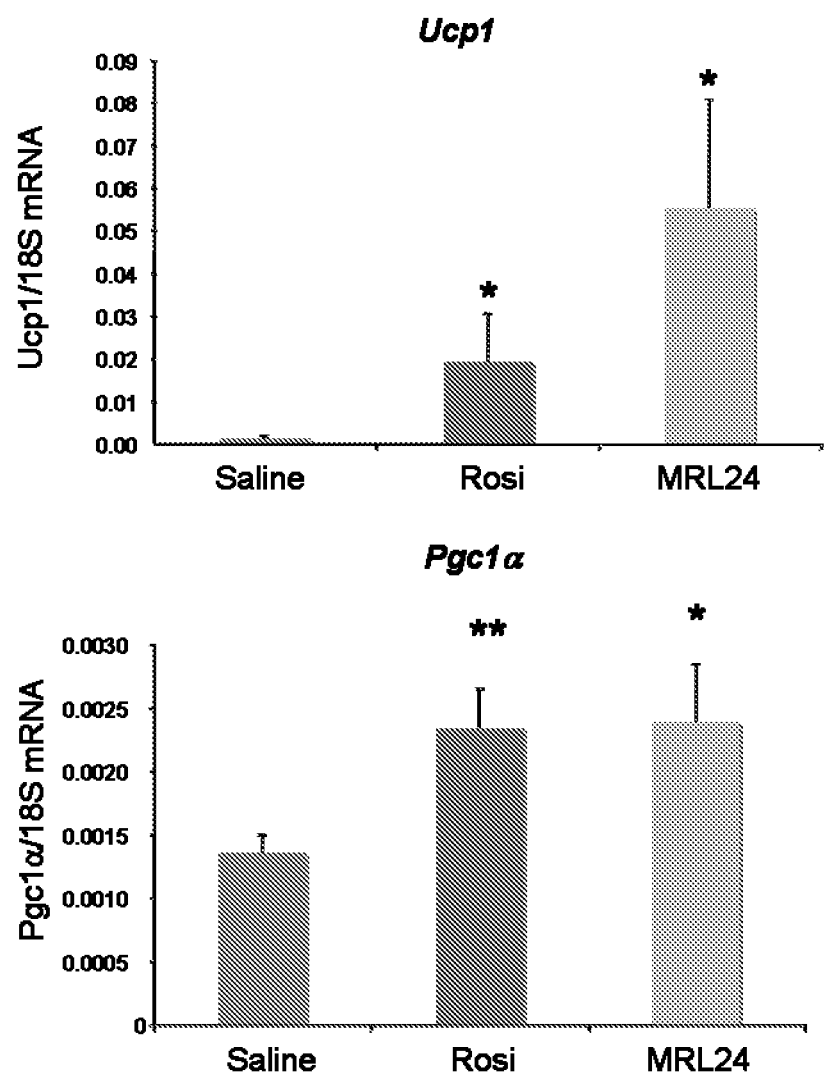
FIG. 10 depicts results of increasing brown fat selective gene expression in white adipose tissues upon administration of no agonists, classical PPAR gamma agonists, or atypical PPAR gamma agonists in animals.

Example 8: Atypical PPAR Gamma Agonists Selectively Brown White Fat and Increases Whole Body Energy Expenditure FIG. 10 shows that atypical PPAR gamma agonist selectively induces expression of brown fat selective genes, UCP1 and PGC-1alpha in white fat isolated from mice, with similar potency as typical agonist, rosiglitazone. Inguinal fat depots were isolated from mice treated with saline (control), rosiglitazone at 10 mg/kg or MRL24 at 3 mg/kg for 10 days. Total RNA was isolated from these samples. Subsequently, expression of UCP1 and PGC-1alpha was quantified by real-time PCR. mRNA level of UCP1 and PGC-1alpha was normalized with that of 18S.

Figure 11:
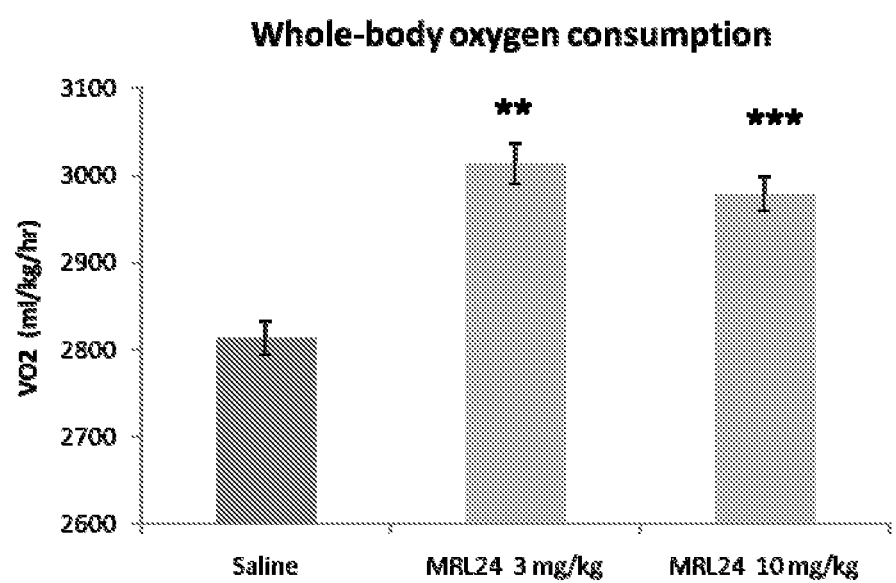
FIG. 11 depicts results of respiration experiments performed on animals treated with or without atypical PPAR gamma agonists.

FIG. 11 shows that atypical PPAR gamma agonists also selectively increase whole body oxygen consumption in vivo. Oxygen consumption was measured in mice treated with saline (control), rosiglitazone or MRL24 at 10 mg/kg for 10 days using Comprehensive Lab Animal Monitoring System (CLAMS).

Example 9: Generating and Characterizing a Knock-in Mouse Line Encoding PPAR Gamma Non-Phosphorylatable at Serine 273

Figure 12:
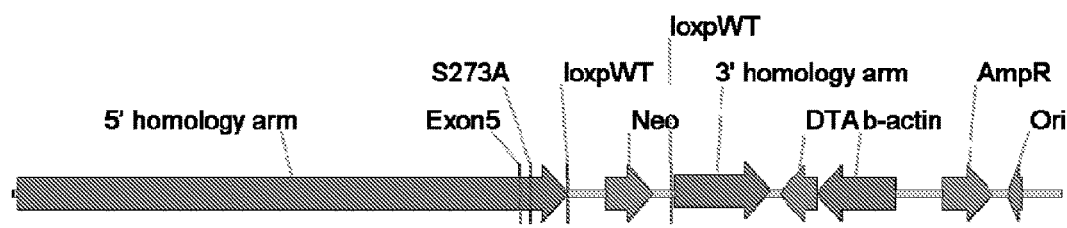
FIGS. 12A-12B depict a targeted knock-in animal construct generation (FIG. 11A) and breeding (FIG. 11B) strategy.
Figure 12:
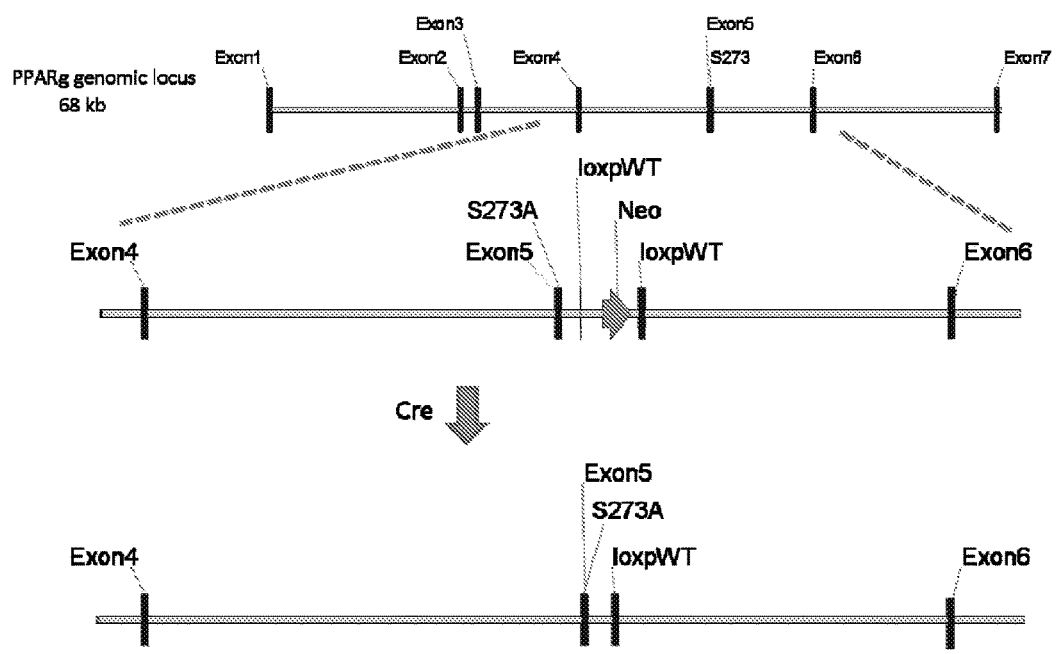

PPAR gamma serine 273 resides within the $5^{th}$ exon of PPAR gamma (reference sequence obtained from Ensembl PPAR gamma ENSMUSG00000000440). A BAC (Bacterial artificial chromosome) clone RP23-232H15 containing the PPAR gamma genomic locus was purchased from Invitrogen. An 11 kb DNA fragment centered around the $5^{th}$ exon of PPAR gamma was retrieved from the BAC into a cloning plasmid containing a diphtheria toxin negative selection marker. A fragment containing the S273A mutation and a novel site for restriction endonuclease cleavage was introduced into this parent plasmid. Lastly, the DNA sequence encoding the loxP-Neo-loxP positive selection cassette was introduced into the targeting plasmid (FIG. 12A). This plasmid was linearized and electroporated into ES cells. ES cells were cultured, screened for correct targeting, and implanted into mice. Progeny will be bred to Zp3-Cre expressing mice to delete the Neomycin cassette from within the PPAR gamma gene. These mice will then be bred to homozygosity in the absence of the Cre gene (FIG. 12B).

Homozygous S273A mutant PPAR gamma knock-in mice may be used, at least in part, to test the efficacy of potential therapeutics. MRL-24 and similar compounds which block the phosphorylation of PPAR gamma at serine 273 by cdk5 (phopho-blockers) are believed to improve the metabolic syndrome without having the side-effects of classical agonists, such as TZDs.

For example, PPAR gamma is active in both lean and obese individuals; however in these states, PPAR gamma exhibits slightly different transcription of target genes. Without being bound by theory, it is believed that this difference in transcriptional activity is due to the inhibitory phosphorylation of PPAR gamma at Ser-273. Mice with both copies of PPAR gamma mutated at Ser-273 to alanine or other non-phosphorylatable amino acid residues are believed to retain normal glucose tolerance when faced with the challenge of a high-fat diet.

The glucose lowering effect of MRL-24 does not require PPAR gamma agonism, an effect that is likely responsible for weight gain and fluid retention observed upon administration of classical PPAR gamma agonists. Without being bound by theory, it is believed that such classical PPAR gamma agonists (e.g., rosiglitizone) will have the positive glucose lowering only in WT mice but not in S273A mice. However the side effects, such as weight gain and fluid retention will still occur in both strains. Hence, an ideal compound would have no effect in the knock-in mice making it a good model for testing off-target effects of the drug.

Cells lines taken from these knock in mice can be used for in vitro testing of potential compounds. Specific chemical entities are believed to only alter target genes in wild-type cells, not in knock-in cells.

S273A PPAR gamma mutant knock-in animals can also be used in bone marrow transplantation assays. Bone marrow transplantation from a wild type animal to S273A PPAR gamma mutant knock-in animals and vice versa can be used to analyze activity of such mutant PPAR gamma polypeptides in immune system cells (e.g., macrophages and monocytes) in a wild type host background and vice versa, for example, to determine whether risk of atherosclerosis due to CD36-dependent decreased lipid uptake is mediated by immune system cells.

Figure 13:
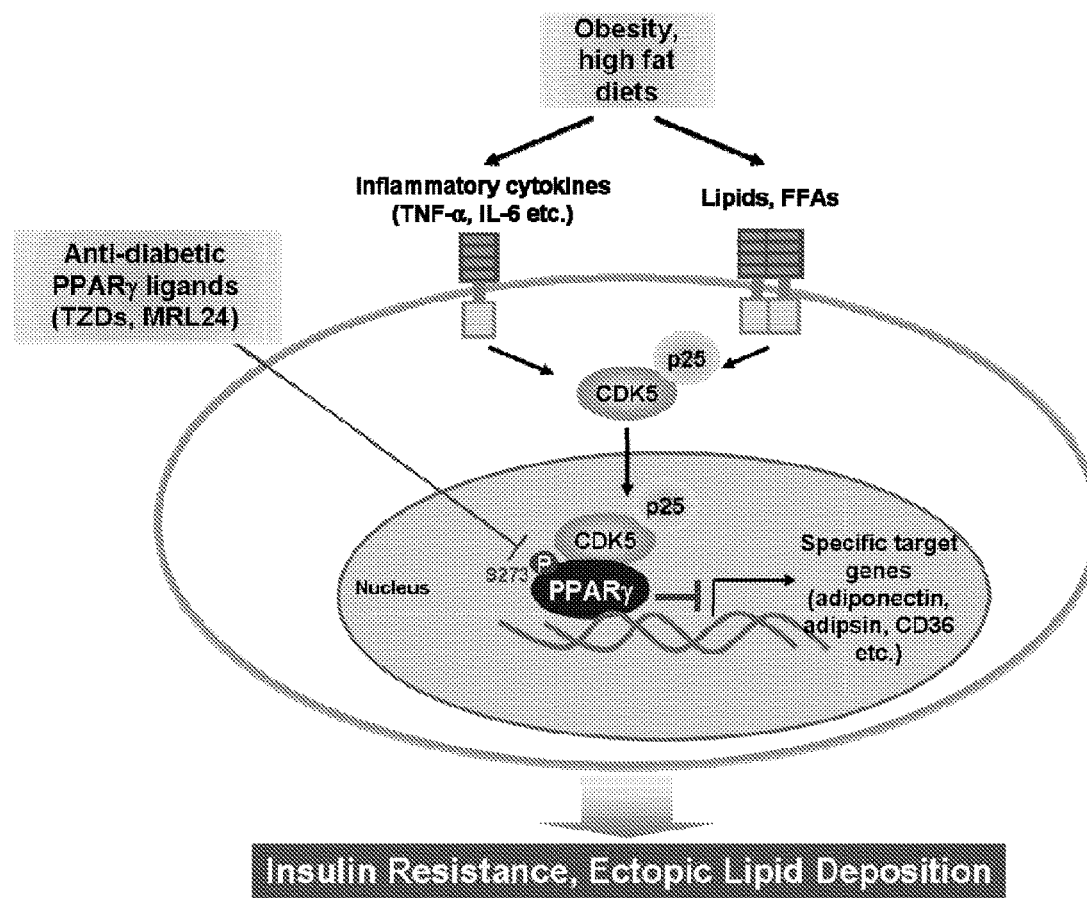
FIG. 13 depicts a model of obesity-linked phosphorylation of PPAR gamma by CDK5.

Based on all of the data provided herein, FIG. 13 provides a model of how, without being bound by theory, phosphorylation of PPAR gamma at Ser-273 is believed to selectively mediate anti-metabolic activities.

Figure 14:
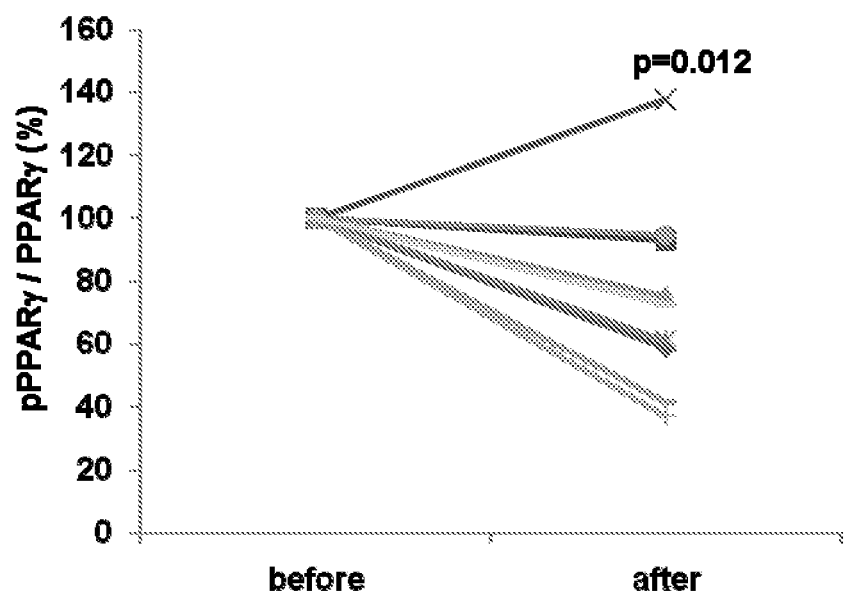
FIGS. 14A-14C depict results of PPAR gamma phosphorylation levels of human subjects having type 2 diabetes treated with rosiglitazone at a dose of 4 mg/day for six months.
Figure 14:
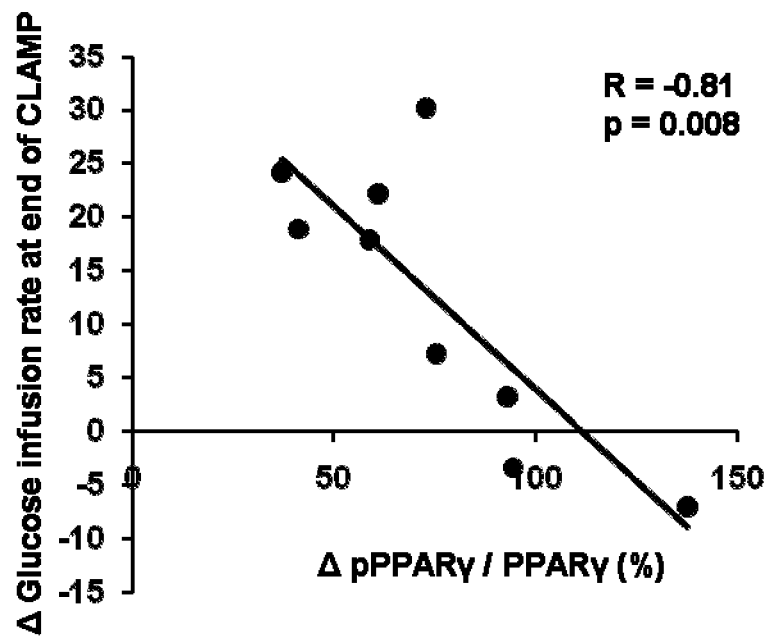

Example 10: Ser-273 Phosphorylation Status of PPAR Gamma is Predictive of Increased Glucose Sensitivity Nine human subjects having type 2 diabetes were treated with rosiglitazone at a dose of 4 mg/day for six months. CLAMP analyses were performed before and after the rosiglitazone treatment regimen. FIG. 14 provides data indicating the high correlation between decreased levels of phosphorylated Ser-273 produced through the rosiglitazone administration regimen and improved insulin sensitivity. Those subjects who did not exhibit significant decreases in phosphorylated Ser-273 levels were metabolically non-responsive to rosiglitazone (i.e., did not exhibit improved insulin sensitivity.

INCORPORATION BY REFERENCE

The contents of all references, patent applications, patents, and published patent applications, as well as the Figures and the Sequence Listing, cited throughout this application are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of identifying a compound which inhibits Ser-273 phosphorylation of murine PPAR gamma 2 or a corresponding serine residue in an ortholog of murine PPAR gamma 2 comprising:
   a) contacting a sample comprising a murine PPAR gamma 2 polypeptide or an ortholog of murine PPAR gamma 2, wherein the murine PPAR gamma 2 polypeptide or an ortholog of murine PPAR gamma 2 comprises the sequence KTTDKSPFVIYDM (SEQ ID NO: 94) with a test compound; and determining the amount of Ser-273-phophorylated murine PPAR gamma 2 relative to total PPAR gamma 2, or the amount of the corresponding serine-phosphorylated ortholog of the murine PPAR gamma 2 relative to total PPAR gamma 2;
   b) determining the amount of Ser-273-phophorylated murine PPAR gamma 2 relative to total PPAR gamma 2, or the amount of the corresponding serine-phosphorylated ortholog of the murine PPAR gamma 2 relative to total PPAR gamma 2 of a control;
   c) comparing the Ser-273 phosphorylation in (a) and (b); and identifying a compound that inhibits or reduces said Ser-273 phosphorylation in (a) relative to (b).

2. The method of claim 1, wherein the sample is selected from the group consisting of in vitro, ex vivo, and in vivo samples.

3. The method of claim 1, wherein the control is the amount of Ser-273-phophorylated murine PPAR gamma 2 relative to total PPAR gamma 2, or the amount of the corresponding serine-phosphorylated ortholog of the murine PPAR gamma 2 relative to total PPAR gamma 2 of the sample in the absence of the test compound.

4. The method of claim 1, wherein the control is the amount of Ser-273-phophorylated murine PPAR gamma 2 relative to total PPAR gamma 2, or the amount of the corresponding serine-phosphorylated ortholog of the murine PPAR gamma 2 relative to total PPAR gamma 2, of the sample contacted with a classical PPAR gamma 2 agonist.

5. The method of claim 1, wherein the control is the amount of Ser-273-phophorylated murine PPAR gamma 2 relative to total PPAR gamma 2, or the amount of the corresponding serine-phosphorylated ortholog of the murine PPAR gamma 2 relative to total PPAR gamma 2, of the sample contacted with rosiglitazone under standard conditions.

6. The method of claim 1, further comprising a step of determining whether the test compound directly binds the murine PPAR gamma 2 or the ortholog thereof.

7. The method of claim 1, wherein the sample is from preadipocytes, mature white adipocytes, brown adipocytes, monocytes, or macrophages.

8. The method of claim 1, wherein the sample is from an animal model of a metabolic disorder.

9. The method of claim 1, wherein said PPAR gamma 2 is human PPAR gamma 2.

10. The method of claim 9, wherein the sample is selected from the group consisting of in vitro, ex vivo, and in vivo samples.

11. The method of claim 9, wherein inhibition of the serine residue of human PPAR gamma 2 corresponding to Ser-273 of murine PPAR gamma 2 is determined by analyzing the amount of the serine-phosphorylated human PPAR gamma 2.

12. The method of claim 9, wherein inhibition of the serine residue of human PPAR gamma 2 corresponding to Ser-273 of murine PPAR gamma 2 is determined by analyzing the amount of the serine-phosphorylated human PPAR gamma 2, relative to total PPAR gamma 2 and comparing the ratio to a control.

13. The method of claim 9, further comprising a step of determining whether the test compound directly binds human PPAR gamma 2.

14. The method of claim 1, wherein said PPAR gamma is murine PPAR gamma 2.

15. The method of claim 14, wherein the sample is selected from the group consisting of in vitro, ex vivo, and in vivo samples.

16. The method of claim 14, wherein inhibition of said Ser-273 phosphorylation of PPAR gamma 2 is determined by analyzing the amount of Ser-273-phosphorylated murine PPAR gamma 2.

17. The method of claim 14, wherein inhibition of Ser-273 phosphorylation is determined by analyzing the amount of Ser-273-phosphorylated murine PPAR gamma 2 relative to total PPAR gamma 2, and comparing the ratio to a control.

18. The method of claim 14, further comprising a step of determining whether the test compound directly binds murine PPAR gamma 2.

* * * * *

SEQUENCE LISTING

```
<160> NUMBER OF SEQ ID NOS: 94

<210> SEQ ID NO 1
<211> LENGTH: 475
<212> TYPE: PRT
<213> ORGANISM: Mus musculus

<400> SEQUENCE: 1

Met Val Asp Thr Glu Met Pro Phe Trp Pro Thr Asn Phe Gly Ile Ser
1               5                   10                  15

Ser Val Asp Leu Ser Val Met Glu Asp His Ser His Ser Phe Asp Ile
                20                  25                  30

Lys Pro Phe Thr Thr Val Asp Phe Ser Ser Ile Ser Ala Pro His Tyr
            35                  40                  45

Glu Asp Ile Pro Phe Thr Arg Ala Asp Pro Met Val Ala Asp Tyr Lys
        50                  55                  60

Tyr Asp Leu Lys Leu Gln Glu Tyr Gln Ser Ala Ile Lys Val Glu Pro
65                  70                  75                  80

Ala Ser Pro Pro Tyr Tyr Ser Glu Lys Thr Gln Leu Tyr Asn Arg Pro
                85                  90                  95

His Glu Glu Pro Ser Asn Ser Leu Met Ala Ile Glu Cys Arg Val Cys
            100                 105                 110

Gly Asp Lys Ala Ser Gly Phe His Tyr Gly Val His Ala Cys Glu Gly
        115                 120                 125

Cys Lys Gly Phe Phe Arg Arg Thr Ile Arg Leu Lys Leu Ile Tyr Asp
130                 135                 140

Arg Cys Asp Leu Asn Cys Arg Ile His Lys Lys Ser Arg Asn Lys Cys
145                 150                 155                 160

Gln Tyr Cys Arg Phe Gln Lys Cys Leu Ala Val Gly Met Ser His Asn
                165                 170                 175

Ala Ile Arg Phe Gly Arg Met Pro Gln Ala Glu Lys Glu Lys Leu Leu
            180                 185                 190

Ala Glu Ile Ser Ser Asp Ile Asp Gln Leu Asn Pro Glu Ser Ala Asp
        195                 200                 205

Leu Arg Ala Leu Ala Lys His Leu Tyr Asp Ser Tyr Ile Lys Ser Phe
    210                 215                 220

Pro Leu Thr Lys Ala Lys Ala Arg Ala Ile Leu Thr Gly Lys Thr Thr
225                 230                 235                 240

Asp Lys Ser Pro Phe Val Ile Tyr Asp Met Asn Ser Leu Met Met Gly
```

```
                    245                 250                 255
Glu Asp Lys Ile Lys Phe Lys His Ile Thr Pro Leu Gln Glu Gln Ser
                260                 265                 270

Lys Glu Val Ala Ile Arg Ile Phe Gln Gly Cys Gln Phe Arg Ser Val
            275                 280                 285

Glu Ala Val Gln Glu Ile Thr Glu Tyr Ala Lys Asn Ile Pro Gly Phe
        290                 295                 300

Ile Asn Leu Asp Leu Asn Asp Gln Val Thr Leu Leu Lys Tyr Gly Val
305                 310                 315                 320

His Glu Ile Ile Tyr Thr Met Leu Ala Ser Leu Met Asn Lys Asp Gly
                325                 330                 335

Val Leu Ile Ser Glu Gly Gln Gly Phe Met Thr Arg Glu Phe Leu Lys
            340                 345                 350

Asn Leu Arg Lys Pro Phe Gly Asp Phe Met Glu Pro Lys Phe Glu Phe
        355                 360                 365

Ala Val Lys Phe Asn Ala Leu Glu Leu Asp Asp Ser Asp Leu Ala Ile
    370                 375                 380

Phe Ile Ala Val Ile Ile Leu Ser Gly Asp Arg Pro Gly Leu Leu Asn
385                 390                 395                 400

Val Lys Pro Ile Glu Asp Ile Gln Asp Asn Leu Leu Gln Ala Leu Glu
                405                 410                 415

Leu Gln Leu Lys Leu Asn His Pro Glu Ser Ser Gln Leu Phe Ala Lys
            420                 425                 430

Val Leu Gln Lys Met Thr Asp Leu Arg Gln Ile Val Thr Glu His Val
        435                 440                 445

Gln Leu Leu His Val Ile Lys Lys Thr Glu Thr Asp Met Ser Leu His
    450                 455                 460

Pro Leu Leu Gln Glu Ile Tyr Lys Asp Leu Tyr
465                 470                 475

<210> SEQ ID NO 2
<211> LENGTH: 505
<212> TYPE: PRT
<213> ORGANISM: Mus musculus

<400> SEQUENCE: 2

Met Gly Glu Thr Leu Gly Asp Ser Pro Val Asp Pro Glu His Gly Ala
1               5                   10                  15

Phe Ala Asp Ala Leu Pro Met Ser Thr Ser Gln Glu Ile Thr Met Val
            20                  25                  30

Asp Thr Glu Met Pro Phe Trp Pro Thr Asn Phe Gly Ile Ser Ser Val
        35                  40                  45

Asp Leu Ser Val Met Glu Asp His Ser His Ser Phe Asp Ile Lys Pro
    50                  55                  60

Phe Thr Thr Val Asp Phe Ser Ser Ile Ser Ala Pro His Tyr Glu Asp
65                  70                  75                  80

Ile Pro Phe Thr Arg Ala Asp Pro Met Val Ala Asp Tyr Lys Tyr Asp
                85                  90                  95

Leu Lys Leu Gln Glu Tyr Gln Ser Ala Ile Lys Val Glu Pro Ala Ser
            100                 105                 110

Pro Pro Tyr Tyr Ser Glu Lys Thr Gln Leu Tyr Asn Arg Pro His Glu
        115                 120                 125

Glu Pro Ser Asn Ser Leu Met Ala Ile Glu Cys Arg Val Cys Gly Asp
    130                 135                 140
```

Lys Ala Ser Gly Phe His Tyr Gly Val His Ala Cys Glu Gly Cys Lys
145                 150                 155                 160

Gly Phe Phe Arg Arg Thr Ile Arg Leu Lys Leu Ile Tyr Asp Arg Cys
                165                 170                 175

Asp Leu Asn Cys Arg Ile His Lys Lys Ser Arg Asn Lys Cys Gln Tyr
            180                 185                 190

Cys Arg Phe Gln Lys Cys Leu Ala Val Gly Met Ser His Asn Ala Ile
        195                 200                 205

Arg Phe Gly Arg Met Pro Gln Ala Glu Lys Lys Leu Leu Ala Glu
    210                 215                 220

Ile Ser Ser Asp Ile Asp Gln Leu Asn Pro Glu Ser Ala Asp Leu Arg
225                 230                 235                 240

Ala Leu Ala Lys His Leu Tyr Asp Ser Tyr Ile Lys Ser Phe Pro Leu
                245                 250                 255

Thr Lys Ala Lys Ala Arg Ala Ile Leu Thr Gly Lys Thr Thr Asp Lys
                260                 265                 270

Ser Pro Phe Val Ile Tyr Asp Met Asn Ser Leu Met Met Gly Glu Asp
            275                 280                 285

Lys Ile Lys Phe Lys His Ile Thr Pro Leu Gln Glu Gln Ser Lys Glu
290                 295                 300

Val Ala Ile Arg Ile Phe Gln Gly Cys Gln Phe Arg Ser Val Glu Ala
305                 310                 315                 320

Val Gln Glu Ile Thr Glu Tyr Ala Lys Asn Ile Pro Gly Phe Ile Asn
                325                 330                 335

Leu Asp Leu Asn Asp Gln Val Thr Leu Leu Lys Tyr Gly Val His Glu
            340                 345                 350

Ile Ile Tyr Thr Met Leu Ala Ser Leu Met Asn Lys Asp Gly Val Leu
        355                 360                 365

Ile Ser Glu Gly Gln Gly Phe Met Thr Arg Glu Phe Leu Lys Asn Leu
370                 375                 380

Arg Lys Pro Phe Gly Asp Phe Met Glu Pro Lys Phe Glu Phe Ala Val
385                 390                 395                 400

Lys Phe Asn Ala Leu Glu Leu Asp Asp Ser Asp Leu Ala Ile Phe Ile
                405                 410                 415

Ala Val Ile Ile Leu Ser Gly Asp Arg Pro Gly Leu Leu Asn Val Lys
            420                 425                 430

Pro Ile Glu Asp Ile Gln Asp Asn Leu Leu Gln Ala Leu Glu Leu Gln
        435                 440                 445

Leu Lys Leu Asn His Pro Glu Ser Ser Gln Leu Phe Ala Lys Val Leu
450                 455                 460

Gln Lys Met Thr Asp Leu Arg Gln Ile Val Thr Glu His Val Gln Leu
465                 470                 475                 480

Leu His Val Ile Lys Lys Thr Glu Thr Asp Met Ser Leu His Pro Leu
                485                 490                 495

Leu Gln Glu Ile Tyr Lys Asp Leu Tyr
            500                 505

<210> SEQ ID NO 3
<211> LENGTH: 505
<212> TYPE: PRT
<213> ORGANISM: Homo sapiens

<400> SEQUENCE: 3

Met Gly Glu Thr Leu Gly Asp Ser Pro Ile Asp Pro Glu Ser Asp Ser
1               5                   10                  15

-continued

```
Phe Thr Asp Thr Leu Ser Ala Asn Ile Ser Gln Glu Met Thr Met Val
                 20                  25                  30

Asp Thr Glu Met Pro Phe Trp Pro Thr Asn Phe Gly Ile Ser Ser Val
             35                  40                  45

Asp Leu Ser Val Met Glu Asp His Ser His Ser Phe Asp Ile Lys Pro
 50                  55                  60

Phe Thr Val Asp Phe Ser Ser Ile Ser Thr Pro His Tyr Glu Asp
65                   70                  75                  80

Ile Pro Phe Thr Arg Thr Asp Pro Val Val Ala Asp Tyr Lys Tyr Asp
                 85                  90                  95

Leu Lys Leu Gln Glu Tyr Gln Ser Ala Ile Lys Val Glu Pro Ala Ser
             100                 105                 110

Pro Pro Tyr Tyr Ser Glu Lys Thr Gln Leu Tyr Asn Lys Pro His Glu
            115                 120                 125

Glu Pro Ser Asn Ser Leu Met Ala Ile Glu Cys Arg Val Cys Gly Asp
130                 135                 140

Lys Ala Ser Gly Phe His Tyr Gly Val His Ala Cys Glu Gly Cys Lys
145                 150                 155                 160

Gly Phe Phe Arg Arg Thr Ile Arg Leu Lys Leu Ile Tyr Asp Arg Cys
                165                 170                 175

Asp Leu Asn Cys Arg Ile His Lys Lys Ser Arg Asn Lys Cys Gln Tyr
            180                 185                 190

Cys Arg Phe Gln Lys Cys Leu Ala Val Gly Met Ser His Asn Ala Ile
        195                 200                 205

Arg Phe Gly Arg Met Pro Gln Ala Glu Lys Glu Lys Leu Leu Ala Glu
210                 215                 220

Ile Ser Ser Asp Ile Asp Gln Leu Asn Pro Glu Ser Ala Asp Leu Arg
225                 230                 235                 240

Ala Leu Ala Lys His Leu Tyr Asp Ser Tyr Ile Lys Ser Phe Pro Leu
                245                 250                 255

Thr Lys Ala Lys Ala Arg Ala Ile Leu Thr Gly Lys Thr Thr Asp Lys
            260                 265                 270

Ser Pro Phe Val Ile Tyr Asp Met Asn Ser Leu Met Met Gly Glu Asp
        275                 280                 285

Lys Ile Lys Phe Lys His Ile Thr Pro Leu Gln Glu Gln Ser Lys Glu
290                 295                 300

Val Ala Ile Arg Ile Phe Gln Gly Cys Gln Phe Arg Ser Val Glu Ala
305                 310                 315                 320

Val Gln Glu Ile Thr Glu Tyr Ala Lys Ser Ile Pro Gly Phe Val Asn
                325                 330                 335

Leu Asp Leu Asn Asp Gln Val Thr Leu Leu Lys Tyr Gly Val His Glu
            340                 345                 350

Ile Ile Tyr Thr Met Leu Ala Ser Leu Met Asn Lys Asp Gly Val Leu
        355                 360                 365

Ile Ser Glu Gly Gln Gly Phe Met Thr Arg Glu Phe Leu Lys Ser Leu
370                 375                 380

Arg Lys Pro Phe Gly Asp Phe Met Glu Pro Lys Phe Glu Phe Ala Val
385                 390                 395                 400

Lys Phe Asn Ala Leu Glu Leu Asp Asp Ser Asp Leu Ala Ile Phe Ile
                405                 410                 415

Ala Val Ile Ile Leu Ser Gly Asp Arg Pro Gly Leu Leu Asn Val Lys
            420                 425                 430
```

```
Pro Ile Glu Asp Ile Gln Asp Asn Leu Leu Gln Ala Leu Glu Leu Gln
            435                 440                 445

Leu Lys Leu Asn His Pro Glu Ser Ser Gln Leu Phe Ala Lys Leu Leu
450                 455                 460

Gln Lys Met Thr Asp Leu Arg Gln Ile Val Thr Glu His Val Gln Leu
465                 470                 475                 480

Leu Gln Val Ile Lys Lys Thr Glu Thr Asp Met Ser Leu His Pro Leu
            485                 490                 495

Leu Gln Glu Ile Tyr Lys Asp Leu Tyr
            500                 505

<210> SEQ ID NO 4
<211> LENGTH: 505
<212> TYPE: PRT
<213> ORGANISM: Bos sp.

<400> SEQUENCE: 4

Met Gly Glu Thr Leu Gly Asp Ala Leu Ile Asp Pro Glu Ser Glu Pro
1               5                   10                  15

Phe Ala Val Thr Val Ser Ala Arg Thr Ser Gln Glu Ile Thr Met Val
            20                  25                  30

Asp Thr Glu Met Pro Phe Trp Pro Thr Asn Phe Gly Ile Ser Ser Val
        35                  40                  45

Asp Leu Ser Met Met Asp Asp His Ser His Ala Phe Asp Ile Lys Pro
50                  55                  60

Phe Thr Thr Val Asp Phe Ser Ser Ile Ser Thr Pro His Tyr Glu Asp
65                  70                  75                  80

Ile Pro Phe Pro Arg Ala Asp Pro Met Val Ala Asp Tyr Lys Tyr Asp
            85                  90                  95

Leu Lys Leu Gln Glu Tyr Gln Ser Ala Ile Lys Val Glu Pro Val Ser
            100                 105                 110

Pro Pro Tyr Tyr Ser Glu Lys Thr Gln Leu Tyr Ser Lys Pro His Glu
        115                 120                 125

Glu Pro Ser Asn Ser Leu Met Ala Ile Glu Cys Arg Val Cys Gly Asp
130                 135                 140

Lys Ala Ser Gly Phe His Tyr Gly Val His Ala Cys Glu Gly Cys Lys
145                 150                 155                 160

Gly Phe Phe Arg Arg Thr Ile Arg Leu Lys Leu Ile Tyr Asp Arg Cys
            165                 170                 175

Asp Leu Asn Cys Arg Ile His Lys Lys Ser Arg Asn Lys Cys Gln Tyr
        180                 185                 190

Cys Arg Phe Gln Lys Cys Leu Ala Val Gly Met Ser His Asn Ala Ile
    195                 200                 205

Arg Phe Gly Arg Met Pro Gln Ala Glu Lys Glu Lys Leu Leu Ala Glu
210                 215                 220

Ile Ser Ser Asp Ile Asp Gln Leu Asn Pro Glu Ser Ala Asp Leu Arg
225                 230                 235                 240

Ala Leu Ala Lys His Leu Tyr Asp Ser Tyr Ile Lys Ser Phe Pro Leu
            245                 250                 255

Thr Lys Ala Lys Ala Arg Ala Ile Leu Thr Gly Lys Thr Thr Asp Lys
        260                 265                 270

Ser Pro Phe Val Ile Tyr Asp Met Asn Ser Leu Met Met Gly Glu Asp
    275                 280                 285

Lys Ile Lys Phe Lys His Ile Ser Pro Leu Gln Glu Pro Ser Lys Glu
290                 295                 300
```

Val Ala Ile Arg Ile Phe Gln Gly Cys Gln Phe Arg Ser Val Glu Ala
305                 310                 315                 320

Val Gln Glu Ile Thr Glu Tyr Ala Lys Asn Ile Pro Gly Phe Val Asn
            325                 330                 335

Leu Asp Leu Asn Asp Gln Val Thr Leu Leu Lys Tyr Gly Val His Glu
            340                 345                 350

Ile Ile Tyr Thr Met Leu Ala Ser Leu Met Asn Lys Asp Gly Val Leu
            355                 360                 365

Ile Ser Glu Gly Gln Gly Phe Met Thr Arg Glu Phe Leu Lys Ser Leu
370                 375                 380

Arg Lys Pro Phe Gly Asp Phe Met Glu Pro Lys Phe Glu Phe Ala Val
385                 390                 395                 400

Lys Phe Asn Ala Leu Glu Leu Asp Asp Ser Asp Leu Ala Ile Phe Ile
            405                 410                 415

Ala Val Ile Ile Leu Ser Gly Asp Arg Pro Gly Leu Leu Asn Val Lys
            420                 425                 430

Pro Ile Glu Asp Ile Gln Asp Asn Leu Leu Gln Ala Leu Glu Leu Gln
            435                 440                 445

Leu Lys Leu Asn His Pro Glu Ser Ser Gln Leu Phe Ala Lys Leu Leu
450                 455                 460

Gln Lys Met Thr Asp Leu Arg Gln Ile Val Thr Glu His Val Gln Leu
465                 470                 475                 480

Leu Gln Val Ile Lys Lys Thr Glu Thr Asp Met Ser Leu His Pro Leu
            485                 490                 495

Leu Gln Glu Ile Tyr Lys Asp Leu Tyr
            500                 505

<210> SEQ ID NO 5
<211> LENGTH: 475
<212> TYPE: PRT
<213> ORGANISM: Oryctolagus sp.

<400> SEQUENCE: 5

Met Val Asp Thr Glu Met Pro Phe Trp Pro Thr Asn Phe Gly Ile Gly
1               5                   10                  15

Ser Val Asp Leu Ser Val Met Asp Asp His Ser His Ser Phe Asp Ile
            20                  25                  30

Lys Pro Phe Thr Thr Val Asp Phe Ser Ser Ile Ser Ala Pro His Tyr
            35                  40                  45

Glu Asp Leu Pro Phe Ala Arg Ala Asp Pro Met Val Ala Asp Tyr Lys
50                  55                  60

Tyr Asp Leu Lys Leu Gln Glu Tyr Gln Ser Ala Ile Lys Val Glu Pro
65                  70                  75                  80

Ala Ser Pro Pro Tyr Tyr Ser Glu Lys Thr Gln Leu Tyr Asn Lys Thr
            85                  90                  95

His Glu Glu Pro Ser Asn Ser Leu Met Ala Ile Glu Cys Arg Val Cys
            100                 105                 110

Ser Asp Lys Ala Ser Gly Phe His Tyr Gly Val His Ala Cys Glu Gly
            115                 120                 125

Cys Lys Gly Phe Phe Arg Arg Thr Ile Arg Leu Lys Leu Ile Tyr Asp
            130                 135                 140

Arg Cys Asp Leu Asn Cys Arg Ile His Lys Lys Ser Arg Asn Lys Cys
145                 150                 155                 160

Gln Tyr Cys Arg Phe Gln Lys Cys Leu Ala Val Gly Met Ser His Asn

```
                165                 170                 175
Ala Ile Arg Phe Gly Arg Met Pro Gln Ala Glu Lys Glu Lys Leu Leu
            180                 185                 190

Ala Glu Ile Ser Ser Asp Ile Asp Gln Leu Asn Pro Glu Ser Ala Asp
            195                 200                 205

Leu Arg Ala Leu Ala Lys His Leu Tyr Asp Ser Tyr Ile Lys Ser Phe
        210                 215                 220

Pro Leu Thr Lys Ala Lys Ala Arg Ala Ile Leu Thr Gly Lys Thr Thr
225                 230                 235                 240

Asp Lys Ser Pro Phe Val Ile Tyr Asp Met Asn Ser Leu Met Met Gly
                245                 250                 255

Glu Asp Lys Ile Lys Phe Lys His Ile Thr Pro Leu Gln Glu Gln Ser
            260                 265                 270

Lys Glu Val Ala Ile Arg Ile Phe Gln Gly Cys Gln Phe Arg Ser Val
            275                 280                 285

Glu Ala Val Gln Glu Ile Thr Glu Tyr Ala Lys Asn Ile Pro Gly Phe
        290                 295                 300

Val Ser Leu Asp Leu Asn Asp Gln Val Thr Leu Leu Lys Tyr Gly Val
305                 310                 315                 320

His Glu Ile Ile Tyr Thr Met Leu Ala Ser Leu Met Asn Lys Asp Gly
                325                 330                 335

Val Leu Ile Ser Glu Gly Gln Gly Phe Met Thr Arg Glu Phe Leu Lys
            340                 345                 350

Ser Leu Arg Lys Pro Phe Gly Asp Phe Met Glu Pro Lys Phe Glu Phe
        355                 360                 365

Ala Val Lys Phe Asn Ala Leu Glu Leu Asp Asp Ser Asp Leu Ala Ile
        370                 375                 380

Phe Ile Ala Val Ile Ile Leu Ser Gly Asp Arg Pro Gly Leu Leu Asn
385                 390                 395                 400

Val Lys Pro Ile Glu Asp Ile Gln Asp Asn Leu Leu Gln Ala Leu Glu
                405                 410                 415

Leu Gln Leu Lys Leu Asn His Pro Glu Ala Ser Gln Leu Phe Ala Lys
            420                 425                 430

Leu Leu Gln Lys Met Thr Asp Leu Arg Gln Ile Val Thr Glu His Val
        435                 440                 445

Gln Leu Leu Gln Val Ile Lys Lys Thr Glu Thr Asp Met Ser Leu His
        450                 455                 460

Pro Leu Leu Gln Glu Ile Tyr Lys Asp Leu Tyr
465                 470                 475

<210> SEQ ID NO 6
<211> LENGTH: 504
<212> TYPE: PRT
<213> ORGANISM: Sus sp.

<400> SEQUENCE: 6

Met Gly Glu Thr Leu Gly Asp Ser Leu Ile Asp Pro Glu Ser Asp Ala
1               5                   10                  15

Phe Asp Thr Leu Ser Ala Asn Ile Ser Gln Glu Val Thr Met Val Asp
            20                  25                  30

Thr Glu Met Pro Phe Trp Pro Thr Asn Phe Gly Ile Ser Ser Val Asp
        35                  40                  45

Leu Ser Val Met Asp Asp His Ser His Ser Phe Asp Ile Lys Pro Phe
    50                  55                  60
```

Thr Thr Val Asp Phe Ser Ser Ile Ser Thr Pro His Tyr Glu Asp Ile
65                  70                  75                  80

Pro Phe Pro Arg Ala Asp Pro Met Val Ala Asp Tyr Lys Tyr Asp Leu
            85                  90                  95

Lys Leu Gln Asp Tyr Gln Ser Ala Ile Lys Val Glu Pro Val Ser Pro
            100                 105                 110

Pro Tyr Tyr Ser Glu Lys Thr Gln Leu Tyr Asn Lys Pro His Glu Glu
            115                 120                 125

Pro Ser Asn Ser Leu Met Ala Ile Glu Cys Arg Val Cys Gly Asp Lys
            130                 135                 140

Ala Ser Gly Phe His Tyr Gly Val His Ala Cys Glu Gly Cys Lys Gly
145                 150                 155                 160

Phe Phe Arg Arg Thr Ile Arg Leu Lys Leu Ile Tyr Asp Arg Cys Asp
                165                 170                 175

Leu Asn Cys Arg Ile His Lys Lys Ser Arg Asn Lys Cys Gln Tyr Cys
            180                 185                 190

Arg Phe Gln Lys Cys Leu Ala Val Gly Met Ser His Asn Ala Ile Arg
            195                 200                 205

Phe Gly Arg Met Pro Gln Ala Glu Lys Glu Lys Leu Leu Ala Glu Ile
210                 215                 220

Ser Ser Asp Ile Asp Gln Leu Asn Pro Glu Ser Ala Asp Leu Arg Ala
225                 230                 235                 240

Leu Ala Lys His Leu Tyr Asp Ser Tyr Ile Lys Ser Phe Pro Leu Thr
                245                 250                 255

Lys Ala Lys Ala Arg Ala Ile Leu Thr Gly Lys Thr Thr Asp Lys Ser
            260                 265                 270

Pro Phe Val Ile Tyr Asp Met Asn Ser Leu Met Met Gly Glu Asp Lys
            275                 280                 285

Ile Lys Phe Lys His Ile Thr Pro Leu Gln Glu Gln Ser Lys Glu Val
            290                 295                 300

Ala Ile Arg Ile Phe Gln Gly Cys Gln Phe Arg Ser Val Glu Ala Val
305                 310                 315                 320

Gln Glu Ile Thr Glu Tyr Ala Lys Asn Ile Pro Gly Phe Val Asn Leu
            325                 330                 335

Asp Leu Asn Asp Gln Val Thr Leu Leu Lys Tyr Gly Val His Glu Ile
            340                 345                 350

Ile Tyr Thr Met Leu Ala Ser Leu Met Asn Lys Asp Gly Val Leu Ile
            355                 360                 365

Ser Glu Gly Gln Gly Phe Met Thr Arg Glu Phe Leu Lys Ser Leu Arg
370                 375                 380

Lys Pro Phe Gly Asp Phe Met Glu Pro Lys Phe Glu Phe Ala Val Lys
385                 390                 395                 400

Phe Asn Ala Leu Glu Leu Asp Asp Ser Asp Leu Ala Ile Phe Ile Ala
            405                 410                 415

Val Ile Ile Leu Ser Gly Asp Arg Pro Gly Leu Leu Asn Val Lys Pro
            420                 425                 430

Ile Glu Asp Ile Gln Asp Asn Leu Leu Gln Ala Leu Glu Leu Gln Leu
            435                 440                 445

Lys Leu Asn His Pro Glu Ser Ser Gln Leu Phe Ala Lys Leu Leu Gln
            450                 455                 460

Lys Met Thr Asp Leu Arg Gln Ile Val Thr Glu His Val Gln Leu Leu
465                 470                 475                 480

Gln Val Ile Lys Lys Thr Glu Thr Asp Met Ser Leu His Pro Leu Leu

```
                     485                 490                 495
Gln Glu Ile Tyr Lys Asp Leu Tyr
                500

<210> SEQ ID NO 7
<211> LENGTH: 475
<212> TYPE: PRT
<213> ORGANISM: Gallus gallus

<400> SEQUENCE: 7

Met Val Asp Thr Glu Met Pro Phe Trp Pro Val Asn Phe Gly Ile Ser
1               5                   10                  15

Pro Val Asp Leu Ser Ala Met Asp His Met His Ser Phe Asp Ile
            20                  25                  30

Lys Pro Phe Thr Thr Val Asp Phe Ser Ser Ile Ser Ser Pro His Tyr
            35                  40                  45

Glu Asp Ile Pro Leu Gly Arg Ala Asp Gln Thr Ser Ile Asp Tyr Lys
        50                  55                  60

Tyr Asp Ile Lys Leu Gln Asp Cys Gln Ser Ala Ile Lys Met Glu Pro
65                  70                  75                  80

Pro Ser Pro Pro Tyr Phe Ser Glu Lys Val Gln Leu Tyr Asn Lys Pro
                85                  90                  95

His Glu Glu Ser Ser Asn Ser Leu Met Ala Ile Glu Cys Arg Val Cys
            100                 105                 110

Gly Asp Lys Ala Ser Gly Phe His Tyr Gly Val His Ala Cys Glu Gly
        115                 120                 125

Cys Lys Gly Phe Phe Arg Arg Thr Ile Arg Leu Lys Leu Ile Tyr Asp
130                 135                 140

Arg Cys Asp Leu Asn Cys Arg Ile His Lys Lys Ser Arg Asn Lys Cys
145                 150                 155                 160

Gln Tyr Cys Arg Phe Gln Lys Cys Leu Ala Val Gly Met Ser His Asn
                165                 170                 175

Ala Ile Arg Phe Gly Arg Met Pro Gln Ala Glu Lys Glu Lys Leu Leu
            180                 185                 190

Ala Glu Ile Ser Ser Asp Ile Asp Gln Leu Asn Pro Glu Ser Ala Asp
        195                 200                 205

Leu Arg Ala Leu Ala Lys His Leu Tyr Asp Ser Tyr Ile Lys Ser Phe
210                 215                 220

Pro Leu Thr Lys Ala Lys Ala Arg Ala Ile Leu Thr Gly Lys Thr Thr
225                 230                 235                 240

Asp Lys Ser Pro Phe Val Ile Tyr Asp Met Asn Ser Leu Arg Met Gly
                245                 250                 255

Glu Asp Gln Ile Lys Cys Lys His Ala Ser Pro Leu Gln Glu Gln Asn
            260                 265                 270

Lys Glu Val Ala Ile Arg Ile Phe Gln Arg Cys Gln Phe Arg Ser Val
        275                 280                 285

Glu Ala Val Gln Glu Ile Thr Glu Phe Ala Lys Asn Ile Pro Gly Phe
    290                 295                 300

Val Asn Leu Asp Leu Asn Asp Gln Val Thr Leu Leu Lys Tyr Gly Val
305                 310                 315                 320

His Glu Ile Ile Tyr Thr Leu Leu Ala Ser Leu Met Asn Lys Asp Gly
                325                 330                 335

Val Leu Ile Ser Asp Gly Gln Gly Phe Met Thr Arg Glu Phe Leu Lys
            340                 345                 350
```

```
Ser Leu Arg Lys Pro Phe Cys Asp Phe Met Glu Pro Lys Phe Glu Phe
            355                 360                 365

Ala Val Lys Phe Asn Ala Leu Glu Leu Asp Asp Ser Asp Leu Ala Ile
            370                 375                 380

Phe Ile Ala Val Ile Ile Leu Ser Gly Asp Arg Pro Gly Leu Leu Asn
385                 390                 395                 400

Val Lys Pro Ile Glu Asp Ile Gln Asp Asn Leu Leu Gln Ala Leu Glu
                405                 410                 415

Leu Gln Leu Lys Leu Asn His Pro Glu Ser Ser Gln Leu Phe Ala Lys
            420                 425                 430

Leu Leu Gln Lys Met Thr Asp Leu Arg Gln Ile Val Thr Glu His Val
            435                 440                 445

Gln Leu Leu Gln Ile Ile Lys Lys Thr Glu Thr Asp Met Ser Leu His
    450                 455                 460

Pro Leu Leu Gln Glu Ile Tyr Lys Asp Leu Tyr
465                 470                 475

<210> SEQ ID NO 8
<211> LENGTH: 468
<212> TYPE: PRT
<213> ORGANISM: Mus musculus

<400> SEQUENCE: 8

Met Val Asp Thr Glu Ser Pro Ile Cys Pro Leu Ser Pro Leu Glu Ala
1               5                   10                  15

Asp Asp Leu Glu Ser Pro Leu Ser Glu Glu Phe Leu Gln Glu Met Gly
            20                  25                  30

Asn Ile Gln Glu Ile Ser Gln Ser Ile Gly Glu Glu Ser Ser Gly Ser
            35                  40                  45

Phe Gly Phe Ala Asp Tyr Gln Tyr Leu Gly Ser Cys Pro Gly Ser Glu
    50                  55                  60

Gly Ser Val Ile Thr Asp Thr Leu Ser Pro Ala Ser Ser Pro Ser Ser
65                  70                  75                  80

Val Ser Cys Pro Val Ile Pro Ala Ser Thr Asp Glu Ser Pro Gly Ser
                85                  90                  95

Ala Leu Asn Ile Glu Cys Arg Ile Cys Gly Asp Lys Ala Ser Gly Tyr
            100                 105                 110

His Tyr Gly Val His Ala Cys Glu Gly Cys Lys Gly Phe Phe Arg Arg
            115                 120                 125

Thr Ile Arg Leu Lys Leu Val Tyr Asp Lys Cys Asp Arg Ser Cys Lys
    130                 135                 140

Ile Gln Lys Lys Asn Arg Asn Lys Cys Gln Tyr Cys Arg Phe His Lys
145                 150                 155                 160

Cys Leu Ser Val Gly Met Ser His Asn Ala Ile Arg Phe Gly Arg Met
                165                 170                 175

Pro Arg Ser Glu Lys Ala Lys Leu Lys Ala Glu Ile Leu Thr Cys Glu
            180                 185                 190

His Asp Leu Lys Asp Ser Glu Thr Ala Asp Leu Lys Ser Leu Gly Lys
            195                 200                 205

Arg Ile His Glu Ala Tyr Leu Lys Asn Phe Asn Met Asn Lys Val Lys
    210                 215                 220

Ala Arg Val Ile Leu Ala Gly Lys Thr Ser Asn Asn Pro Pro Phe Val
225                 230                 235                 240

Ile His Asp Met Glu Thr Leu Cys Met Ala Glu Lys Thr Leu Val Ala
                245                 250                 255
```

```
Lys Met Val Ala Asn Gly Val Glu Asp Lys Glu Ala Glu Val Arg Phe
            260                 265                 270

Phe His Cys Cys Gln Cys Met Ser Val Glu Thr Val Thr Glu Leu Thr
        275                 280                 285

Glu Phe Ala Lys Ala Ile Pro Gly Phe Ala Asn Leu Asp Leu Asn Asp
    290                 295                 300

Gln Val Thr Leu Leu Lys Tyr Gly Val Tyr Glu Ala Ile Phe Thr Met
305                 310                 315                 320

Leu Ser Ser Leu Met Asn Lys Asp Gly Met Leu Ile Ala Tyr Gly Asn
                325                 330                 335

Gly Phe Ile Thr Arg Glu Phe Leu Lys Asn Leu Arg Lys Pro Phe Cys
            340                 345                 350

Asp Ile Met Glu Pro Lys Phe Asp Phe Ala Met Lys Phe Asn Ala Leu
        355                 360                 365

Glu Leu Asp Asp Ser Asp Ile Ser Leu Phe Val Ala Ala Ile Ile Cys
    370                 375                 380

Cys Gly Asp Arg Pro Gly Leu Leu Asn Ile Gly Tyr Ile Glu Lys Leu
385                 390                 395                 400

Gln Glu Gly Ile Val His Val Leu Lys Leu His Leu Gln Ser Asn His
                405                 410                 415

Pro Asp Asp Thr Phe Leu Phe Pro Lys Leu Leu Gln Lys Met Val Asp
            420                 425                 430

Leu Arg Gln Leu Val Thr Glu His Ala Gln Leu Val Gln Val Ile Lys
        435                 440                 445

Lys Thr Glu Ser Asp Ala Ala Leu His Pro Leu Leu Gln Glu Ile Tyr
    450                 455                 460

Arg Asp Met Tyr
465

<210> SEQ ID NO 9
<211> LENGTH: 440
<212> TYPE: PRT
<213> ORGANISM: Mus musculus

<400> SEQUENCE: 9

Met Glu Gln Pro Gln Glu Glu Thr Pro Glu Ala Arg Glu Glu Glu Lys
1               5                   10                  15

Glu Glu Val Ala Met Gly Asp Gly Ala Pro Glu Leu Asn Gly Gly Pro
            20                  25                  30

Glu His Thr Leu Pro Ser Ser Ser Cys Ala Asp Leu Ser Gln Asn Ser
        35                  40                  45

Ser Pro Ser Ser Leu Leu Asp Gln Leu Gln Met Gly Cys Asp Gly Ala
    50                  55                  60

Ser Gly Gly Ser Leu Asn Met Glu Cys Arg Val Cys Gly Asp Lys Ala
65                  70                  75                  80

Ser Gly Phe His Tyr Gly Val His Ala Cys Glu Gly Cys Lys Gly Phe
                85                  90                  95

Phe Arg Arg Thr Ile Arg Met Lys Leu Glu Tyr Glu Lys Cys Asp Arg
            100                 105                 110

Ile Cys Lys Ile Gln Lys Lys Asn Arg Asn Lys Cys Gln Tyr Cys Arg
        115                 120                 125

Phe Gln Lys Cys Leu Ala Leu Gly Met Ser His Asn Ala Ile Arg Phe
    130                 135                 140

Gly Arg Met Pro Glu Ala Glu Lys Arg Lys Leu Val Ala Gly Leu Thr
```

```
                145                 150                 155                 160
Ala Ser Glu Gly Cys Gln His Asn Pro Gln Leu Ala Asp Leu Lys Ala
                165                 170                 175

Phe Ser Lys His Ile Tyr Asn Ala Tyr Leu Lys Asn Phe Asn Met Thr
                180                 185                 190

Lys Lys Lys Ala Arg Ser Ile Leu Thr Gly Lys Ser Ser His Asn Ala
                195                 200                 205

Pro Phe Val Ile His Asp Ile Glu Thr Leu Trp Gln Ala Lys Gly
210                 215                 220

Leu Val Trp Lys Gln Leu Val Asn Gly Leu Pro Pro Tyr Asn Glu Ile
225                 230                 235                 240

Ser Val His Val Phe Tyr Arg Cys Gln Ser Thr Thr Val Glu Thr Val
                245                 250                 255

Arg Glu Leu Thr Glu Phe Ala Lys Asn Ile Pro Asn Phe Ser Ser Leu
                260                 265                 270

Phe Leu Asn Asp Gln Val Thr Leu Leu Lys Tyr Gly Val His Glu Ala
                275                 280                 285

Ile Phe Ala Met Leu Ala Ser Ile Val Asn Lys Asp Gly Leu Leu Val
                290                 295                 300

Ala Asn Gly Ser Gly Phe Val Thr His Glu Phe Leu Arg Ser Leu Arg
305                 310                 315                 320

Lys Pro Phe Ser Asp Ile Ile Glu Pro Lys Phe Glu Phe Ala Val Lys
                325                 330                 335

Phe Asn Ala Leu Glu Leu Asp Asp Ser Asp Leu Ala Leu Phe Ile Ala
                340                 345                 350

Ala Ile Ile Leu Cys Gly Asp Arg Pro Gly Leu Met Asn Val Pro Gln
                355                 360                 365

Val Glu Ala Ile Gln Asp Thr Ile Leu Arg Ala Leu Glu Phe His Leu
                370                 375                 380

Gln Val Asn His Pro Asp Ser Gln Tyr Leu Phe Pro Lys Leu Leu Gln
385                 390                 395                 400

Lys Met Ala Asp Leu Arg Gln Leu Val Thr Glu His Ala Gln Met Met
                405                 410                 415

Gln Trp Leu Lys Lys Thr Glu Ser Glu Thr Leu Leu His Pro Leu Leu
                420                 425                 430

Gln Glu Ile Tyr Lys Asp Met Tyr
                435                 440

<210> SEQ ID NO 10
<211> LENGTH: 1769
<212> TYPE: DNA
<213> ORGANISM: Mus musculus

<400> SEQUENCE: 10
caaaacacca gtgtgaatta cagcaaatct ctgttttatg ctgttatggg tgaaactctg      60
ggagattctc ctgttgaccc agagcatggt gccttcgctg atgcactgcc tatgagcact     120
tcacaagaaa ttaccatggt tgacacagag atgccattct ggcccaccaa cttcggaatc     180
agctctgtgg acctctccgt gatggaagac cactcgcatt cctttgacat caagcccttt     240
accacagttg atttctccag catttctgct ccacactatg aagacattcc attcacaaga     300
gctgacccaa tggttgctga ttacaaatat gacctgaagc tccaagaata ccaaagtgcg     360
atcaaagtag aacctgcatc tccaccttat tattctgaaa agacccagct ctacaacagg     420
cctcatgaag aaccttctaa ctcccctcatg gccattgagt gccgagtctg tgggataaaa     480
```

```
gcatcaggct tccactatgg agttcatgct tgtgaaggat gcaagggttt tttccgaaga      540
accatccgat tgaagcttat ttatgatagg tgtgatctta actgccggat ccacaaaaaa      600
agtagaaata aatgtcagta ctgtcggttt cagaagtgcc ttgctgtggg gatgtctcac      660
aatgccatca ggtttgggcg gatgccacag gccgagaagg agaagctgtt ggcggagatc      720
tccagtgata tcgaccagct gaacccagag tctgctgatc tgcgagccct ggcaaagcat      780
ttgtatgact catacataaa gtccttcccg ctgaccaaag ccaaggcgag ggcgatcttg      840
acaggaaaga caacggacaa atcaccattt gtcatctacg acatgaattc cttaatgatg      900
ggagaagata aaatcaagtt caaacatatc acccccctgc aggagcagag caaagaggtg      960
gccatccgaa ttttttcaagg gtgccagttt cgatccgtag aagccgtgca agagatcaca     1020
gagtatgcca aaaatatccc tggtttcatt aaccttgatt tgaatgacca agtgactctg     1080
ctcaagtatg gtgtccatga gatcatctac acgatgctgg cctccctgat gaataaagat     1140
ggagtcctca tctcagaggg ccaaggattc atgaccaggg agttcctcaa aagcctgcgg     1200
aagccctttg gtgactttat ggagcctaag tttgagtttg ctgtgaagtt caatgcactg     1260
gaattagatg acagtgactt ggctatattt atagctgtca ttattctcag tggagaccgc     1320
ccaggcttgc tgaacgtgaa gcccatcgag gacatccaag acaacctgct gcaggccctg     1380
gaactgcagc tcaagctgaa tcacccagag tcctctcagc tgttcgccaa ggtgctccag     1440
aagatgacag acctcaggca gatcgtcaca gagcacgtgc agctactgca tgtgatcaag     1500
aagacagaga cagacatgag ccttcacccc ctgctccagg agatctacaa ggacttgtat     1560
tagcaggaaa gtcccacccg ctgacaacgt gttccttcta ttgattgcac tattatttg      1620 agggaaaaaa atctgacacc taagaaattt actgtgaaaa agcatttaaa aacaaaaagt     1680
tttagaacat gatctatttt atgcatattg tttataaaga tacatttaca atttactttt     1740
aatattaaaa attaccacat tataaaatt                                        1769
```

<210> SEQ ID NO 11  
<211> LENGTH: 1518  
<212> TYPE: DNA  
<213> ORGANISM: Mus musculus

<400> SEQUENCE: 11

```
atgggtgaaa ctctgggaga ttctcctgtt gacccagagc atggtgcctt cgctgatgca       60
ctgcctatga gcacttcaca agaaattacc atggttgaca cagagatgcc attctggccc      120
accaacttcg gaatcagctc tgtggaccct ccgtgatgg aagaccactc gcattccttt       180
gacatcaagc cctttaccac agttgatttc tccagcattt ctgctccaca ctatgaagac      240
attccattca aagagctgac cccaatggtt gctgattaca aatatgacct gaagctccaa      300
gaataccaaa gtgcgatcaa agtagaacct gcatctccac cttattattc tgaaaagacc      360
cagctctaca caggcctca tgaagaacct tctaactccc tcatggccat tgagtgccga      420
gtctgtgggg ataaagcatc aggcttccac tatggagttc atgcttgtga aggatgcaag      480 ggtttttttcc gaagaaccat ccgattgaag cttatttatg ataggtgtga tcttaactgc      540
cggatccaca aaaaagtag aaataaatgt cagtactgtc ggtttcagaa gtgccttgct      600 gtgggggatgt ctcacaatgc catcaggttt gggcggatgc cacaggccga gaaggagaag     660
ctgttggcgg agatctccag tgatatcgac cagctgaacc cagagtctgc tgatctgcga     720
gccctggcaa agcatttgta tgactcatac ataaagtcct cccgctgac caaagccaag     780
```

```
gcgagggcga tcttgacagg aaagacaacg gacaaatcac catttgtcat ctacgacatg    840
aattccttaa tgatgggaga agataaaatc aagttcaaac atatcacccc cctgcaggag    900
cagagcaaag aggtggccat ccgaattttt caagggtgcc agtttcgatc cgtagaagcc    960
gtgcaagaga tcacagagta tgccaaaaat atccctggtt tcattaacct tgatttgaat   1020
gaccaagtga ctctgctcaa gtatggtgtc catgagatca tctacacgat gctggcctcc   1080
ctgatgaata aagatggagt cctcatctca gagggccaag gattcatgac cagggagttc   1140
ctcaaaagcc tgcggaagcc cttttggtgac tttatggagc taagtttga gtttgctgtg    1200 aagttcaatg cactggaatt agatgacagt gacttggcta tatttatagc tgtcattatt   1260
ctcagtggag accgcccagg cttgctgaac gtgaagccca tcgaggacat ccaagacaac   1320
ctgctgcagg ccctgaact gcagctcaag ctgaatcacc cagagtcctc tcagctgttc     1380
gccaaggtgc tccagaagat gacagacctc aggcagatcg tcacagagca cgtgcagcta   1440
ctgcatgtga tcaagaagac agagacagac atgagccttc accccctgct ccaggagatc   1500
tacaaggact tgtattag                                                 1518

<210> SEQ ID NO 12
<211> LENGTH: 1820
<212> TYPE: DNA
<213> ORGANISM: Homo sapiens

<400> SEQUENCE: 12
ttcaagtctt tttcttttaa cggattgatc ttttgctaga tagagacaaa atatcagtgt     60
gaattacagc aaaccctat tccatgctgt tatgggtgaa actctgggag attctcctat    120
tgacccagaa agcgattcct tcactgatac actgtctgca acatatcac aagaaatgac     180 catggttgac acagagatgc cattctggcc caccaacttt gggatcagct ccgtggatct    240
ctccgtaatg gaagaccact cccactcctt tgatatcaag cccttcacta ctgttgactt    300
ctccagcatt tctactccac attacgaaga cattccattc acaagaacag atccagtggt    360
tgcagattac aagtatgacc tgaaacttca agagtaccaa agtgcaatca agtggagcc    420 tgcatctcca ccttattatt ctgagaagac tcagctctac aataagcctc atgaagagcc    480
ttccaactcc ctcatggcaa ttgaatgtcg tgtctgtgga gataaagctt ctggatttca    540
ctatggagtt catgcttgtg aaggatgcaa gggtttcttc cggagaacaa tcagattgaa    600
gcttatctat gacagatgtg atcttaactg tcggatccac aaaaaaagta gaaataaatg    660
tcagtactgt cggtttcaga aatgccttgc agtggggatg tctcataatg ccatcaggtt    720
tgggcggatg ccacaggccg agaaggagaa gctgttggcg gagatctcca gtgatatcga    780
ccagctgaat ccagagtccg ctgacctccg ggccctggca aaacatttgt atgactcata    840
cataaagtcc ttcccgctga ccaaagcaaa ggcgagggcg atcttgacag aaagacaac    900 agacaaatca ccattcgtta tctatgacat gaattcctta tgatgggag aagataaaat    960 caagttcaaa cacatcaccc cctgcagga gcagagcaaa gaggtggcca tccgcatctt   1020
tcagggctgc cagtttcgct ccgtggaggc tgtgcaggag atcacagagt atgccaaaag   1080
cattcctggt tttgtaaatc ttgacttgaa cgaccaagta actctcctca aatatggagt   1140
ccacgagatc atttacacaa tgctggcctc cttgatgaat aaagatgggg ttctcatatc   1200
cgagggccaa ggcttcatga caagggagtt ctaaagagc ctgcgaaagc cttttggtga    1260
ctttatggag cccaagtttg agtttgctgt gaagttcaat gcactggaat tagatgacag   1320
cgacttggca atatttattg ctgtcattat tctcagtgga gaccgcccag gtttgctgaa   1380
```

```
tgtgaagccc attgaagaca ttcaagacaa cctgctacaa gccctggagc tccagctgaa    1440
gctgaaccac cctgagtcct cacagctgtt tgccaagctg ctccagaaaa tgacagacct    1500
cagacagatt gtcacggaac acgtgcagct actgcaggtg atcaagaaga cggagacaga    1560
catgagtctt cacccgctcc tgcaggagat ctacaaggac ttgtactagc agagagtcct    1620
gagccactgc caacatttcc cttcttccag ttgcactatt ctgagggaaa atctgacacc    1680
taagaaattt actgtgaaaa agcattttaa aaagaaaagg ttttagaata tgatctattt    1740
tatgcatatt gtttataaag acacatttac aatttacttt taatattaaa aattaccata    1800
ttatgaaatt gctgatagta                                                1820
```

<210> SEQ ID NO 13
<211> LENGTH: 1518
<212> TYPE: DNA
<213> ORGANISM: Homo sapiens

<400> SEQUENCE: 13

```
atgggtgaaa ctctgggaga ttctcctatt gacccagaaa gcgattcctt cactgataca      60
ctgtctgcaa acatatcaca agaaatgacc atggttgaca cagagatgcc attctggccc     120
accaactttg ggatcagctc cgtggatctc tccgtaatgg aagaccactc ccactccttt     180
gatatcaagc ccttcactac tgttgacttc tccagcattt ctactccaca ttacgaagac     240
attccattca caagaacaga tccagtggtt gcagattaca agtatgacct gaaacttcaa     300
gagtaccaaa gtgcaatcaa agtggagcct gcatctccac cttattattc tgagaagact     360
cagctctaca ataagcctca tgaagagcct tccaactccc tcatggcaat gaatgtcgt     420 gtctgtggag ataaagcttc tggatttcac tatggagttc atgcttgtga aggatgcaag     480
ggtttcttcc ggagaacaat cagattgaag cttatctatg acagatgtga tcttaactgt     540
cggatccaca aaaaaagtag aaataaatgt cagtactgtc ggtttcagaa atgccttgca     600
gtggggatgt ctcataatgc catcaggttt gggcggatgc cacaggccga aggagaaag     660 ctgttggcgg agatctccag tgtatatcga cagctgaatc cagagtccgc tgaccctccgg     720 gccctggcaa acatttgta tgactcatac ataaagtcct tcccgctgac caaagcaaag     780
gcgagggcga tcttgacagg aaagacaaca gacaaatcac cattcgttat ctatgacatg     840
aattccttaa tgatgggaga agataaaatc aagttcaaac acatcacccc cctgcaggag     900
cagagcaaag aggtggccat ccgcatcttt cagggctgcc agtttcgctc cgtggaggct     960
gtgcaggaga tcacagagta tgccaaaagc attcctggtt ttgtaaatct tgacttgaac    1020
gaccaagtaa ctctcctcaa atatggagtc cacgagatca tttacacaat gctggcctcc    1080
ttgatgaata agatgggggt tctcatatcc gagggccaag gcttcatgac aagggagttt    1140
ctaaagagcc tgcgaaagcc ttttggtgac tttatggagc caagtttga gtttgctgtg    1200 aagttcaatg cactggaatt agatgacagc gacttggcaa tatttattgc tgtcattatt    1260
ctcagtggag accgcccagg tttgctgaat gtgaagccca ttgaagacat tcaagacaac    1320
ctgctacaag ccctggagct ccagctgaag ctgaaccacc ctgagtcctc acagctgttt    1380
gccaagctgc tccagaaaat gacagacctc agacagattg tcacggaaca cgtgcagcta    1440
ctgcaggtga tcaagaagac ggagacagac atgagtcttc acccgctcct gcaggagatc    1500
tacaaggact tgtactag                                                  1518
```

<210> SEQ ID NO 14

```
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: Phospho-Ser

<400> SEQUENCE: 14

Lys Thr Thr Asp Lys Ser Pro Phe Val Ile Tyr Asp Cys
1               5                   10

<210> SEQ ID NO 15
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Ile Arg Ile Phe Gln Gly Cys Gln Phe
1               5

<210> SEQ ID NO 16
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Ile Ser Glu Gly Gln Gly Phe Met Thr Arg Glu
1               5                   10

<210> SEQ ID NO 17
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Gln Glu Ile Tyr Lys Asp Leu Tyr
1               5

<210> SEQ ID NO 18
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Lys Thr Thr Asp Lys Ser Pro Phe Val Ile Tyr Asp Met
1               5                   10

<210> SEQ ID NO 19
```

```
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 19
aaggtgaaga gcatcataac cct                                             23

<210> SEQ ID NO 20
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 20
caagaacagc aacgagtacc g                                               21

<210> SEQ ID NO 21
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 21
gggagtttgg ctccagagtt t                                               21

<210> SEQ ID NO 22
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 22
gctggcattc gtgatggagt cgt                                             23

<210> SEQ ID NO 23
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 23
aagctattgc gacatgatt                                                  19

<210> SEQ ID NO 24
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 24
```

```
gtgactggaa cactggtcct a                                              21

<210> SEQ ID NO 25
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 25
tgttcctctt aatcctgccc a                                              21

<210> SEQ ID NO 26
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 26
catgctcggc cctacatgg                                                 19

<210> SEQ ID NO 27
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 27
aagaaccttt catttcccct cct                                            23

<210> SEQ ID NO 28
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 28
tctcctttac cacaacaaga gca                                            23

<210> SEQ ID NO 29
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 29
ccctcagagt cagatcatct tct                                            23

<210> SEQ ID NO 30
<211> LENGTH: 23
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic primer"

<400> SEQUENCE: 30
tagtccttcc tacccaatt tcc                                           23

<210> SEQ ID NO 31
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 31 ttcagcccctt gcttgcctc                                              19

<210> SEQ ID NO 32
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 32
gagacccctg tgtcggttc                                               19

<210> SEQ ID NO 33
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 33
gcatggtgcc ttcgctga                                                18

<210> SEQ ID NO 34
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 34
acccttcacc aatgactcct atg                                          23

<210> SEQ ID NO 35
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 35
gtcggtgttc acggtgtacc                                              20
```

<210> SEQ ID NO 36
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 36
gcctggcctg cattaaaatg g                                     21

<210> SEQ ID NO 37
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 37
atggctacaa aatgcacaaa gtg                                   23

<210> SEQ ID NO 38
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 38
tgacaggtct atgctgaggg g                                     21

<210> SEQ ID NO 39
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 39
tgcttgcaca gagctacagt c                                     21

<210> SEQ ID NO 40
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 40
atggactacg ccatgaagtc t                                     21

<210> SEQ ID NO 41
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 41
gttgcaccgt ttcccggtaa                                              20

<210> SEQ ID NO 42
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 42
cagccaaggc aatttcagag c                                            21

<210> SEQ ID NO 43
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 43
tgaacgcagg aggtgtgatt g                                            21

<210> SEQ ID NO 44
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 44
tcttcagcca acaatcccaa tc                                           22

<210> SEQ ID NO 45
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 45
gtggtggaag accgtgacta c                                            21

<210> SEQ ID NO 46
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 46
agctccccct ggtagagac                                               19

<210> SEQ ID NO 47
<211> LENGTH: 21
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic primer"

<400> SEQUENCE: 47
cgaccaggcc aaaaagacaa g                                              21

<210> SEQ ID NO 48
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 48
tcttttgagg tggtcttcaa cg                                             22

<210> SEQ ID NO 49
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 49
tacattggct ctagtggctc c                                              21

<210> SEQ ID NO 50
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 50
tcacgccttt cataacacat tcc                                            23

<210> SEQ ID NO 51
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 51
gtcactggtc aactccagca c                                              21

<210> SEQ ID NO 52
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 52
tgtgtcttca ggggtcctta g                                              21
```

<210> SEQ ID NO 53
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 53
aggccaccag tgatgatgta actct                                    25

<210> SEQ ID NO 54
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 54
gatccgaaca cagcgtagat                                          20

<210> SEQ ID NO 55
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 55
ccagccacgt tgcattgtag                                          20

<210> SEQ ID NO 56
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 56
ccaacctgca caagttccct t                                        21

<210> SEQ ID NO 57
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 57
cacagagtcg tcatccgtca c                                        21

<210> SEQ ID NO 58
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 58
gtccagcaat ttaagccaat gtt                                        23

<210> SEQ ID NO 59
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 59
cttctcattc acaggggagg t                                          21

<210> SEQ ID NO 60
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 60
gctacgacgt gggctacag                                             19

<210> SEQ ID NO 61
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 61
ttggtcctta gccactcctt c                                          21

<210> SEQ ID NO 62
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 62 acactttac tccgaagtcg gt                                          22

<210> SEQ ID NO 63
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 63
ctgcgtgtgt gaaatgtcat tg                                         22

<210> SEQ ID NO 64
<211> LENGTH: 22
<212> TYPE: DNA

<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 64
tggcatctct gtgtcaacca tg                22

<210> SEQ ID NO 65
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 65
tgactgcagc aaatcgcttg g                21

<210> SEQ ID NO 66
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 66
aaagttccgc aggatttgga c                21

<210> SEQ ID NO 67
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 67
cttgcttcag aattgggcag t                21

<210> SEQ ID NO 68
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 68
cctgtgttcc ggtaaatgca g                21

<210> SEQ ID NO 69
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 69
cagcgtattt tactccgtcc ac                22

```
<210> SEQ ID NO 70
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 70
agtttgggat aggggctgct                                                20

<210> SEQ ID NO 71
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 71
cggtgctaac acgacaggg                                                 19

<210> SEQ ID NO 72
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 72
cccctctggt ggtagcgtta                                                20

<210> SEQ ID NO 73
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 73
ctcgacgttt gattaactgg tct                                            23

<210> SEQ ID NO 74
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 74
gaggactgga agctattctc aga                                            23

<210> SEQ ID NO 75
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

Synthetic primer"

<400> SEQUENCE: 75
ggctctatcg gtttcactac g                                    21

<210> SEQ ID NO 76
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 76 tcggggaac tttaacatcg t                                     21

<210> SEQ ID NO 77
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 77
ggtgaagacg cagaaacctt g                                    21

<210> SEQ ID NO 78
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 78
cacatcgcag atgctgcatt                                      20

<210> SEQ ID NO 79
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 79
gctttgactc gggtaacttc aca                                  23

<210> SEQ ID NO 80
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 80
cagtaggtga tggtgggaag ta                                   22

<210> SEQ ID NO 81
<211> LENGTH: 21

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 81
tgtaagagaa taaagcgtga a                                             21

<210> SEQ ID NO 82
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term acetylated"
<220> FEATURE:
<221> NAME/KEY: MOD_RES
<222> LOCATION: (6)..(6)
<223> OTHER INFORMATION: Phospho-Ser
<220> FEATURE:
<221> NAME/KEY: source
<223> OTHER INFORMATION: /note="C-term amidated"

<400> SEQUENCE: 82

Lys Thr Thr Asp Lys Ser Pro Phe Val Ile Tyr Asp Cys
1               5                   10

<210> SEQ ID NO 83
<211> LENGTH: 10
<212> TYPE: PRT
<213> ORGANISM: Mus musculus

<400> SEQUENCE: 83

Thr Thr Asp Lys Ser Pro Phe Val Ile Tyr
1               5                   10

<210> SEQ ID NO 84
<211> LENGTH: 10
<212> TYPE: PRT
<213> ORGANISM: Mus musculus

<400> SEQUENCE: 84

Thr Thr Asp Lys Ser Pro Phe Val Ile Tyr
1               5                   10

<210> SEQ ID NO 85
<211> LENGTH: 10
<212> TYPE: PRT
<213> ORGANISM: Mus musculus

<400> SEQUENCE: 85

Thr Ser Asn Asn Pro Pro Phe Val Ile His
1               5                   10

<210> SEQ ID NO 86
<211> LENGTH: 10
<212> TYPE: PRT
<213> ORGANISM: Mus musculus

<400> SEQUENCE: 86

Ser Ser His Asn Ala Pro Phe Val Ile His
1               5                   10
```

<210> SEQ ID NO 87
<211> LENGTH: 10
<212> TYPE: PRT
<213> ORGANISM: Homo sapiens

<400> SEQUENCE: 87

Thr Thr Asp Lys Ser Pro Phe Val Ile Tyr
1               5                   10

<210> SEQ ID NO 88
<211> LENGTH: 10
<212> TYPE: PRT
<213> ORGANISM: Bos sp.

<400> SEQUENCE: 88

Thr Thr Asp Lys Ser Pro Phe Val Ile Tyr
1               5                   10

<210> SEQ ID NO 89
<211> LENGTH: 10
<212> TYPE: PRT
<213> ORGANISM: Mus musculus

<400> SEQUENCE: 89

Thr Thr Asp Lys Ser Pro Phe Val Ile Tyr
1               5                   10

<210> SEQ ID NO 90
<211> LENGTH: 10
<212> TYPE: PRT
<213> ORGANISM: Oryctolagus sp.

<400> SEQUENCE: 90

Thr Thr Asp Lys Ser Pro Phe Val Ile Tyr
1               5                   10

<210> SEQ ID NO 91
<211> LENGTH: 10
<212> TYPE: PRT
<213> ORGANISM: Sus sp.

<400> SEQUENCE: 91

Thr Thr Asp Lys Ser Pro Phe Val Ile Tyr
1               5                   10

<210> SEQ ID NO 92
<211> LENGTH: 10
<212> TYPE: PRT
<213> ORGANISM: Gallus gallus

<400> SEQUENCE: 92

Thr Thr Asp Lys Ser Pro Phe Val Ile Tyr
1               5                   10

<210> SEQ ID NO 93
<211> LENGTH: 4
<212> TYPE: PRT
<213> ORGANISM: Unknown
<220> FEATURE:
<221> NAME/KEY: source
<223> OTHER INFORMATION: /note="Description of Unknown: DEAD box
      polypeptide 17"

<400> SEQUENCE: 93

```
Asp Glu Ala Asp
1

<210> SEQ ID NO 94
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Lys Thr Thr Asp Lys Ser Pro Phe Val Ile Tyr Asp Cys
1               5                   10
```